United States Patent
Maginot et al.

(10) Patent No.: US 6,743,218 B2
(45) Date of Patent: Jun. 1, 2004

(54) RETRACTABLE CATHETER SYSTEMS AND ASSOCIATED METHODS

(75) Inventors: Paul J. Maginot, Fishers, IN (US); Thomas J. Maginot, Crown Point, IN (US)

(73) Assignee: CathLogic, Inc., Crown Point, IN (US)

( * ) Notice: Subject to any disclaimer, the term of this patent is extended or adjusted under 35 U.S.C. 154(b) by 294 days.

(21) Appl. No.: 10/006,799

(22) Filed: Dec. 4, 2001

(65) Prior Publication Data

US 2002/0087108 A1 Jul. 4, 2002

Related U.S. Application Data

(63) Continuation-in-part of application No. 09/716,815, filed on Nov. 20, 2000, and a continuation-in-part of application No. 09/716,308, filed on Nov. 20, 2000, now Pat. No. 6,585,705, said application No. 09/716,815, is a continuation-in-part of application No. 09/443,876, filed on Nov. 19, 1999, now Pat. No. 6,475,207, said application No. 09/716,308, is a continuation-in-part of application No. 09/246,831, filed on Feb. 8, 1999, now Pat. No. 6,190,371.

(60) Provisional application No. 60/116,017, filed on Jan. 15, 1999.

(51) Int. Cl.[7] .............................................. A61M 31/00
(52) U.S. Cl. ...................... 604/510; 604/508; 604/523; 604/6.16; 604/28; 604/29; 604/165.02
(58) Field of Search ............................... 604/4.01, 6.16, 604/19, 27–29, 43, 500, 506–508, 510, 93.01, 158, 163, 164.01, 164.02, 164.04, 164.08, 164.09, 165.01, 165.02, 167.01, 167.04, 174, 263, 264, 523, 533, 540–544

(56) References Cited

U.S. PATENT DOCUMENTS

| | | |
|---|---|---|
| 2,448,232 A | 8/1948 | Muse |
| 3,894,540 A | 7/1975 | Bonner, Jr. |
| 4,014,333 A | 3/1977 | McIntyre |
| 4,023,559 A | 5/1977 | Gaskell |

(List continued on next page.)

OTHER PUBLICATIONS

Pages 366–367 of *Interventional Radiology*, vol. One, Second Edition.
Marketing brochure from Cook Critical Care, A division of Cook, Incorporated.
Marketing brochure from Micro Therapeutics, Inc.
Marketing brochure entitled "Bard Access Systems Hickman: ® Hemodialysis/Plasmapheresis Catheter", Bard Access Systems, Hickman, Groshong, Designs for Life ™, 5425 West Amelia Earhart Drive, Salt Lake City, Utah 84116. Published at least as early as May 13, 1998.

(List continued on next page.)

*Primary Examiner*—Brian L. Casler
*Assistant Examiner*—Jennifer Maynard
(74) *Attorney, Agent, or Firm*—Paul J. Maginot

(57) ABSTRACT

A method of performing dialysis with a catheter system which includes (i) a working catheter having a distal working orifice, and (ii) a guide catheter having a guide lumen and a distal guide orifice is disclosed. The method includes the step of locking the working catheter in an operative position in which (i) the working catheter extends through the guide lumen of the guide catheter and out of the distal guide orifice of the guide catheter, and (ii) the distal working orifice of the working catheter is positioned outside of the guide catheter. The method further includes the step of performing a dialysis procedure including advancing and withdrawing blood through the working catheter while the working catheter is locked in the operative position. Moreover, the method includes the step of, after the dialysis procedure performing step, locking the working catheter in a stowed position in which (i) the working catheter extends into the guide lumen of the guide catheter, and (ii) the distal working orifice of the working catheter is positioned within the guide lumen of the guide catheter.

67 Claims, 44 Drawing Sheets

U.S. PATENT DOCUMENTS

| | | |
|---|---|---|
| 4,157,709 A | 6/1979 | Schuster et al. |
| 4,266,999 A | 5/1981 | Baier |
| 4,324,262 A | 4/1982 | Hall |
| 4,385,631 A * | 5/1983 | Uthmann .................... 604/284 |
| 4,392,855 A | 7/1983 | Oreopoulos et al. |
| 4,406,656 A | 9/1983 | Hattler et al. |
| 4,431,426 A | 2/1984 | Groshong et al. |
| 4,432,752 A * | 2/1984 | Marlon ....................... 604/500 |
| 4,437,857 A | 3/1984 | Goldstein et al. |
| 4,457,313 A | 7/1984 | Alter |
| 4,468,216 A | 8/1984 | Muto |
| 4,493,696 A | 1/1985 | Uldall |
| 4,583,968 A | 4/1986 | Mahurkar |
| 4,626,240 A | 12/1986 | Edelman et al. |
| 4,665,925 A | 5/1987 | Millar |
| 4,738,667 A * | 4/1988 | Galloway ................... 604/530 |
| 4,900,202 A | 2/1990 | Wienhold |
| 4,936,826 A * | 6/1990 | Amarasinghe .............. 604/507 |
| 5,013,194 A | 5/1991 | Wienhold |
| 5,049,138 A * | 9/1991 | Chevalier et al. ........... 604/265 |
| 5,053,023 A | 10/1991 | Martin |
| 5,156,592 A | 10/1992 | Martin et al. |
| 5,190,529 A | 3/1993 | McCrory et al. |
| 5,213,567 A | 5/1993 | Masaki |
| 5,215,530 A | 6/1993 | Hogan |
| 5,236,424 A | 8/1993 | Imran |
| 5,250,034 A | 10/1993 | Appling et al. |
| 5,261,416 A | 11/1993 | Taussig |
| 5,272,527 A | 12/1993 | Schatz et al. |
| 5,279,590 A | 1/1994 | Sinko et al. |
| 5,370,613 A | 12/1994 | Helmy |
| 5,405,320 A | 4/1995 | Twardowski et al. |
| 5,405,323 A | 4/1995 | Rogers et al. |
| 5,417,669 A | 5/1995 | Castaneda et al. |
| 5,470,180 A | 11/1995 | Jore |
| 5,498,240 A | 3/1996 | Bagaoisan et al. |
| 5,514,112 A | 5/1996 | Chu et al. |
| 5,531,780 A * | 7/1996 | Vachon ....................... 607/120 |
| 5,569,182 A | 10/1996 | Twardowski et al. |
| 5,569,204 A | 10/1996 | Cramer |
| 5,591,138 A | 1/1997 | Vaillancourt |
| 5,599,317 A | 2/1997 | Hauser |
| 5,616,131 A | 4/1997 | Sauer et al. |
| 5,624,396 A | 4/1997 | McNamara et al. |
| 5,681,336 A | 10/1997 | Clement et al. |
| 5,779,404 A | 7/1998 | Jore |
| 5,843,017 A * | 12/1998 | Yoon ........................... 604/22 |
| 5,971,958 A | 10/1999 | Zhang |
| 6,007,522 A | 12/1999 | Agro et al. |
| 6,080,170 A | 6/2000 | Nash et al. |
| 6,099,508 A | 8/2000 | Bousquet |
| 6,156,016 A | 12/2000 | Maginot |
| 6,190,353 B1 | 2/2001 | Makower et al. |
| 6,190,371 B1 | 2/2001 | Maginot et al. |
| 6,241,744 B1 | 6/2001 | Imran et al. |
| 6,261,257 B1 | 7/2001 | Uflacker et al. |
| 6,283,951 B1 | 9/2001 | Flaherty et al. |

OTHER PUBLICATIONS

Crain M: Management of fibrin sheaths I: Percutaneous fibrin sheath stripping. Seminars in Dialysis 1998:11(6):336–341.

Lund GB: Management of fibrin sheaths II: Thrombolytic therapy. Seminars in Dialysis 1998:11(6):342–346.

Xiang DZ, Verbeken EK, Van Lommel ATL, et al: Composition and formation of the sleeve enveloping a central venous catheter. J Vasc Surg 1998;28:260–271.

Merport M. Murphy TP, Egglin TK, et al,: Fibrin sheath stripping versus catheter exchange for the treatment of failed tunneled homodialysis catheters: Randomized clinical trial. JVIR 2000;11:1115–1120.

Savader SJ, Haikal LC, Ehrman KO, et al; Hemodialysis catheter–associated fibrin sheaths: Treatment with a Low–dose rt–PA infusion. JVIR 2000;11:1131–1136.

Gray RJ, Levitin A. Buck D, et al: Percutaneous fibrin sheath stripping versus transcatheter urokinase infusion for malfunctioning well–positioned tunneled central venous dialysis catheters: A prospective randomized trial. JVIR 2000:11:1121–1129.

Marketing brochure for Cook Inc., Bunchman Coaxial Double Lumen Hemodialysis/Hemofiltration Catheter Set, © 1995.

* cited by examiner

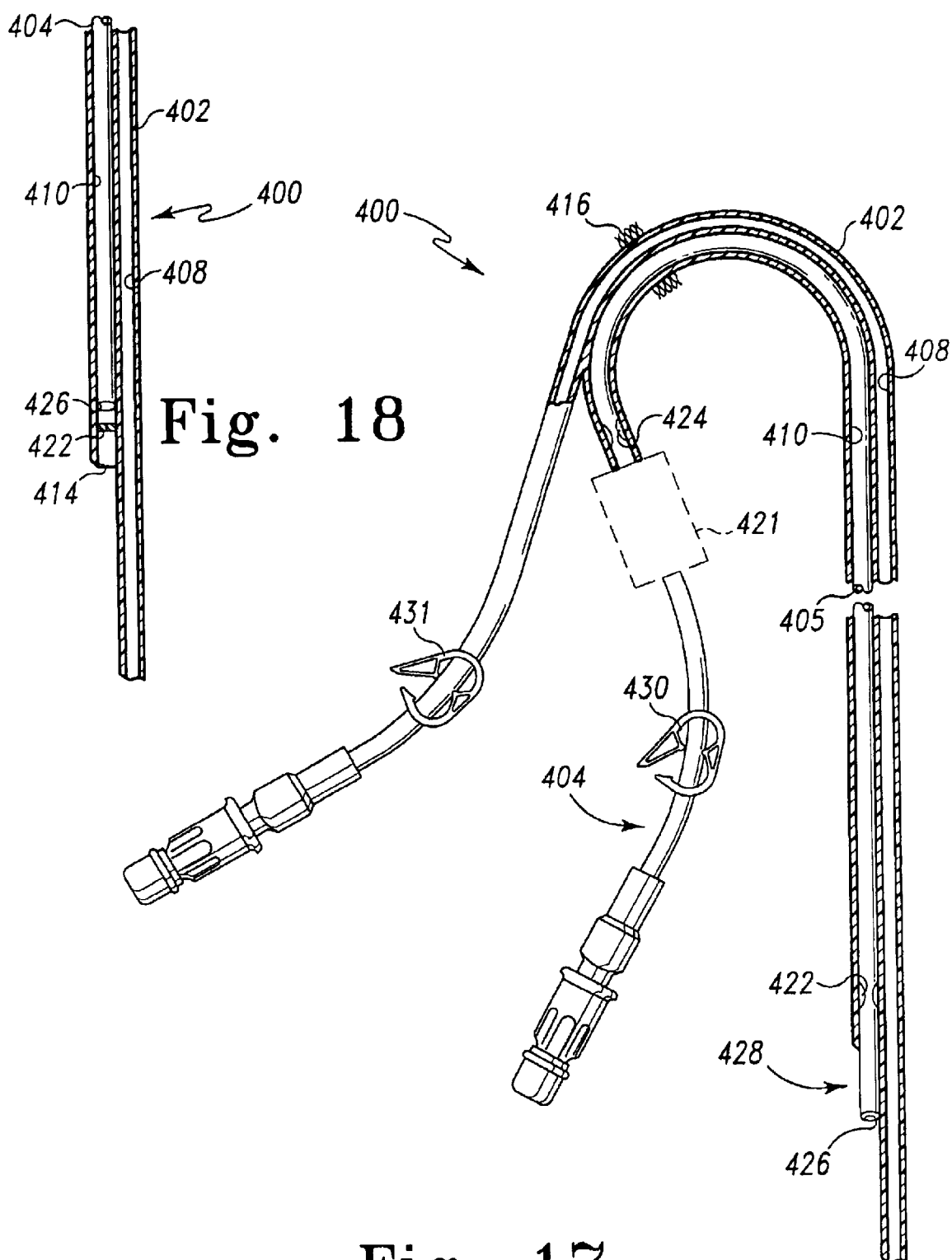

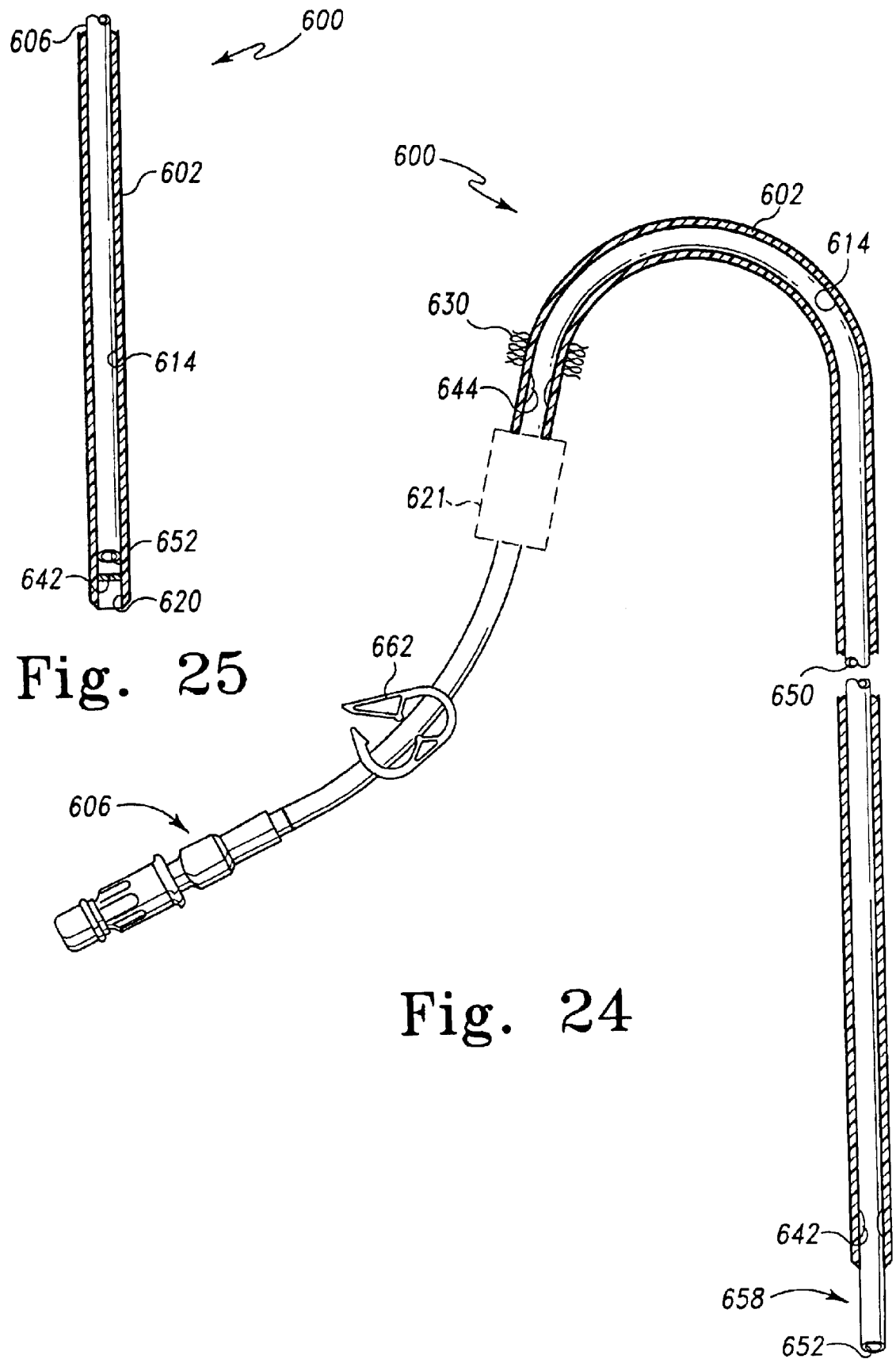

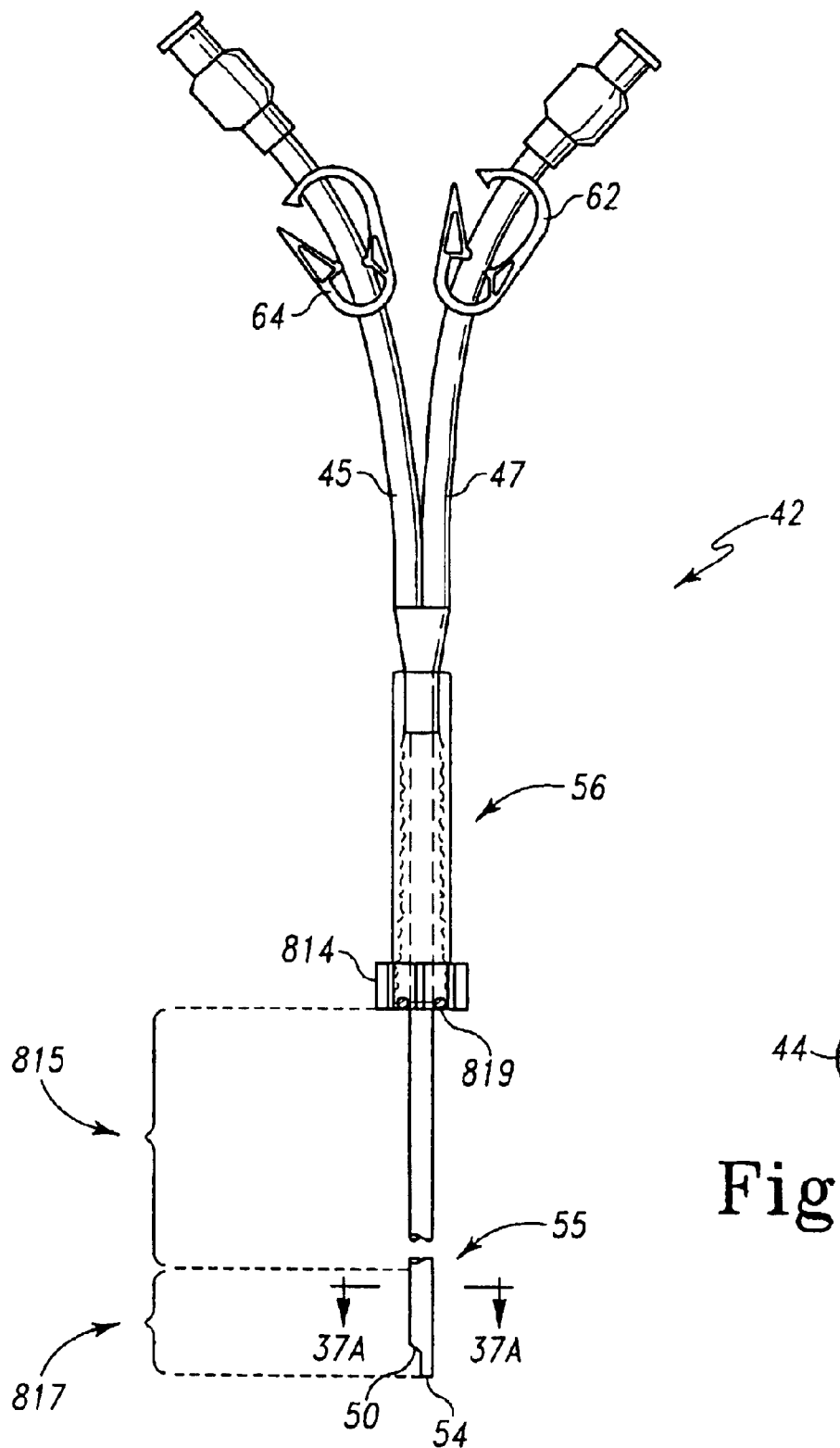
Fig. 37A
Fig. 37

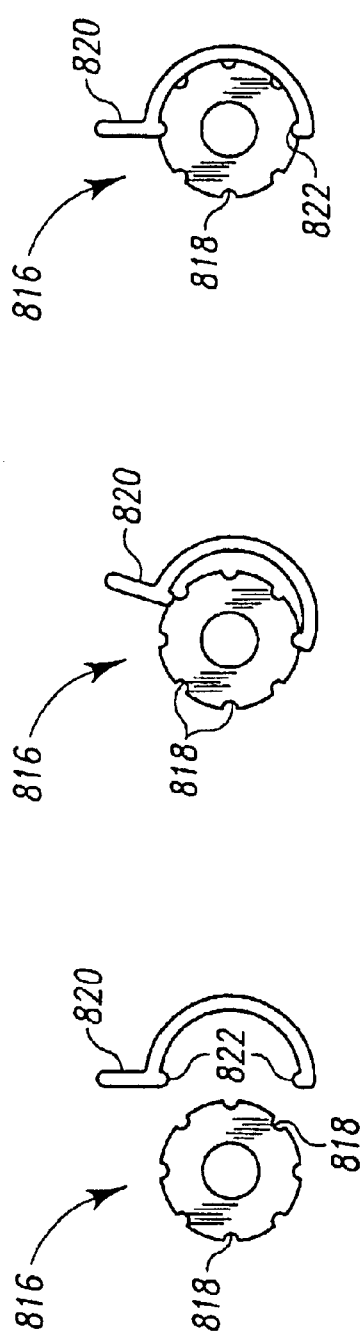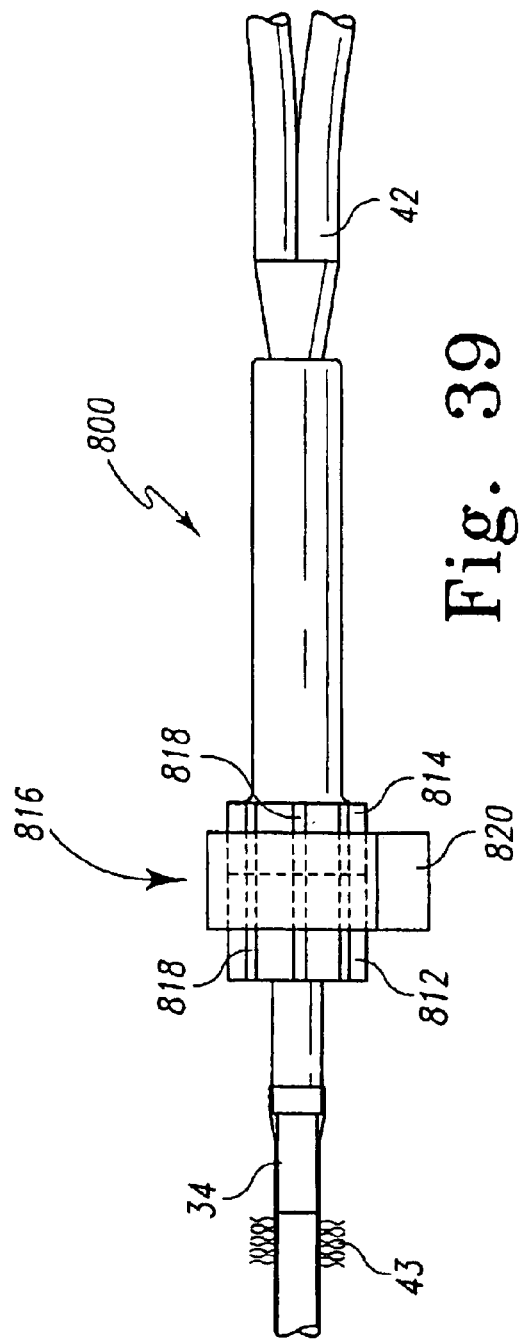

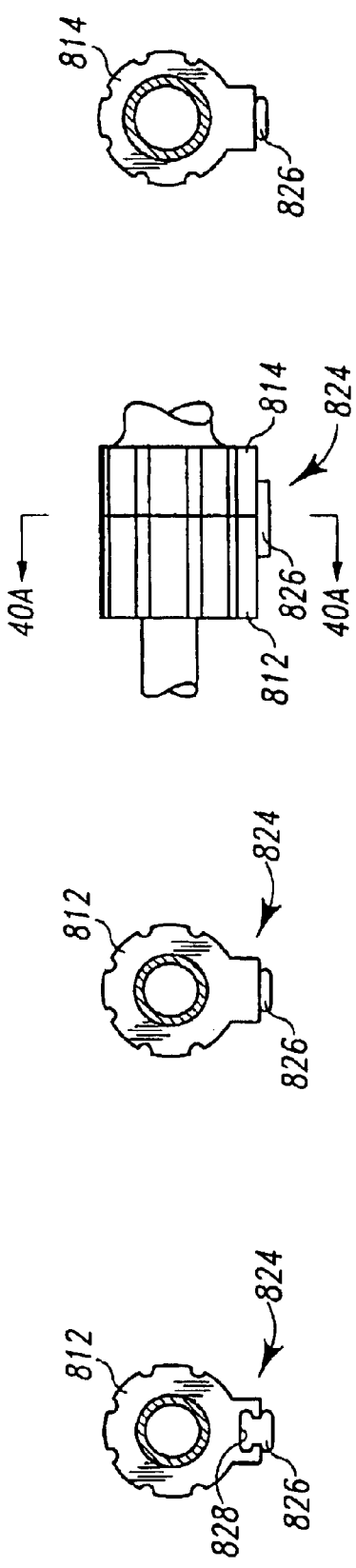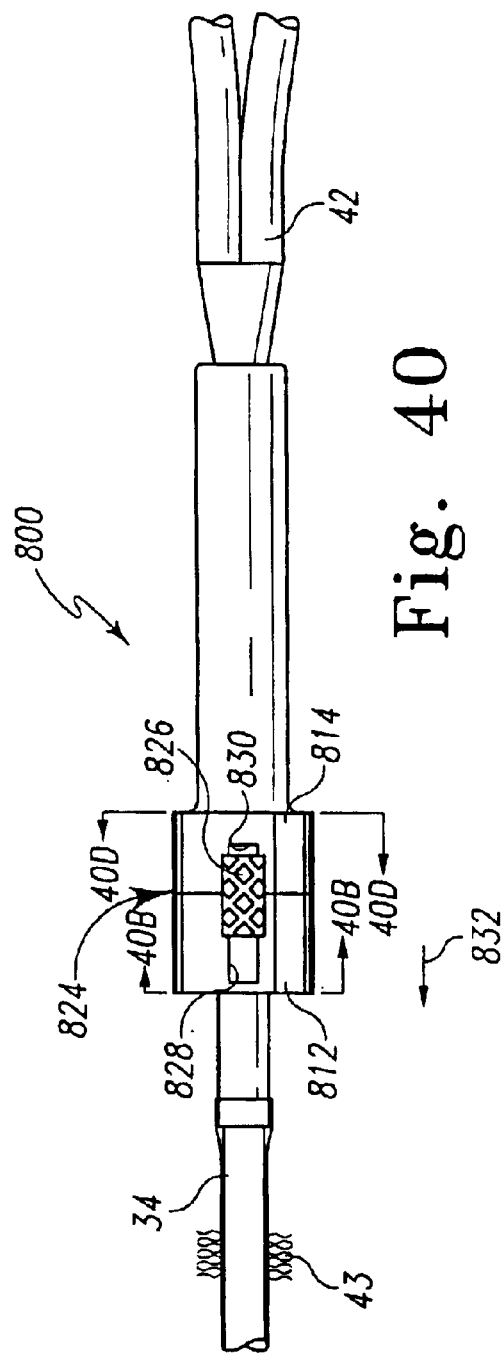

RETRACTABLE CATHETER SYSTEMS AND ASSOCIATED METHODS

This application is a continuation-in-part of both (i) application Ser. No. 09/716,815, filed on Nov. 20, 2000, and (ii) application Ser. No. 09/716,308, filed on Nov. 20, 2000, now U.S. Pat No. 6,585,705. Each of the above-identified patent applications Ser. Nos. 09/716,815 and 09/716,308 is a continuation-in-part of application Ser. No. 09/443,876, filed on Nov. 19, 1999, now U.S. Pat. No. 6,475,207 which in turn is a continuation-in-part of co-pending application Ser. No. 09/246,831, filed on Feb. 8, 1999, (now U.S. Pat. No. 6,190,371) which in turn claims the benefit of U.S. Provisional Application Serial No. 60/116,017, filed Jan. 15, 1999. The disclosures of each of the above-identified patent applications and patent being hereby totally incorporated by reference in their entirety.

CROSS REFERENCE

Cross reference is made to co-pending U.S. patent application Ser. No. 10/007,679 (Attorney Docket No.1537-0021), entitled "Subcutaneous Port Catheter System and Associated Method" by Thomas J. Maginot filed on the same date herewith, and co-pending U.S. patent application Ser. No. 10/005,277 (Attorney Docket No.1537-0022), entitled "Medical Procedure Using Catheter System having Removability Feature" by Thomas J. Maginot and Paul J. Maginot filed on the same date herewith, and co-pending U.S. patent application Ser. No. 09/716,814, entitled "Catheter Systems and Associated Methods having Removability Feature" by Thomas J. Maginot filed on Nov. 20, 2000, and also U.S. Pat. No. 6,156,016 issued to Maginot on Dec. 5, 2000, and also U.S. Pat. No. 5,989,213 issued to Maginot on Nov. 23, 1999. The disclosures of each of the above-identified patent applications and patents being hereby totally incorporated by reference in their entirety.

BACKGROUND OF THE INVENTION

The present invention relates generally to catheters, and more particularly to retractable catheter systems for use in a body of a patient and associated methods which maintain fluid flow in the catheter system.

Various medical procedures require that a patient be catheterized. For example, catheterization may be required when a patient undergoes hemodialysis or has a clot aspirated from a blood vessel. Generally, the length of time the patient will be catheterized dictates whether a physician will utilize a "temporary catheterization technique" (i.e. a technique in which the catheter is left in a blood vessel for a relatively short period of time such as a few minutes, hours, days, or weeks) or a "permanent catheterization technique" (i.e. a technique in which the catheter is left in a blood vessel for a relatively long period of time such as several months or indefinitely).

For example, a procedure in which a clot is aspirated from a blood vessel typically includes placing the catheter in the blood vessel for a relatively short period of time such as a few minutes to a few hours and then withdrawing the catheter once the clot has been removed. Therefore, when performing such an aspiration procedure, it is common for a physician to use the temporary catheterization technique to place the catheter in the blood vessel of the patient.

On the other hand, when a procedure is performed to effect hemodialysis, a physician may place a catheter in the blood vessel for a relatively long period of time. In particular, a patient suffering from kidney failure who is involved in a hemodialysis regimen typically requires a dialysis session three days per week for an indefinite period of time whereby extra fluid, chemicals, and wastes are removed from his/her body. A patient who is involved in such a hemodialysis regimen may need a catheter placed in his/her blood vessel for a relatively long period of time in order to provide a ready means for vascular access into his/her bloodstream over such relatively long period of time. This long term placement of the catheter for dialysis purposes may be desirable for a number of reasons.

Firstly, a patient may have experienced progressive loss of other conventional long term vascular access possibilities such as surgically created arteriovenous fistulas. Accordingly, the long term placement of the catheter in the patient's blood vessel may be the best alternative for the patient as he/she proceeds with the hemodialysis regimen.

Additionally, the long term placement of the catheter in the patient's blood vessel may be desirable after initial creation of an arteriovenous fistula in the patient's body. In particular, it is desirable to provide a ready means for vascular access into the patient's bloodstream during a maturation period of the arteriovenous fistula. The maturation period allows the arteriovenous fistula to develop sufficiently so that it will function as a ready means for vascular access into the patient's bloodstream which may be safely punctured multiple times per week for hemodialysis. The length of time of this maturation period is typically on the order of several weeks (e.g. three weeks) to many months (e.g. six months).

Therefore, when performing a hemodialysis procedure, it is common for a physician to use the permanent catheterization technique to place the catheter in the blood vessel of the patient.

These two catheterization techniques are significantly different with respect to their complexity and degree of invasiveness. For example, in the case of the temporary catheterization technique, it is common to insert a temporary catheter into a patient's blood vessel using a "direct puncture technique." This technique entails creating a small incision in a patient's skin with a scalpel directly over the blood vessel to be catheterized. A needle is then advanced through the skin incision and subcutaneous tissue and into the blood vessel. Thereafter, a guidewire is advanced through the needle into the blood vessel and the needle is subsequently removed over the guidewire. Then, one or more tubular vessel dilators are used to widen the opening defined in the skin and subcutaneous tissue, and further to widen the opening defined in the blood vessel wall to a caliber similar to that of the temporary catheter. The temporary catheter is then advanced over the guidewire and into the blood vessel. Thereafter, the guidewire is removed.

When the temporary catheterization technique is used during a clot aspiration procedure, two catheters are usually placed in the blood vessel of a patient. In particular, an outer catheter is usually placed within the blood vessel using the above described direct puncture technique so that its distal orifice is located near the clot. Thereafter, an inner catheter having a smaller caliber relative to the outer catheter is advanced through a lumen of the outer catheter. While the inner catheter is positioned within the outer catheter, an aspiration vacuum is applied to the inner catheter with a syringe. If the size of the clot (or fragments thereof) are smaller than the inner diameter of the inner catheter, then the clot or clot fragments are drawn into and through the inner catheter thereby removing the clot from the blood vessel. If the size of the clot or clot fragments are larger than the inner diameter of the inner catheter, then the clot or clot fragments are drawn to a location adjacent to the distal orifice of the inner catheter. Subsequently, while the aspiration vacuum is still being applied, the inner catheter is withdrawn from the outer catheter thereby additionally withdrawing the clot or clot fragments from the outer catheter and the patient's blood vessel. Thereafter, the outer catheter remains temporarily in place within the blood vessel of the patient for subsequent injections of radiographic contrast for imaging purposes to determine the extent of clot remaining in the blood vessel as well as to determine if clot has migrated to another location within the blood vessel. The outer catheter, which remains temporarily in place in the blood vessel, provides a conduit for the inner catheter to be advanced back into the patient's blood vessel for additional aspiration attempts which are usually required for complete removal of the clot from the blood vessel.

If an outer catheter needs to be replaced during a clot aspiration procedure because of catheter malfunction, such replacement can be accomplished by advancing a guidewire through the lumen of the outer catheter and into the blood vessel. The existing outer catheter can then be removed over the guidewire to a location outside of the patient's body. Thereafter, a new outer catheter is placed in the patient's blood vessel by advancing the new outer catheter over the guidewire as discussed above.

In contrast to the temporary catheterization technique, the permanent catheterization technique typically entails inserting a permanent catheter into a patient's blood vessel using a "tunneled catheter technique." The tunneled catheter technique includes (i) creating a first opening by making a small incision in a patient's skin with a scalpel directly over the blood vessel to be catheterized, (ii) puncturing the blood vessel at a location directly below the first opening by advancing a needle through the skin incision and subcutaneous tissue and into the blood vessel, (iii) advancing a guidewire through the needle into the blood vessel, (iv) removing the needle over the guidewire, (v) passing one or more tubular vessel dilators over the guidewire to widen the opening defined in the skin and subcutaneous tissue, and further to widen the opening defined in the blood vessel wall to a caliber similar to that of the tubular guide, (vi) advancing the tubular guide over the guidewire and into the blood vessel, (vii) thereafter, creating a second opening in the patient's skin spaced apart at least several centimeters from the first opening, (viii) advancing a tunneling instrument from the second opening to the first opening so as to create a passageway within the subcutaneous tissue under the skin between the first opening and the second opening, (ix) advancing a permanent catheter having a tissue ingrowth member attached to an outer surface thereof into the second opening and through the passageway such that a distal end of the permanent catheter is located adjacent the first opening, (x) inserting the distal end of the permanent catheter through the tubular guide member and into the blood vessel to be catheterized whereby the tissue ingrowth member is positioned in the subcutaneous tissue, (xi) removing the tubular guide member, and (xii) closing the first opening with suture whereby the permanent catheter (a) is no longer exposed through the first opening, (b) extends for at least several centimeters under the patient's skin between the second opening and the location where the permanent catheter enters the blood vessel, and (c) extends out of the second opening so that a proximal end of the permanent catheter is located outside of the patient's body.

In contrast to the direct puncture catheter technique, the tunneled catheter technique results in the placement of a catheter in a patient's body in a manner which allows the catheter to remain safely in the patient's body for a relatively long period of time. For example, a degree of safety is achieved by separating the following two openings by at least several centimeters: (i) the skin opening through which the catheter enters the patient's body, and (ii) the blood vessel opening through which the catheter enters the patient's vascular system. This safety feature decreases the likelihood that bacteria will migrate up the length of the catheter from the skin opening and cause an infection at the blood vessel opening.

In addition, another degree of safety is achieved by providing a tissue ingrowth member which is attached to and extends around an outer surface of the catheter. As the catheter is left in the patient's body over a period of time, the tissue ingrowth member becomes affixed to the subcutaneous tissue of the patient's body thereby providing a secure attachment of the catheter to the patient's body. Providing a secure attachment between the catheter and the patient's body reduces the likelihood that the catheter will be inadvertently removed or withdrawn from the patient's body. Moreover, since the subcutaneous tissue becomes attached to the tissue ingrowth member, a physical barrier is created between following two openings: (i) the skin opening through which the catheter enters the patient's body, and (ii) the blood vessel opening through which the catheter enters the patient's vascular system. This physical barrier further decreases the likelihood that bacteria will migrate up the length of the catheter from the skin opening and cause an infection at the blood vessel opening.

While the tunneled catheter technique provides the significant advantage of allowing the catheter to remain safely in the patient's body for a relatively long period of time, significant disadvantages of the tunneled catheter technique exists. For example, when a catheter remains in a blood vessel for a long period of time, there is a tendency for blood clots including fibrin (e.g. in the form of a fibrin sheath) to attach to and build-up on the outer and inner surfaces of the portion of the catheter which is located within the blood vessel. The above described attachment and build-up tends to occlude the various distal orifices defined in the catheter which enable fluid movement into and out of the catheter. For instance, attempts at withdrawing blood through the catheter may be unsuccessful due to blood clots creating a "ball-valve" effect which occlude the various distal orifices of the catheter.

When occlusion of the various distal orifices of the catheter occurs due to the above described blood clot attachment and build-up, a physician has several options for eliminating the occlusion thereby reestablishing access to the vascular system. One option is to remove the occluded catheter and replace it with a new catheter. However, in contrast to the ease of exchanging a catheter which was placed in the patient's body using the direct puncture technique, exchanging a catheter which was placed in the patient's body using the tunneled catheter technique is substantially more complicated and invasive. This is true since in order to remove the occluded catheter from the patient's body, the physician must surgically dissect the tissue ingrowth member which is secured to the outer surface of the catheter from the patient's subcutaneous tissue. Recall that the tissue ingrowth member becomes affixed to the subcutaneous tissue over a period of time. Thereafter, the physician would place a new catheter into the patient's body generally using the above described tunneled catheter technique. Thus, this option is undesirable since it requires additional surgery which further traumatizes the patient and increases the cost of the medical care.

Another option for eliminating the occlusion of the various distal orifices of the catheter in order to reestablish access to the vascular system involves the performance of a medical procedure in which a blood clot-dissolving medication such as urokinase is infused into the catheter. However, this medication is not always successful in eliminating the occlusion of the various distal orifices of the catheter. In addition, infusion of the medication into the catheter subjects the patient to potential bleeding complications due to the medication entering the vascular system and being circulated systemically. Further, this medication is expensive. Thus, this option has serious drawbacks as well.

An additional option for eliminating the occlusion of the various distal orifices of the catheter in order to reestablish access to the vascular system involves the performance of a medical procedure in which an intravascular snare is introduced into the blood vessel in order to physically strip off any blood clots or fibrin sheath which has attached and built-up on the distal portion of the catheter. However, for catheters placed in veins, this medical procedure requires a venopuncture in the femoral or jugular vein which is invasive and can be uncomfortable for a patient. Furthermore, this option requires the use of (i) an intravascular snare, (ii) a physician experienced in catheter techniques, and (iii) an angiographic suite to provide fluoroscopic imaging. Use of each of items (i), (ii), and (iii) above causes this option to be relatively expensive. Consequently, this option also has significant disadvantages.

What is needed therefore is a method and apparatus which reduces the likelihood of occlusion of the various distal orifices of a catheter which has been placed in a patient's body using the tunneled catheter technique which overcomes one or more of the above-mentioned drawbacks. What is also needed is an improved long-term catheter system and associated method of maintaining fluid flow in the catheter system.

SUMMARY OF THE INVENTION

In accordance with one embodiment of the present invention, there is provided a catheter system which includes a working catheter having a distal working orifice. The catheter system further includes a guide catheter having a guide lumen and a distal guide orifice. The catheter system additionally includes a locking mechanism which locks the working catheter relative to the guide catheter in (i) an operative position, and (ii) a stowed position. When the working catheter is locked in the operative position, (i) the working catheter extends through the guide lumen of the guide catheter and out of the distal guide orifice of the guide catheter, and (ii) the distal working orifice of the working catheter is positioned outside of the guide catheter. When the working catheter is locked in the stowed position, (i) the working catheter extends into the guide lumen of the guide catheter, and (ii) the distal working orifice of the working catheter is positioned within the guide lumen of the guide catheter.

Pursuant to another embodiment of the present invention, there is provided a method of performing dialysis with a catheter system which includes (i) a working catheter having a distal working orifice, and (ii) a guide catheter having a guide lumen and a distal guide orifice. The method includes the step of locking the working catheter in an operative position in which (i) the working catheter extends through the guide lumen of the guide catheter and out of the distal guide orifice of the guide catheter, and (ii) the distal working orifice of the working catheter is positioned outside of the guide catheter. The method further includes the step of advancing and withdrawing blood through the working catheter while the working catheter is locked in the operative position. Also, the method includes the step of locking the working catheter in a stowed position in which (i) the working catheter extends into the guide lumen of the guide catheter, and (ii) the distal working orifice of the working catheter is positioned within the guide lumen of the guide catheter.

According to still another embodiment of the present invention, there is provided a method of performing a medical procedure with a catheter system which includes (i) a working catheter having a distal working orifice, and (ii) a guide catheter having a guide lumen and a distal guide orifice. The method includes the step of locking the working catheter in an operative position in which (i) the working catheter extends through the guide lumen of the guide catheter and out of the distal guide orifice of the guide catheter, and (ii) the distal working orifice of the working catheter is positioned outside of the guide catheter. Moreover, the method includes the step of advancing and withdrawing fluid through the working catheter while the working catheter is locked in the operative position. The method also includes the step of locking the working catheter in a stowed position in which (i) the working catheter extends into the guide lumen of the guide catheter, and (ii) the distal working orifice of the working catheter is positioned within the guide lumen of the guide catheter.

In accordance with yet another embodiment of the present invention, there is provided a catheter system which includes a multi-lumen working catheter having a first distal working orifice and a second distal working orifice. The catheter system further includes a guide catheter having a guide lumen and a distal guide orifice. Also, the catheter system includes a locking mechanism which locks the working catheter relative to the guide catheter in (i) an operative position, and (ii) a stowed position. When the working catheter is locked in the operative position, (i) the working catheter extends through the guide lumen of the guide catheter and out of the distal guide orifice of the guide catheter, and (ii) the first distal working orifice and the second distal working orifice are each positioned outside of the guide catheter. Additionally, when the working catheter is locked in the stowed position, (i) the working catheter extends into the guide lumen of the guide catheter, and (ii) the first distal working orifice and the second distal working orifice are each positioned within the guide lumen of the guide catheter.

It is therefore an object of the present invention to provide a new and useful catheter system for use in a body of a patient.

It is also an object of the present invention to provide a new and useful long-term catheter system for use in a body of a patient.

It is another object of the present invention to provide an improved longterm catheter system for use in a body of a patient.

It is yet another object of the present invention to provide a new and useful method of performing dialysis with a catheter system.

It is still another object of the present invention to provide an improved method of performing dialysis with a catheter system.

Other objects and benefits of the present invention can be discerned from the following description and accompanying drawings.

BRIEF DESCRIPTION OF THE DRAWINGS

FIG. 8A shows a separating diaphragm being used in place of the proximal valve;

FIG. 17 is a view similar to FIG. 3, but showing another catheter system which incorporates the features of the present invention therein, with the working catheter shown positioned in the operative position;

FIG. 18 is a fragmentary cross sectional view of a distal portion of the catheter system of FIG. 17, but showing the working catheter positioned in the stowed position;

FIG. 24 is a view similar to FIG. 3, but showing still another catheter system which incorporates the features of the present invention therein, with the working catheter shown positioned in the operative position;

FIG. 25 is a fragmentary cross sectional view of a distal portion of the catheter system of FIG. 24, but showing the working catheter positioned in the stowed position;

FIG. 37 is an enlarged side elevational view of the working catheter of the long-term dialysis catheter system shown in FIG. 38A;

FIG. 37A is an enlarged cross sectional view of the guide catheter taken along the line 37A—37A of FIG. 37 as viewed in the direction of the arrows;

FIG. 39 is an enlarged fragmentary elevational view of the catheter system of FIG. 38A showing a supplemental locking system;

FIGS. 39A, 39B, and 39C are various views of the locking clip of the supplemental locking system of FIG. 39 being applied over the finger grips;

FIG. 40 is an enlarged fragmentary elevational view of the catheter system of FIG. 38A showing an alternative supplemental locking system; and FIG. 40A is an enlarged cross sectional view of the first finger grip and slider taken along the line 40A—40A of FIG. 40C as viewed in the direction of the arrows (Note that the dialysis catheter is shown removed for clarity of description);

FIG. 40B is an enlarged cross sectional view of the first finger grip and slider taken along the line 40B—40B of FIG. 40 as viewed in the direction of the arrows (Note that the dialysis catheter is shown removed for clarity of description);

FIG. 40C is enlarged fragmentary elevational view of the catheter system of FIG. 40 showing an alternative view of the first and second finger grips;

FIG. 40D is an enlarged cross sectional view of the second finger grip and slider taken along the line 40D—40D of FIG. 40 as viewed in the direction of the arrows (Note that only the second finger grip and slider is shown for clarity of description);

FIGS. 52 and 53 are views similar to FIGS. 10 and 11, but showing yet another catheter system that incorporates the features of the present invention therein. Note that FIG. 52 shows the working catheter locked to the guide catheter in its retracted position, while FIG. 53 shows the working catheter locked to the guide catheter in its retracted position.

DESCRIPTION OF THE PREFERRED EMBODIMENTS

Figure 1:
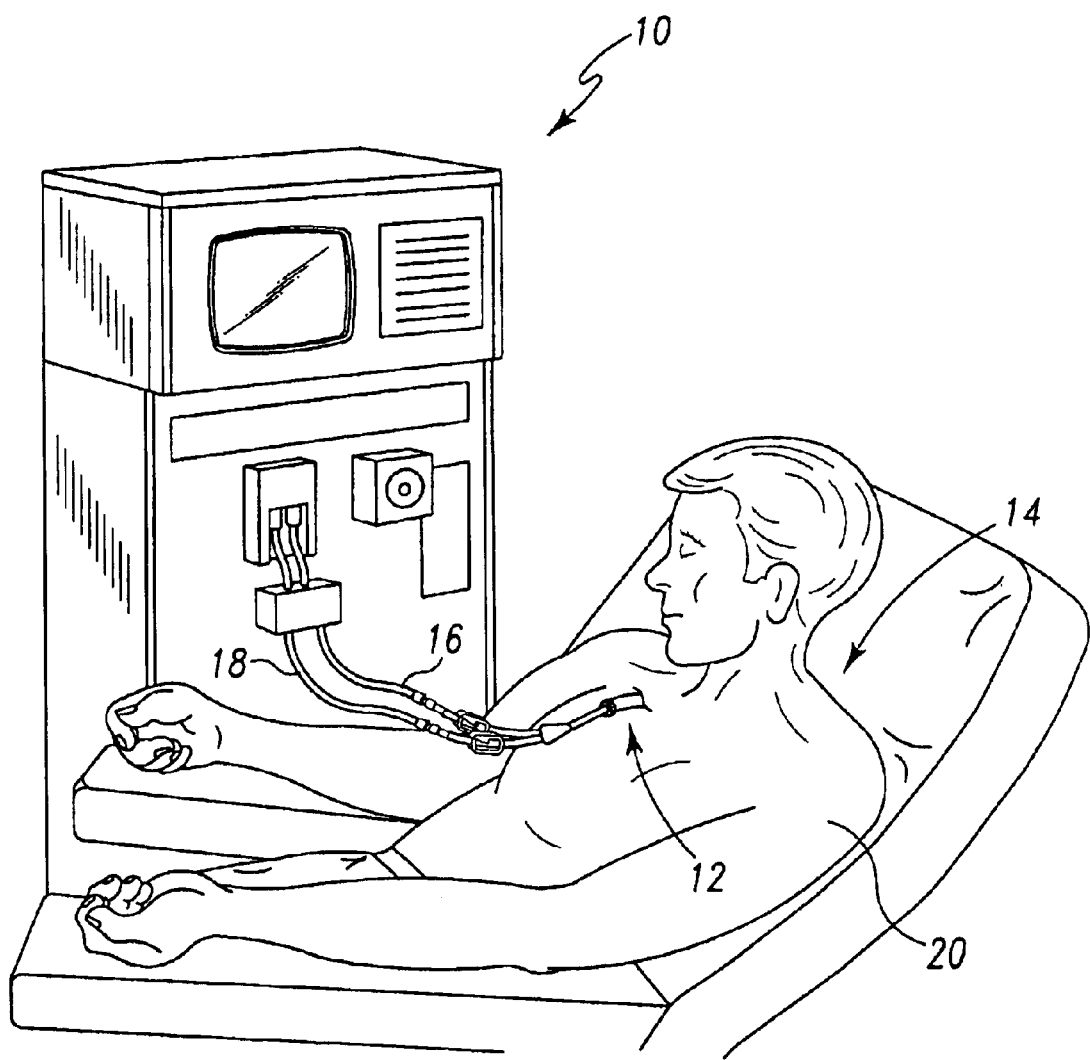
FIG. 1 is a perspective view of a patient undergoing a dialysis procedure utilizing the catheter system of the present invention.

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

I. Catheter System 12

Figure 9:
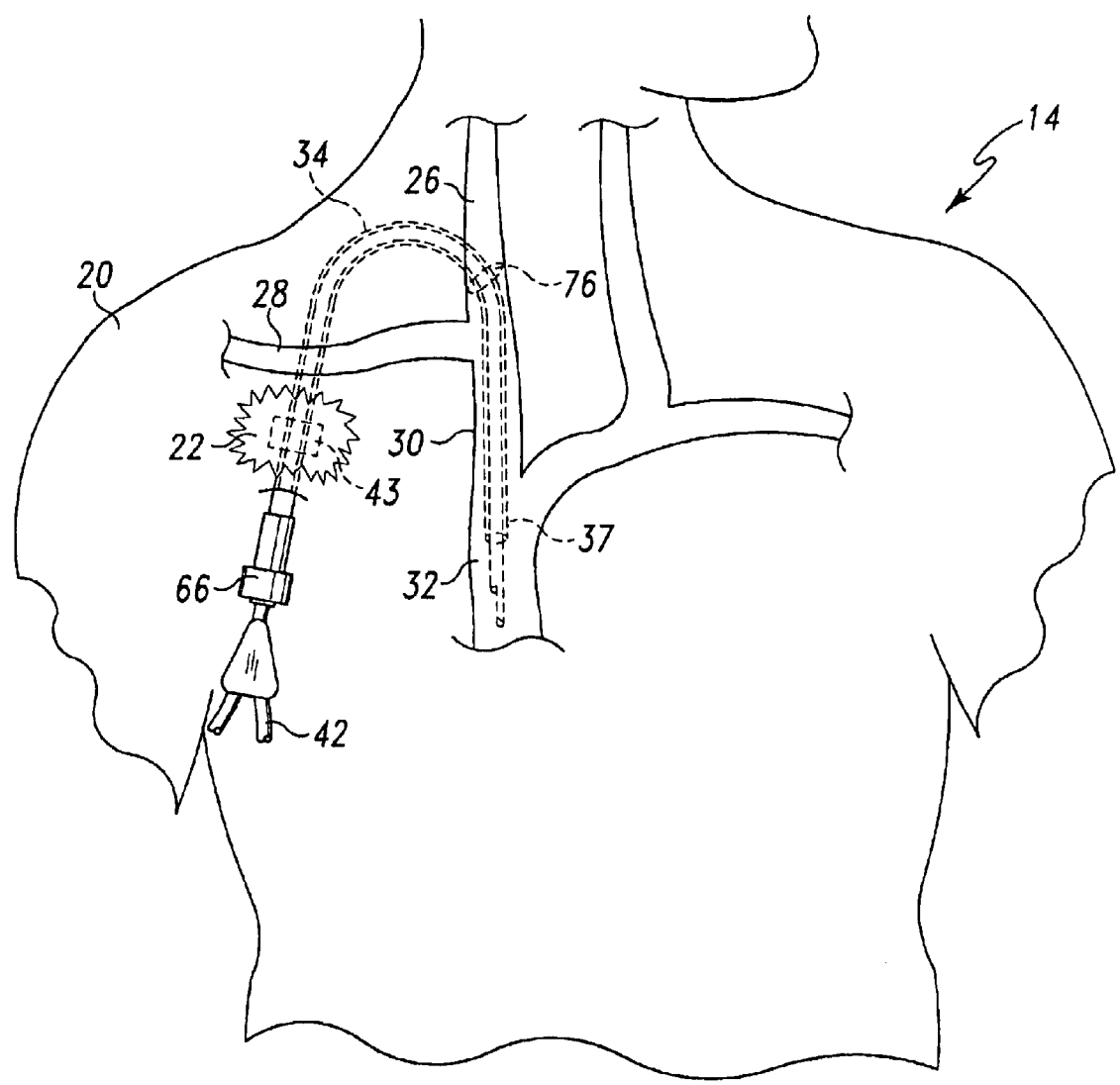
FIG. 9 is an enlarged view which is similar to FIG. 2, but showing the catheter system of FIG. 1 (i) extending from the right upper chest, (ii) tunneled under the skin within the subcutaneous tissue of the patient for a distance, (iii) entering a venotomy in the right internal jugular vein, and (iv) passing caudally in the right internal jugular vein, the right innominate vein and the superior vena cava.

Referring now to FIG. 1, there is shown a hemodialysis machine 10 to which is attached a long-term catheter system 12 which incorporates the features of the present invention therein. The catheter system 12 is inserted in a patient's body 14. The hemodialysis machine 10 includes an inlet line 16 and an outlet line 18 which are each in fluid communication with the catheter system 12. The body 14 includes skin, generally indicated by the reference numeral 20. The body 14 further includes subcutaneous tissue 22 positioned below the skin 20 (see e.g. FIG. 9).

Figure 2:
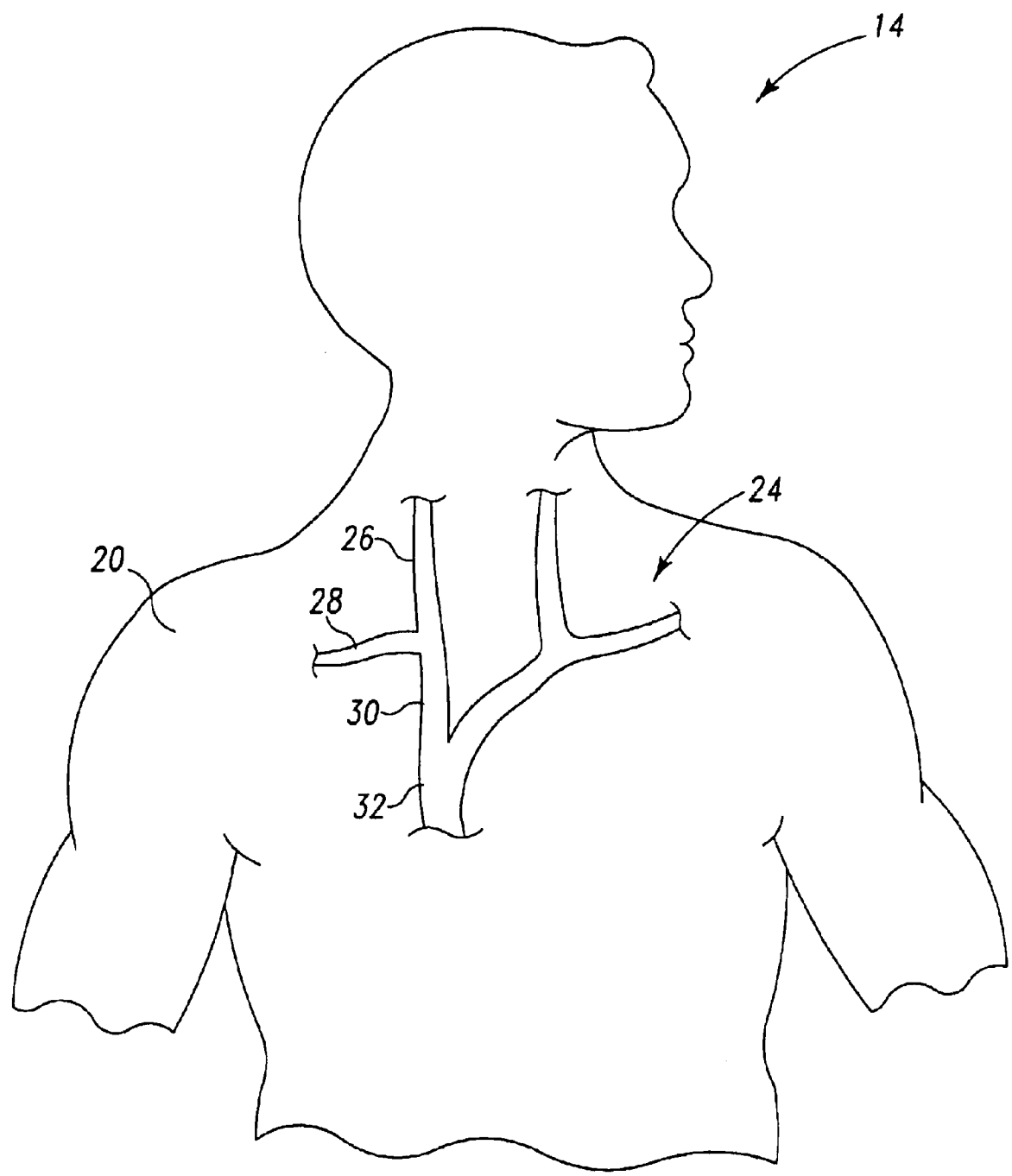
FIG. 2 is a schematic view of a portion of the vascular system of the patient of FIG. 1, showing the right internal jugular vein, the right subclavian vein, the right innominate vein, and the superior vena cava.

As shown in FIG. 2, the body 14 further includes a vascular system 24. The vascular system 24 includes a right internal jugular vein 26, a right subclavian vein 28, a right innominate vein 30, and a superior vena cava 32. Note that the vascular system 24 is positioned within the body 14 underneath the skin 20. However, the vascular system 24, including the right internal jugular vein 26, the right subclavian vein 28, the right innominate vein 30, and the superior vena cava 32, are depicted in FIGS. 2, 9–11, 23, and 26 with solid lines for clarity of description.

Figure 3:
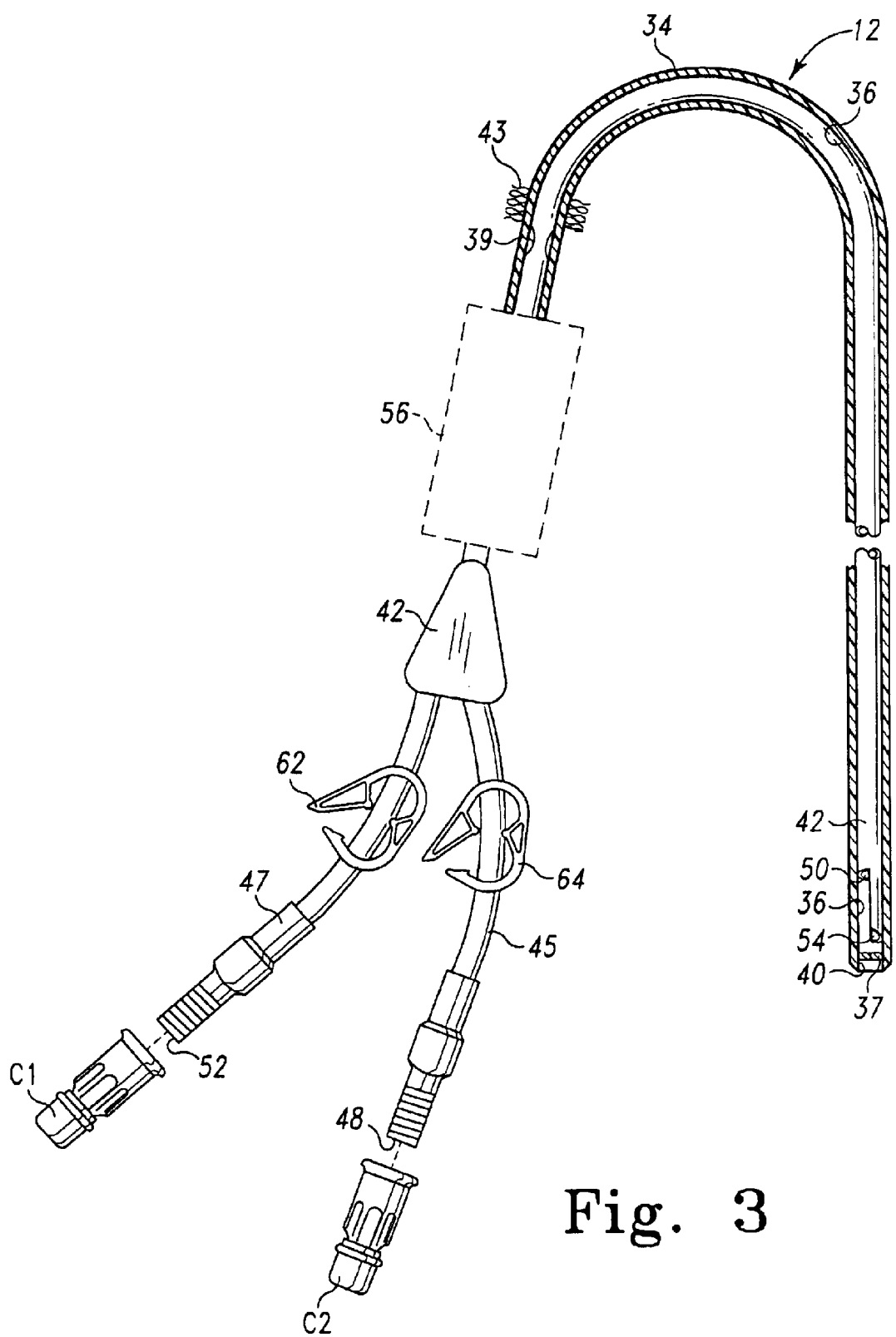
FIG. 3 is an enlarged side elevational view of the catheter system of FIG. 1, showing the working catheter positioned within the guide lumen of the guide catheter, and further schematically showing the locking mechanism which is configured to lock the working catheter relative to the guide catheter in any one of a plurality of positions (note that FIG. 3 shows the locking mechanism operating to lock the working catheter in the stowed position)

The catheter system 12 is shown in more detail in FIG. 3. In particular, the catheter system includes a guide catheter 34 having a central guide lumen 36 which extends the entire length thereof (see also FIGS. 6A–6D). The guide lumen 36 defines a proximal guide orifice 38 and a distal guide orifice 40.

A distal valve 37 is secured to the guide catheter 34 at a location within the guide lumen 36 substantially adjacent to the distal guide orifice 40 (see e.g. FIGS. 3–5, 6A and 6C). The distal valve 37 is configured to inhibit fluid from advancing through the distal guide orifice 40 and past the distal valve 37 within the guide lumen 36 of the guide catheter 34. A proximal valve 39 is also secured to the guide catheter 34 at a location within the guide lumen 36 (see also FIGS. 6A, 6B, and 8). The proximal valve 39 is configured to inhibit fluid from advancing within the guide lumen 36 from one side of the proximal valve 39 to the other side of the proximal valve 39. The valves 37, 39 also function to inhibit air flow leakage though the guide lumen 36 of the guide catheter 34. One valve which may be used as either the distal valve 37 or the proximal valve 39 with some modifications is available from Micro Therapeutics, Inc. of San Clemente, Calif. under the trademark "Cragg MicroValve™".

Figure 8:
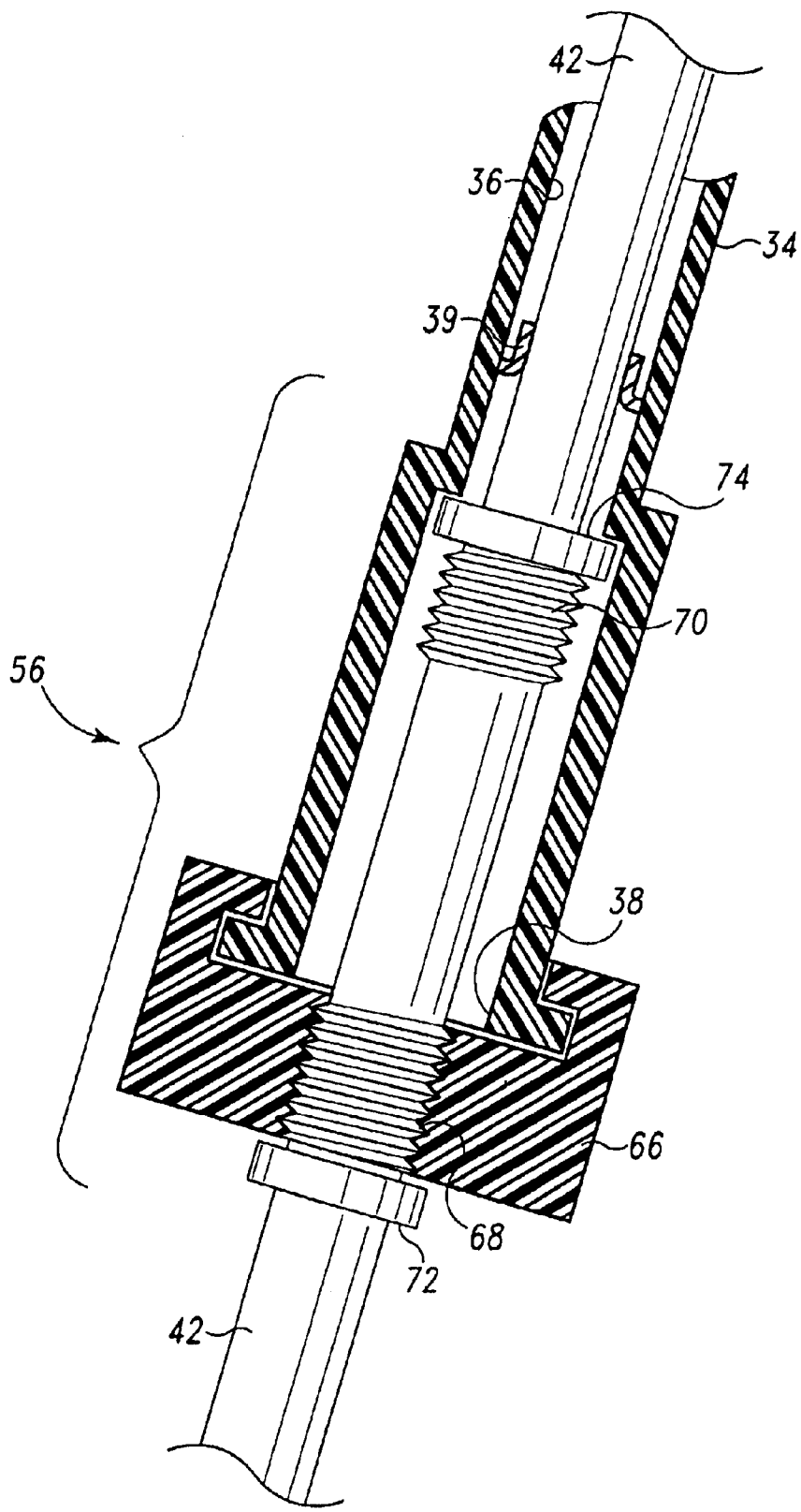
FIG. 8 is an enlarged view of a portion of FIG. 5 which shows the locking mechanism of FIG. 5 in more detail.
Figure 8A:
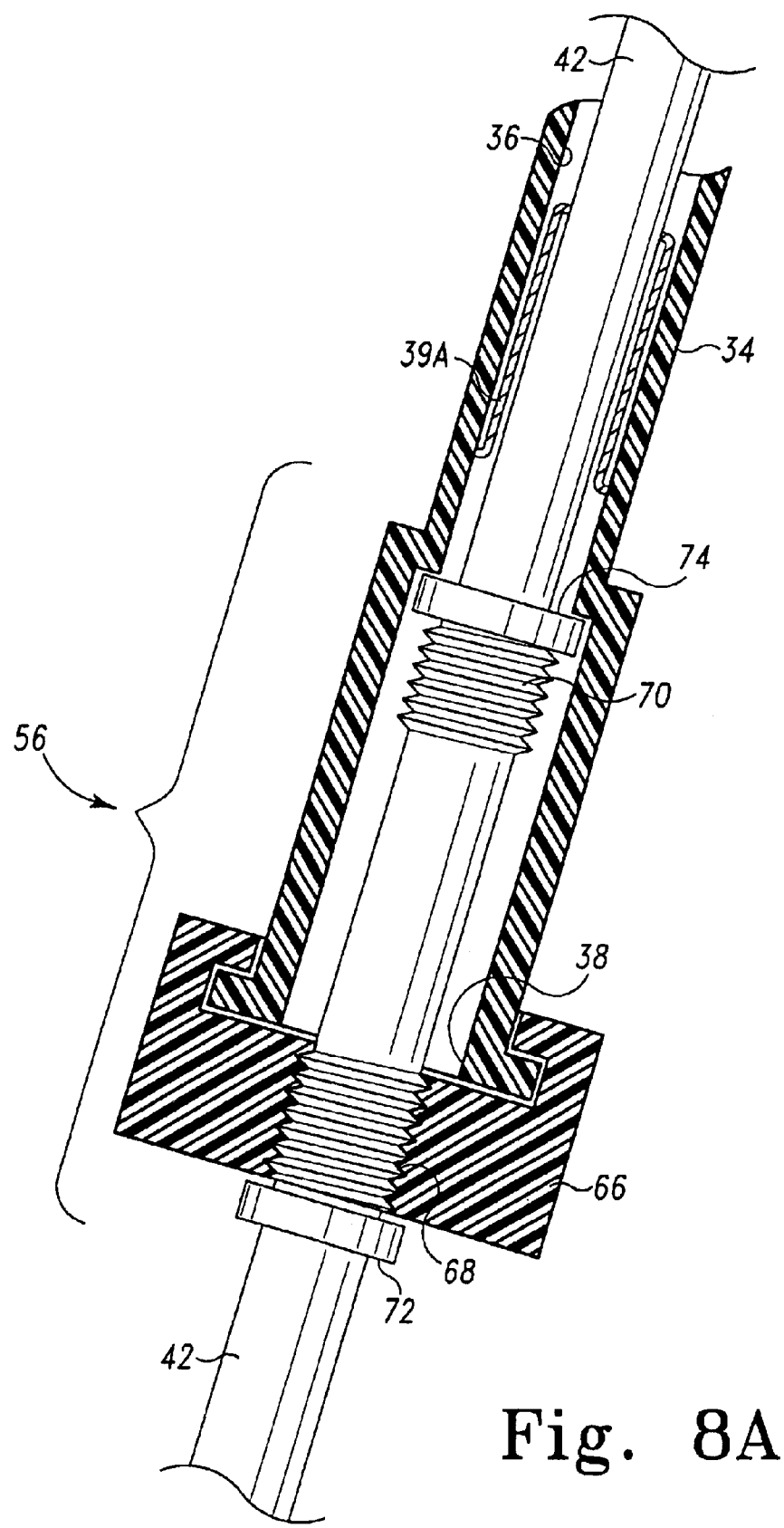
FIG. 8A is also an enlarged view of a portion of FIG. 5 which shows the locking mechanism of FIG. 5 in more detail, however.

Alternatively, a flexible separating diaphragm 39A may be substituted for the proximal valve 39 as shown in FIG. 8A. The separating diaphragm 39A would have a first end thereof secured to the inner surface of the guide catheter 34, and a second end thereof secured to the outer surface of the working catheter 42 as shown in FIG. 8A. The first end of the separating diaphragm 39A would be secured to an entire 360° segment of the inner surface of the guide catheter 34 whereby fluid is completely prevented from advancing between the separating diaphragm 39A and the guide catheter 34. Similarly, the second end of the separating diaphragm 39A would be secured to an entire 360° segment of the outer surface of the working catheter 42 whereby fluid is completely prevented from advancing between the separating diaphragm 39A and the working catheter 42. Accordingly, fluid is completely prevented from advancing within the guide lumen 36 of the guide catheter 34 from one side of the separating diaphragm 39A to the other side of the separating diaphragm 39A. The separating diaphragm 39A also functions to prevent air flow leakage though the guide lumen 36 of the guide catheter 34. The separating diaphragm 39A is made from the same material from which the proximal valve 39 is made.

Referring again to FIGS. 6A–6D, the guide catheter 34 also includes an outer surface 41 having a tissue ingrowth member 43 secured thereto. The tissue ingrowth member 43 is configured to facilitate fibrous tissue growth therein. More specifically, the subcutaneous tissue 22 of the body 14 becomes affixed to the tissue ingrowth member 43 when the tissue ingrowth member 43 remains in contact with the subcutaneous tissue 22 over a period of time. One type of tissue ingrowth member which may be used as the tissue ingrowth member 43 is a DACRON cuff which is available from Bard Access Systems of Salt Lake City, Utah.

The catheter system 12 further includes a working catheter 42 which is positioned within the guide lumen 36 of the guide catheter 34 (see FIGS. 3–5 and 10–11). The working catheter 42 has an ingress lumen 44 through which fluid may be advanced, and an egress lumen 46 also through which fluid may be advanced (see FIGS. 7A–7D). The ingress lumen 44 defines a first distal working orifice 50, while the egress lumen 46 defines a second distal working orifice 54. The first distal working orifice 50 and the second distal working orifice 54 are defined in a distal working segment 55 of the working catheter 42 (see FIGS. 4, 5, and 7A).

The working catheter 42 further includes an ingress line 45 and an egress line 47. The ingress line 45 defines a first proximal working orifice 48, while the egress line 47 defines a second proximal working orifice 52. The ingress line 45 is in fluid communication with the ingress lumen 44, while the egress line 47 is in fluid communication with the egress lumen 46. The egress line 47 has an adapter or injection cap C1 attached thereto, and the ingress line 45 has an adapter or injection cap C2 attached thereto (see FIG. 7A).

Figure 7A:
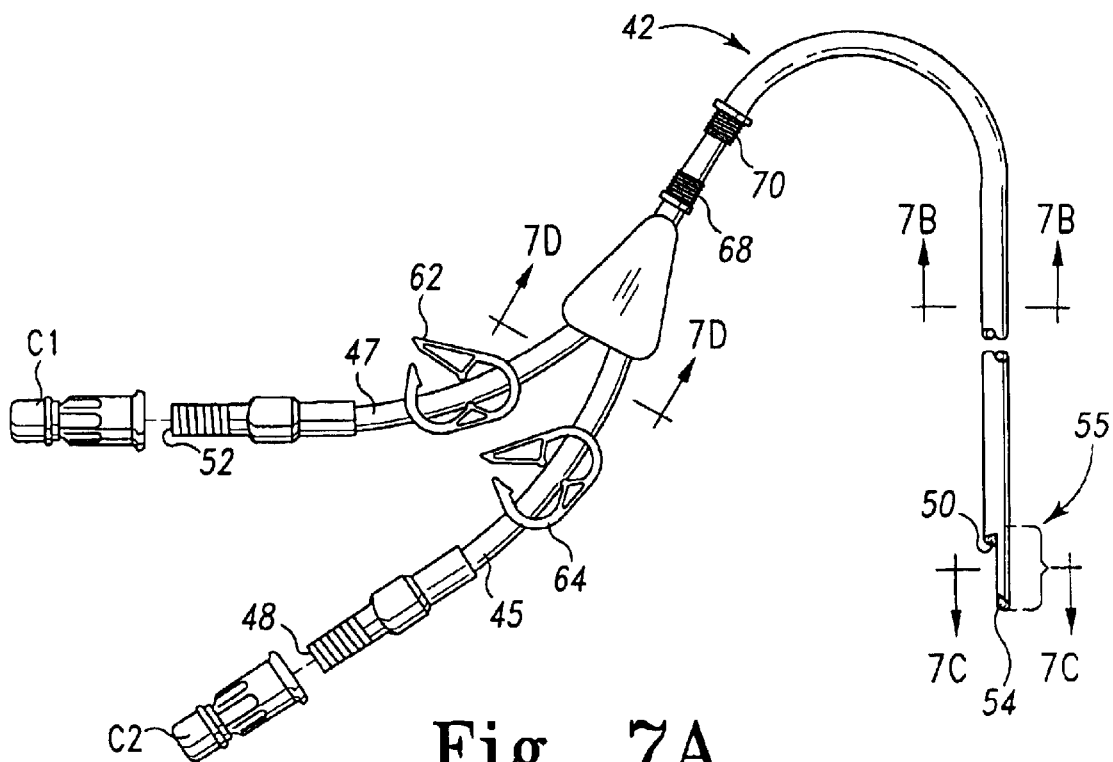
FIG. 7A is an enlarged side elevational view of the working catheter of the catheter system shown in FIG. 1.
Figure 7B:
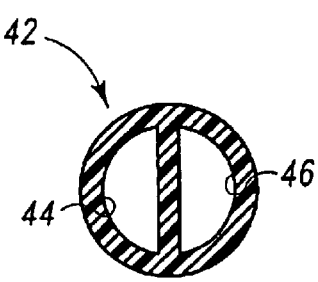
FIG. 7B is an enlarged cross sectional view of the working catheter taken along the line 7B—7B of FIG. 7A as viewed in the direction of the arrows.
Figure 7C:
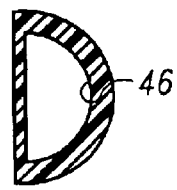
FIG. 7C is an enlarged cross sectional view of the working catheter taken along the line 7C—7C of FIG. 7A as viewed in the direction of the arrows.
Figure 7D:
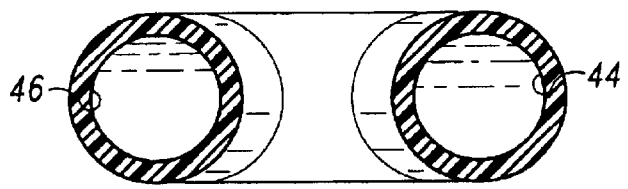
FIG. 7D is an enlarged cross sectional view of the working catheter taken along the line 7D—7D of FIG. 7A as viewed in the direction of the arrows.

In addition, a clamp 62 is positioned on the egress line 47, while a clamp 64 is positioned on the ingress line 45 as shown in FIG. 7A. It should be understood that closure of the clamp 64 causes fluid communication between the first proximal working orifice 48 and the first distal working orifice 50 to be prevented. Similarly, closure of the clamp 62 prevents fluid communication between the second proximal working orifice 52 and the second distal working orifice 54.

The catheter system 12 additionally includes a locking mechanism 56 which is schematically shown in FIG. 3. The locking mechanism 56 operates to lock the working catheter 42 in relation to the guide catheter 34 at any one of two positions. In particular, the locking mechanism 56 may lock the working catheter 42 relative to the guide catheter 34 in an operative position (see e.g. FIGS. 5, 9, and 11) or in a stowed position (see e.g. FIGS. 3, 4 and 10). It should be noted that when the working catheter 42 is locked in the operative position, (i) the working catheter 42 extends through the guide lumen 36 of the guide catheter 34 and out of the distal guide orifice 40 of the guide catheter 34, and (ii) the first distal working orifice 50 and the second distal working orifice 54 are each positioned outside of the guide catheter 34. On the other hand, when the working catheter 42 is locked in the stowed position, (i) the working catheter 42 extends into the guide lumen 36 of the guide catheter 34, and (ii) the first distal working orifice 50 and the second distal working orifice 54 are each positioned within the guide lumen 36 of the guide catheter 34.

One type of locking mechanism which may be used as the locking mechanism 56 of the present invention is shown in more detail in FIGS. 4, 5, 6A, 6B, 7A, and 8. Reference number 56 will also be used to identify this locking mechanism. In particular, the locking mechanism 56 includes an internally threaded member 66. The internally threaded member 66 is attached to the guide catheter 34 in a manner which allows the internally threaded member to rotate relative to the guide catheter 34 (see FIGS. 6B and 8).

Figure 4:
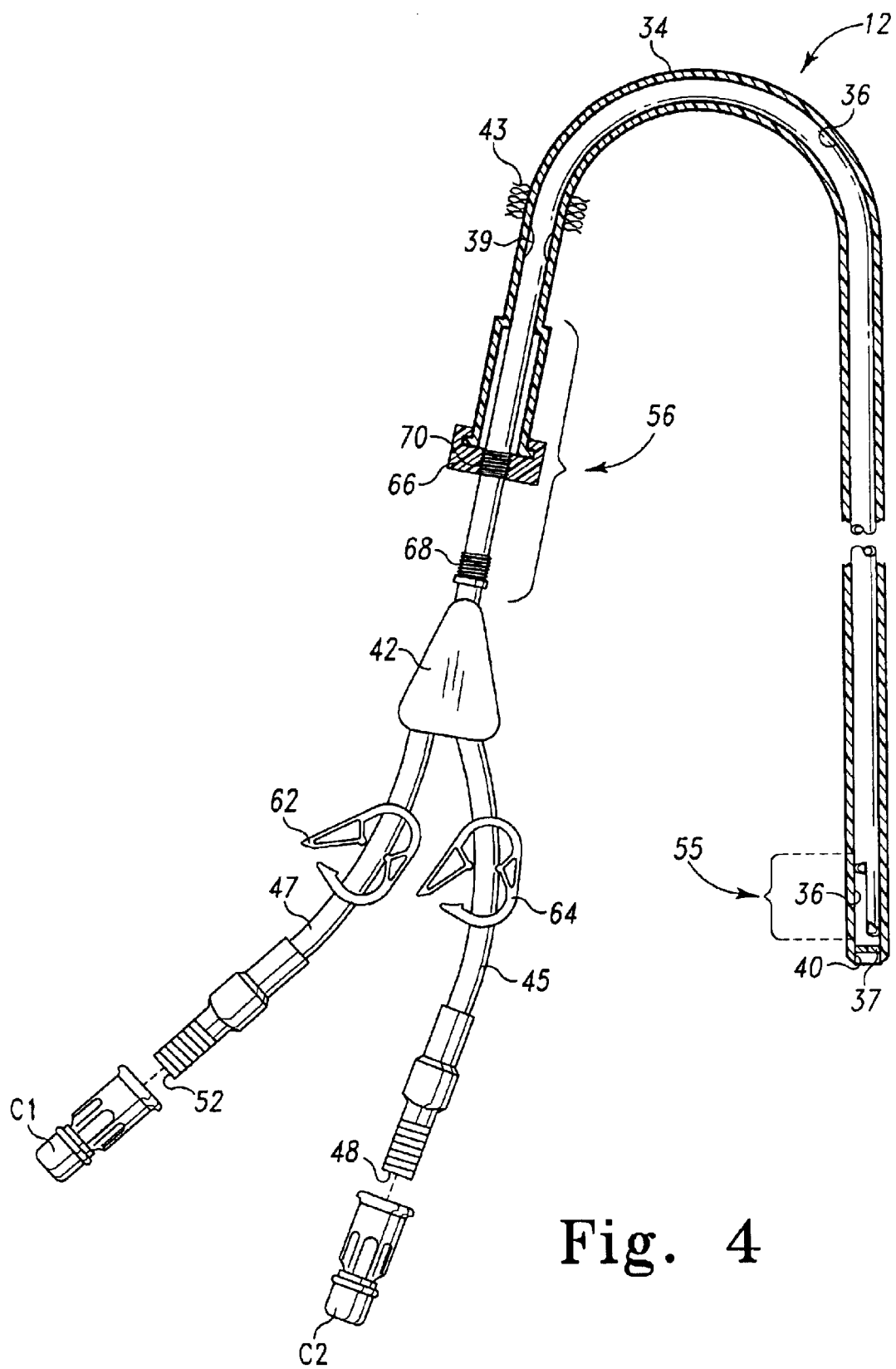
FIG. 4 is a view similar to FIG. 3 but showing one example of a locking mechanism which can be used in the present invention (note that FIG. 4 shows the locking mechanism operating to lock the working catheter in the stowed position)
Figure 5:
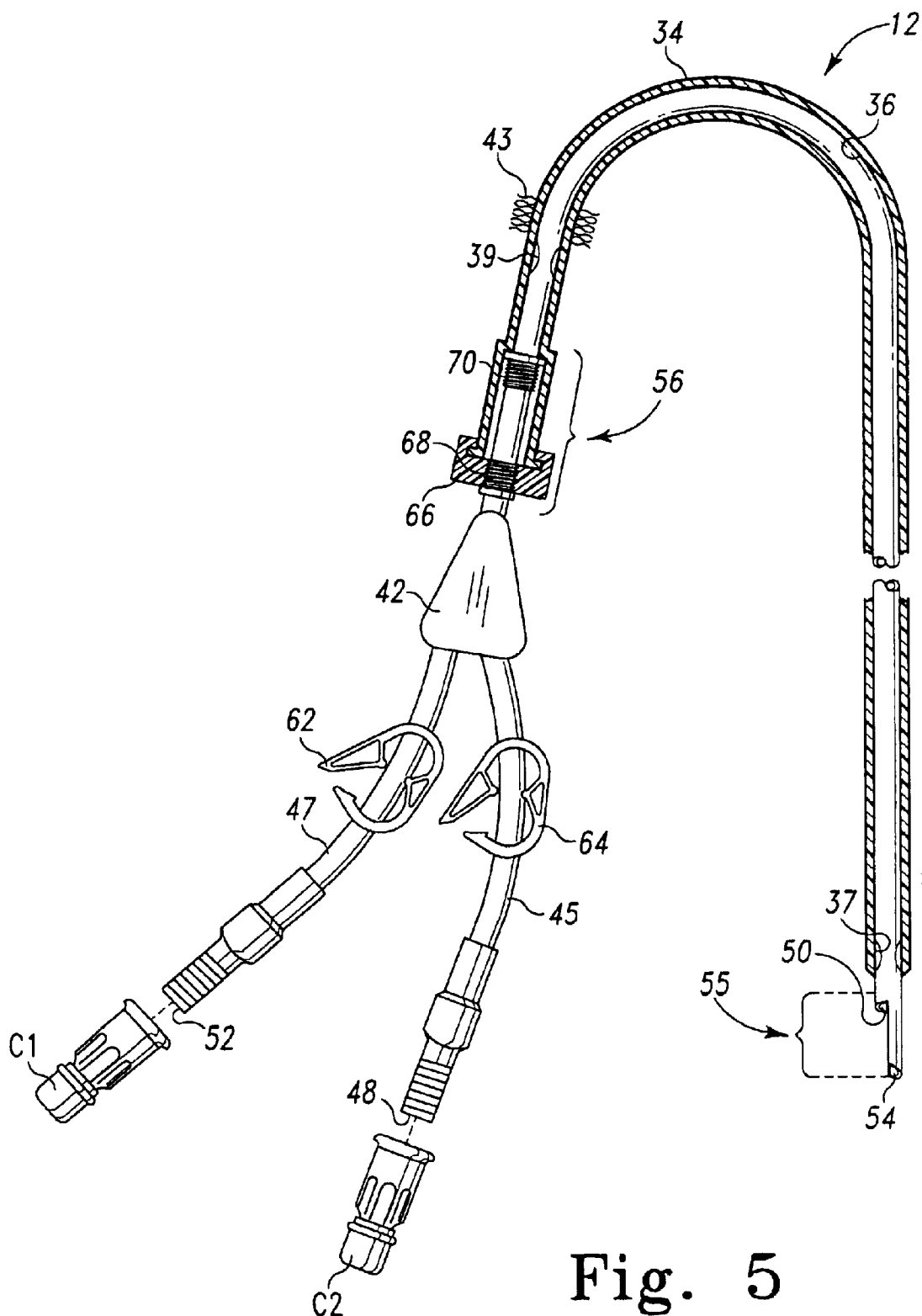
FIG. 5 is a view similar to FIG. 4 but showing the locking mechanism operating to lock the working catheter in the operative position.
Figure 6A:
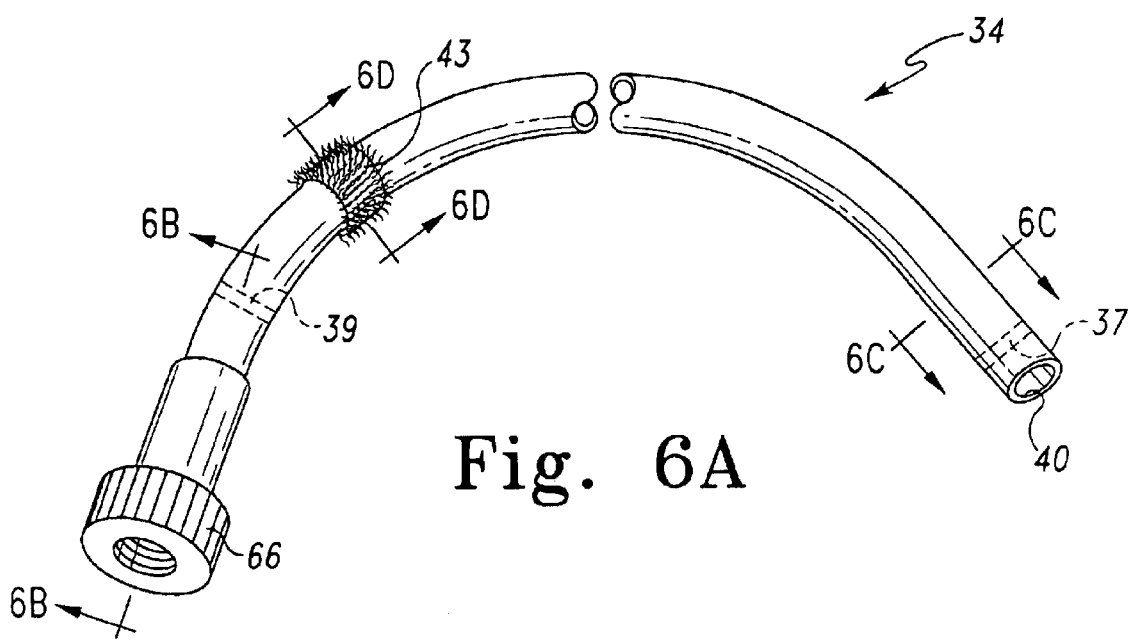
FIG. 6A is an enlarged side elevational view of the guide catheter of the catheter system shown in FIG. 1.
Figure 6B:
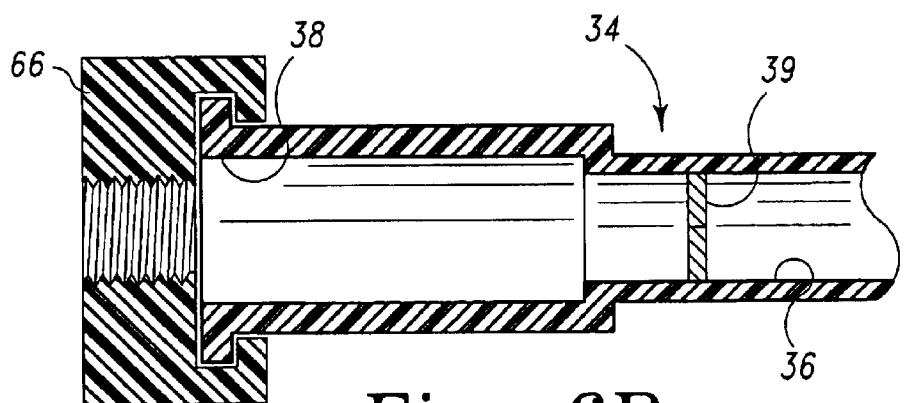
FIG. 6B is an enlarged fragmentary cross sectional view of the guide catheter taken along the line 6B—6B of FIG. 6A as viewed in the direction of the arrows.
Figure 6C:
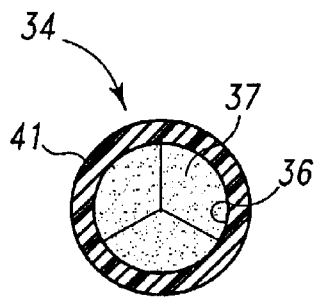
FIG. 6C is an enlarged cross sectional view of the guide catheter taken along the line 6C—6C of FIG. 6A as viewed in the direction of the arrows.
Figure 6D:
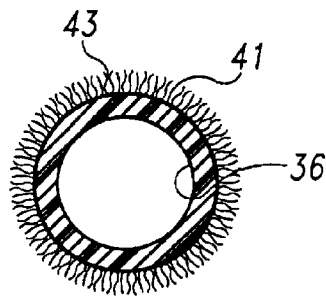
FIG. 6D is an enlarged cross sectional view of the guide catheter taken along the line 6D—6D of FIG. 6A as viewed in the direction of the arrows.

The locking mechanism 56 further includes a first set of external threads 68 and a second set of external threads 70 which are each defined in an exterior surface of the working catheter 42. As shown in FIG. 8, the first set of external threads 68 is spaced apart from the second set of external threads 70. The internally threaded member 66 meshes with the first set of external threads 68 so as to lock the working catheter 42 in the operative position as shown in FIG. 5. Similarly, the internally threaded member 66 meshes with the second set of external threads 70 so as to lock the working catheter 42 in the stowed position as shown in FIG. 4.

As further shown in FIG. 8, a proximal stop 72 is provided to limit proximal movement of the internally threaded member 66 relative to the working catheter 42. Similarly, a distal stop 74 is provided to limit distal movement of the internally threaded member 66 relative to the working catheter 42.

While the locking mechanism 56 which is particularly shown in FIGS. 4, 5, 6A, 6B, 7A, and 8 as possessing cooperating internal and external threads, and has substantial benefits, numerous other types of locking mechanisms may be used as the locking mechanism 56 (see FIG. 3) and still achieve many of the advantages of the present invention.

For example, another locking mechanism which may be used as the locking mechanism 56 (see FIG. 3) is a detent and groove type locking mechanism (not shown). In particular, such a locking mechanism would include a first groove and a second groove which are (i) spaced apart from each other, and (ii) each defined in an outer surface of the working catheter 42 (the sidewall of the working catheter may need to possess an increased thickness in order to define such grooves therein). A detent (e.g. a ball), supported by the guide catheter 34, may be spring biased into the first groove so as to lock the working catheter 42 in relation to the guide catheter 34 thereby locking the working catheter 42 in the operative position. When desired, the detent may be allowed to advance out of the first groove and into the second groove. Thereafter, the detent may be spring biased into the second groove so as to lock the working catheter 42 in relation to the guide catheter 34 thereby locking the working catheter 42 in the stowed position. Examples of detent and groove type locking mechanisms which may be used with some modifications as the locking mechanism 56 of the present invention are disclosed in U.S. Pat. Nos. 4,900,202 and 5,013,194 each issued to Wienhold, and U.S. Pat. Nos. 5,470,180 and 5,779,404 each issued to Jore.

Yet another example of a locking mechanism which may be used as the locking mechanism 56 (see FIG. 3) is a leg and guide channel type locking mechanism (not shown). In particular, such a locking mechanism would include a short leg extending from an outer surface of the working catheter 42. The leg would be fixed in relation to the working catheter 42. The locking mechanism would further include a guide channel defined in a sidewall of the guide catheter 34. The guide channel would extend longitudinally for a short distance (e.g. a few centimeters) along the length of the guide catheter 34. At the proximal end of the guide channel, there would exist a narrowed proximal channel portion of reduced width. Similarly, at the distal end of the guide channel, there would exist a narrowed distal channel portion of reduced width. In operation, the leg would be positioned in the guide channel. If it would be desirable to lock the working catheter 42 in relation to the guide catheter 34 so as to lock the working catheter 42 in the operative position, the working catheter 42 could be advanced distally in relation to the guide catheter 34 until the leg became wedged within the narrowed distal channel portion. A secondary safety latch may be employed to retain the leg in the narrowed distal channel portion. On the other hand, if it would be desirable to lock the working catheter 42 in relation to the guide catheter 34 so as to lock the working catheter 42 in the stowed position, the working catheter 42 could be advanced proximally in relation to the guide catheter 34 until the leg became wedged within the narrowed proximal channel portion. Similarly, another secondary safety latch may be employed to retain the leg in the narrowed proximal channel portion.

I(a). Placement of the Catheter System 12 Within the Body

The catheter system 12 is placed within the body 14 using the tunneled catheter technique. In particular, a first opening is created by making a small incision in the skin 20 with a scalpel directly over the right internal jugular vein 26. Thereafter, the right internal jugular vein 26 is punctured to create a venotomy 76 (see FIGS. 9–11) at a location directly below the first opening by advancing a needle through the skin incision and the subcutaneous tissue 22 and into the right internal jugular vein 26. Thereafter, a guidewire is advanced through the needle into the right internal jugular vein 26 through the venotomy 76. The needle is then removed over the guidewire. One or more tubular vessel dilators is passed over the guidewire to widen the opening defined in the skin 20 and subcutaneous tissue 22, and further to widen the venotomy 76 defined in the wall of the right internal jugular vein 26 to a caliber similar to that of a tubular guide. Thereafter, the tubular guide is advanced over the guidewire and into the right internal jugular vein 26. Then, a second opening is created in the skin 20 which is spaced apart at least several centimeters from the first opening. A tunneling instrument is advanced from the second opening to the first opening so as to create a passageway within the subcutaneous tissue 22 under the skin 20 between the first opening and the second opening. The catheter system 12 is then advanced into the second opening and through the passageway such that the distal guide orifice 40 of the guide catheter 34 is located adjacent to the first opening. Note that during the above-described advancement of the catheter system 12, the working catheter 42 is locked to the guide catheter 34 in the stowed position (see e.g. FIG. 4).

The distal end of the catheter system 12 is then inserted through the tubular guide member and into the right internal jugular vein 26 so that the tissue ingrowth member 43 is positioned in the subcutaneous tissue 22. Thereafter, the tubular guide member is removed. The first opening is then closed with suture whereby the catheter system 12: (a) is no longer exposed through the first opening, (b) extends for at least several centimeters under the skin 20 between the second opening and the venotomy 76, and (c) extends out of the second opening so that the proximal end of the catheter system 12 is located outside of the body 14 as shown in FIG. 10.

Figure 10:
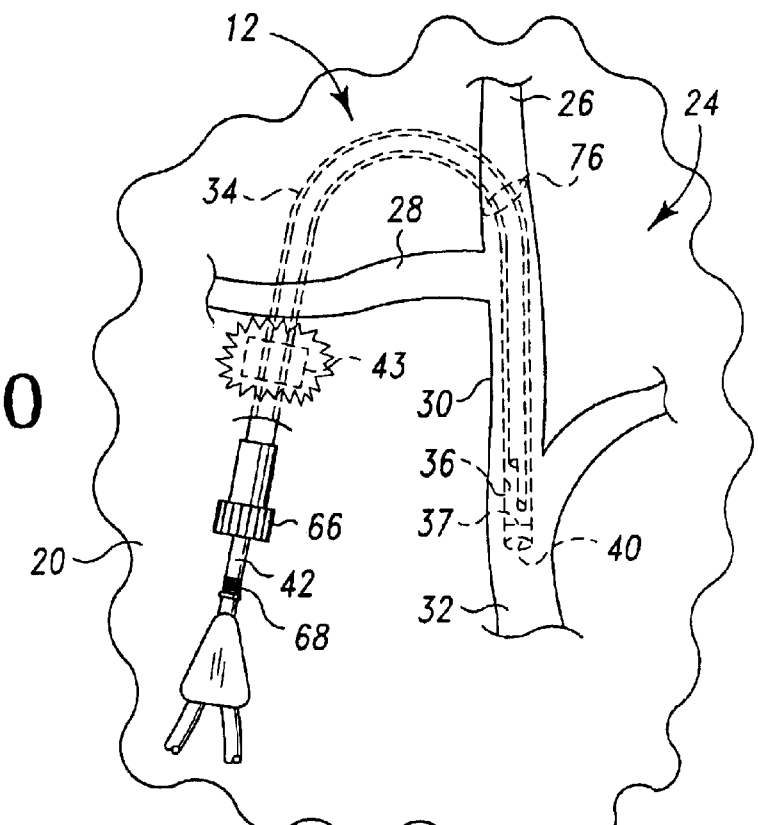
FIG. 10 is a fragmentary enlarged view which is similar to FIG. 9, but showing the working catheter locked to the guide catheter in the stowed position.

Note that after the catheter system 12 is placed in the vascular system 24 as described above, the catheter system 12 is positioned in the right internal jugular vein 26, the right innominate vein 30, and the superior vena cava 32 as shown in FIG. 10. Moreover, note that as the tissue ingrowth member 43 remains in contact with the subcutaneous tissue 22 over a period of time, the subcutaneous tissue 22 becomes affixed to the tissue ingrowth member 43 thereby securing the catheter system 12 to the body 14. As discussed above, affixation of the tissue ingrowth member 43 to the subcutaneous tissue 22 in the above described manner helps prevent bacterial migration up the catheter system 12 from the second opening to the venotomy 76 thereby preventing serious infection.

1(b). Performance of a Dialysis Session with the Catheter System 12

Once the catheter system 12 is placed in the body 14 as described above, the catheter system is positioned as shown in FIG. 10. In this position, the working catheter 42 is locked in the stowed position. When a patient desires to be dialyzed (i.e. engage in a dialysis session), the egress line 47 and the ingress line 45 are respectively connected to the inlet line 16 and the outlet line 18 of the hemodialysis machine 10 as shown in FIG. 1.

Figure 11:
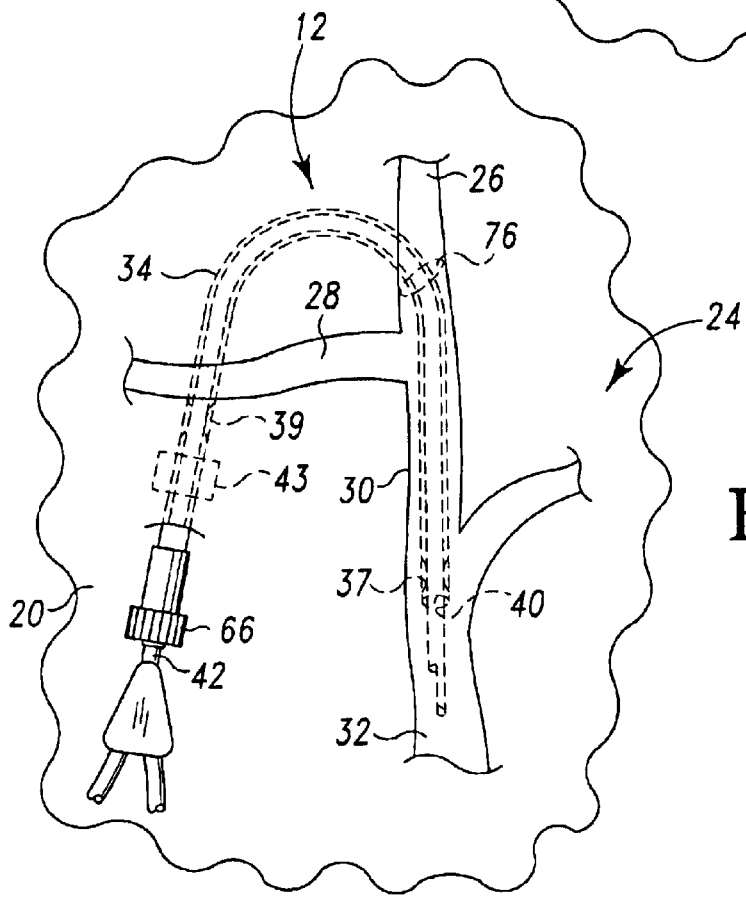
FIG. 11 is a view similar to FIG. 10, but showing the working catheter locked to the guide catheter in the operative position.

Thereafter, the working catheter 42 is unlocked from the guide catheter 34 by rotating the internally threaded member 66 so as to unscrew the internally threaded member 66 out of meshing engagement with the second set of external threads 70 which are defined in the exterior surface of the working catheter 42. The working catheter 42 is then advanced in a distal direction relative to the guide catheter 34 thereby exposing the distal working segment 55 of the working catheter 42 to the blood flow within the superior vena cava 32. Thereafter, the working catheter 42 is locked to the guide catheter 34 in the operative position as shown in FIG. 11. In particular, the internally threaded member 66 is rotated so as to screw the internally threaded member 66 into meshing engagement with the first set of external threads 68 which are defined in the exterior surface of the working catheter 42.

Moving the working catheter 42 from its stowed position (FIG. 10) to its operative position (FIG. 11), causes the first distal working orifice 50 and the second distal working orifice 54 to be exposed to the blood flow within the superior vena cava 32. With the working catheter 42 locked in the operative position, a dialysis procedure is then performed on the patient's body 14 in a well known manner.

Upon completion of the dialysis procedure, the working catheter 42 is unlocked from the guide catheter 34 by rotating the internally threaded member 66 so as to unscrew the internally threaded member 66 out of meshing engagement with the first set of external threads 68. The working catheter 42 is then advanced in a proximal direction relative to the guide catheter 34 thereby withdrawing the distal working segment 55 of the working catheter 42 out of contact with the blood flow in the superior vena cava 32 and into the guide lumen 36 of the guide catheter. Thereafter, the working catheter 42 is locked to the guide catheter 34 in the stowed position thereby assuming the position as shown in FIG. 10. In particular, the internally threaded member 66 is rotated so as to screw the internally threaded member 66 into meshing engagement with the second set of external threads 70.

After the working catheter 42 is locked in its stowed position, the egress line 47 and ingress line 45 are respectively disconnected from the inlet line 16 and the outlet line 18. The proximal orifices 48 and 52 are then each covered with any suitable device (e.g. adapters or injection caps C1, C2), and the patient is able to carry on about his/her business. Thereafter, when a patient desires to be dialyzed again, the above procedure is repeated.

With the catheter system 12 of the present invention, it should be appreciated that the length of time which the distal orifices 50, 54 of the working catheter 42 are exposed to the blood flow in the superior vena cava 32 is substantially reduced relative to the length of time which the corresponding distal orifices of conventional hemodialysis catheters are exposed. This reduction in blood flow exposure time substantially reduces the likelihood that the distal orifices 50, 54 will become partially or totally occluded due to attachment or build-up of blood clots, such as fibrin, on the outer and inner surfaces of the distal working segment 55 of the working catheter 42.

In order to further reduce the likelihood that the distal orifices 50, 54 will become partially or totally occluded due to blood clot attachment or build-up, a quantity of blood clot dissolving liquid may be advanced into the catheter system 12 after a dialysis session is completed in order to flush the fluid flow paths of the working catheter 42 and create a pool in which the distal working segment 55 of the working catheter 42 may be bathed. In particular, after the egress line 47 and ingress line 45 are respectively disconnected from the inlet line 16 and the outlet line 18 following completion of dialysis session, a quantity of blood clot dissolving liquid may be advanced into the egress line 47 and/or the ingress line 45. Advancement of the blood clot dissolving liquid into the egress line 47 causes flushing of the following portions of the working catheter 42: (i) the second proximal working orifice 52, (ii) the egress line 47, (iii) the egress lumen 46, and (iv) the second distal working orifice 54. Similarly, advancement of the blood clot dissolving liquid into the ingress line 45 causes flushing of the following portions of the working catheter 42: (i) the first proximal working orifice 48, (ii) the ingress line 45, (iii) the ingress lumen 44, and (iv) the first distal working orifice 50. Advancement of the blood clot dissolving liquid into the catheter system 12 may be continued until substantially all of the blood is removed from (i) the working catheter 42, and (ii) the guide lumen 36 of the guide catheter 34. This may require an amount of the blood clot dissolving liquid to be advanced past the distal valve 37 and out of the distal orifice 40 of the guide catheter 34. Advancement of the blood clot dissolving liquid into the catheter system 12 in the above-described manner causes an amount of the blood clot dissolving liquid to become trapped or pooled within the guide lumen 36 of the guide catheter 34 at a location which is proximal to the distal valve 37 and distal to the proximal valve 39. While the blood clot dissolving liquid is pooled within the guide lumen 36 of the guide catheter 34 at the above-described location, the blood clot dissolving liquid contacts the working catheter 42 at the first distal working opening 50 and the second distal working opening 54. This advantageously helps prevent total or even partial occlusion of the orifices 50, 54 due to blood clot build-up. One type of blood clot dissolving liquid which may be used with the present invention is urokinase.

After the blood clot dissolving liquid is advanced into the catheter system 12 in the above-described manner, then the proximal orifices 48 and 52 are each sealed with any suitable device (e.g. adapters or injection caps C1, C2), and subsequently the patient is able to carry on about his/her business. The above flushing procedure may be repeated after each dialysis session is completed.

While advancement of the blood clot dissolving liquid (such as urokinase) into the guide lumen 36 of the guide catheter 34 after a dialysis session has been completed has many advantages, some advantages may also be achieved by advancement of an alternative solution into the catheter system 12 after a dialysis session. For example, instead of advancing blood clot dissolving liquid (such as urokinase) into the catheter system 12 after a dialysis session, a heparin lock flush solution may be advanced into the catheter system 12 after a dialysis session has been completed in order to flush the fluid flow paths of the working catheter 42 and create a pool in which the distal working segment 55 of the working catheter 42 may be bathed.

It should be noted that while the distal valve 37 helps maintain the flushing solution (e.g. urokinase or heparin) within the guide lumen 36 of the guide catheter 34 of the catheter system 12 during idle periods when the working catheter is positioned in the stowed position, the distal valve 37 also helps prevent blood which is flowing in the superior vena cava flow from advancing into contact with the distal orifices 50, 54 of the working catheter 42 of the catheter system 12 during idle periods when the working catheter is positioned in the stowed position.

It should further be understood that the distal valve 37 and the proximal valve 39 help prevent blood from escaping through the catheter system 12 during idle periods (i.e. after completion of a dialysis session and before commencement of a subsequent dialysis session). It should also be appreciated that during a dialysis session, the valves 37 and 39 function to prevent blood and/or air leakage through a space defined between the outer surface of the working catheter 42 and the inner surface of the guide catheter 34.

Please note that the working catheter 42 of the catheter system 12 contacts the blood located in the vascular system 24 for a substantially reduced amount of time (i.e. only while the patient is undergoing dialysis) in comparison to the amount of time a conventional dialysis catheter is being contacted by blood located in the vascular system (i.e. at all times). Accordingly, the physical structure of the working catheter 42 may be substantially the same or similar to the physical structure of a conventional short-term catheter. For example, the thickness of the sidewalls of the working catheter 42 which define the ingress lumen 44 and the egress lumen 46 may be made to be substantially thinner than the thickness of the sidewalls which define the corresponding lumens of a conventional long-term dialysis catheter. This may help reduce the necessary magnitude of the outer diameter of the guide catheter 34 in which the working catheter 42 is positionable.

II. Catheter System 200

Figures 12, 13:
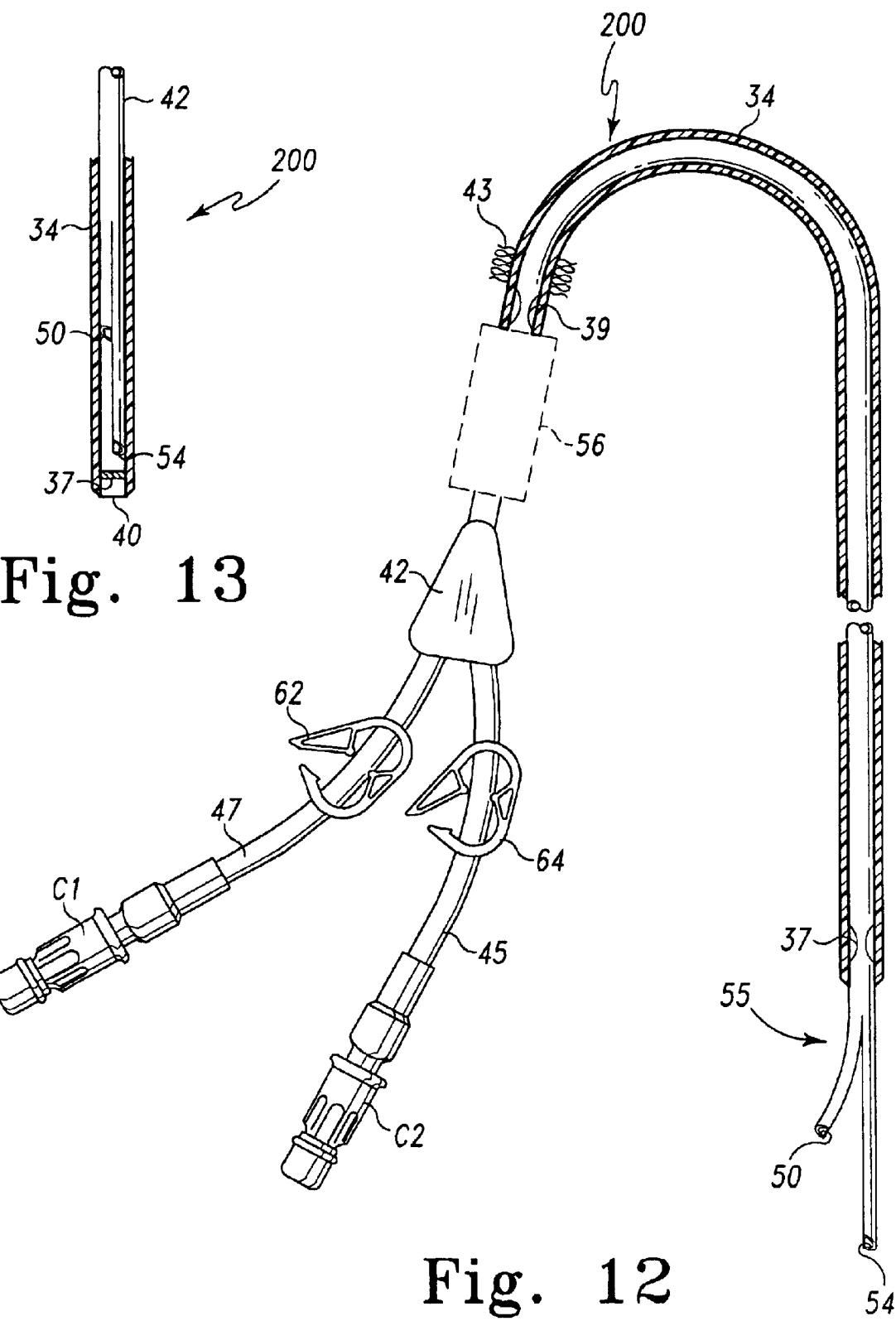
FIG. 12 is a view similar to FIG. 3, but showing another catheter system which incorporates the features of the present invention therein, with the working catheter shown positioned in the operative position.
FIG. 13 is a fragmentary cross sectional view of a distal portion of the catheter system of FIG. 12, but showing the working catheter positioned in the stowed position.

FIGS. 12–13 show a catheter system 200 which also incorporates the features of the present invention therein. The catheter system 200 is somewhat similar to the catheter system 12. Thus, the same reference numerals are used in FIGS. 12–13 to designate common components which were previously discussed with regard to FIGS. 1–11. Moreover, the description of the components of the catheter system 200 which are common to the catheter system 12 will not be undertaken since they are designated with common reference numerals and such components have been previously described hereinabove. In addition, the catheter system 200 is placed within the body 14 in substantially the same manner as was described hereinabove with respect to the placement of the catheter system 12 within the body 14 (i.e. by the tunneled catheter technique). Furthermore, the catheter system 200 is used to perform a dialysis procedure in substantially the same manner as was described hereinabove with respect to the performance of a dialysis procedure with the catheter system 12 (see e.g. Section 1(b) entitled: "Performance of a Dialysis Session with the Catheter System 12").

However, the catheter system 200 differs from the catheter system 12 in that a portion of the distal working segment 55 of the working catheter 42 which extends out of the distal guide orifice 40 of the guide catheter 34 when the working catheter 42 is locked in the operative position is arranged in a bifurcated configuration as shown in FIG. 12. In particular, a distal portion of the ingress lumen 44 (near the first distal working orifice 50) is arranged so as to gradually extend away from a distal portion of the egress lumen 46 (near the second distal working orifice 54) as shown in FIG. 12.

The working catheter 42, shown in FIGS. 12–13, possesses a distal portion configured somewhat similar to the distal portion of a dialysis catheter disclosed in an article entitled "Management of Hemodialysis Catheters" which was published in the July, 1999 edition of the periodical entitled "Applied Radiology" at pages 14–24 (authored by Haskel et al.), the disclosure of which is hereby incorporated by reference. Catheters having a distal portion configured in the above-described manner are sometimes referred to in the relevant medical art as "split-tip" catheters. For example, on page 20 of the Haskel article, a "split-tip" catheter is shown in FIG. 8.

The locking mechanism 56 functions to lock the working catheter 42 to the guide catheter 34 in either the stowed position (FIG. 13) or the operative position (FIG. 12). It should be appreciated that FIG. 13 shows the working catheter 42 locked to the guide catheter 34 in the stowed position. While the working catheter 42 is locked in the stowed position in the patient's body 14 between dialysis sessions, the distal orifices 50, 54 of the working catheter 42 are isolated from contact with the blood flow in the superior vena cava 32. FIG. 12 shows the working catheter 42 locked to the guide catheter 34 in the operative position. While the working catheter 42 is locked in the operative position during performance of a dialysis procedure, the distal orifices 50, 54 of the working catheter 42 are positioned within the blood flow in the superior vena cava 32.

Also, please note that the working catheter 42 of the catheter system 200 contacts the blood located in the vascular system 24 for a substantially reduced amount of time in comparison to the amount of time a conventional dialysis catheter is being contacted by blood located in the vascular system. Accordingly, the physical structure of the working catheter 42 of the catheter system 200 may be substantially the same or similar to the physical structure of a conventional short-term catheter for the same reasons hereinabove discussed in regard to the dialysis catheter 42 of the catheter system 12 in section 1(b) entitled "Performance of a Dialysis Session with the Catheter System 12".

III. Catheter System 300

Figures 14, 15:
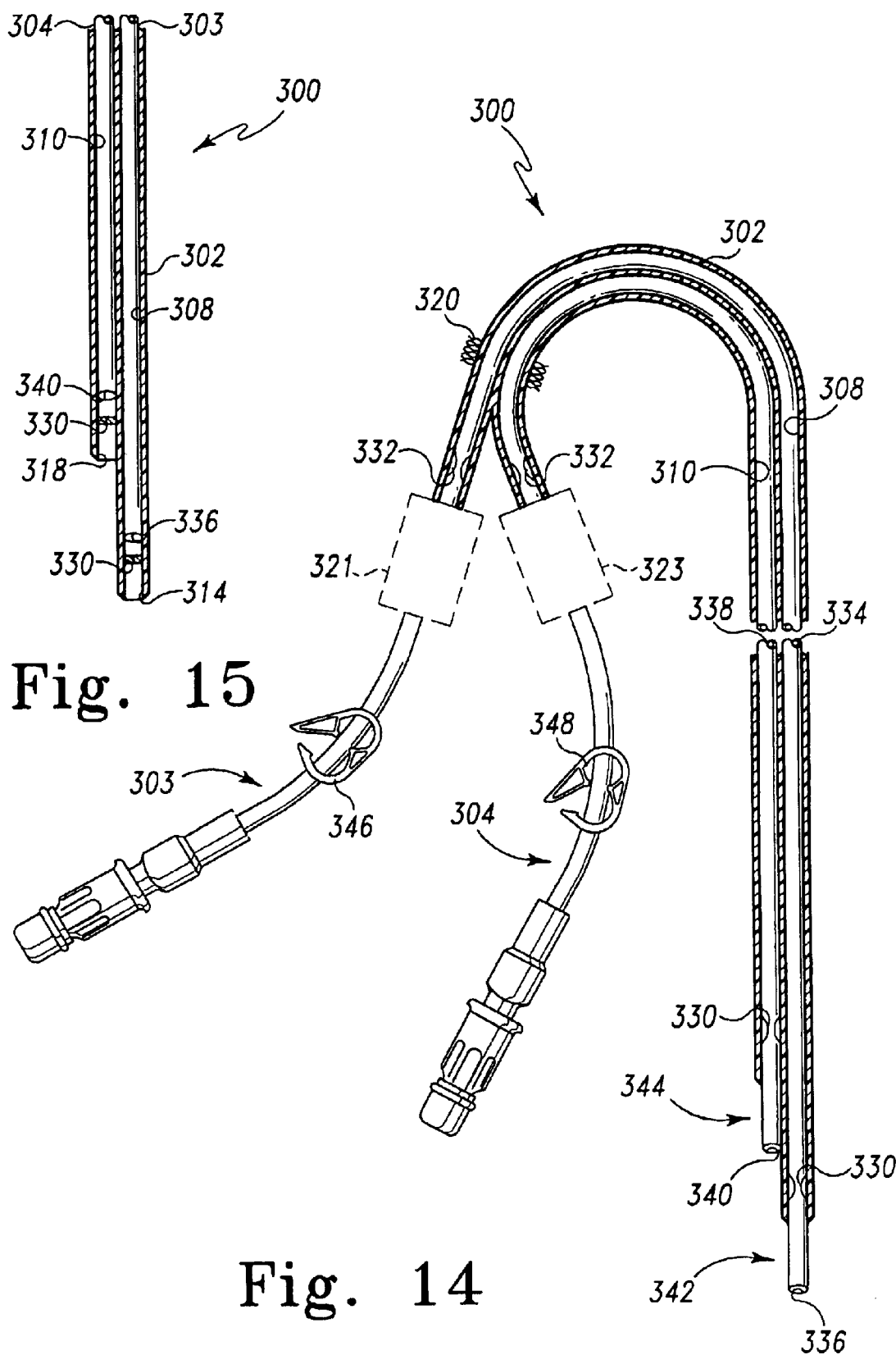
FIG. 14 is a view similar to FIG. 3, but showing yet another catheter system which incorporates the features of the present invention therein, with the working catheters shown positioned in the operative position.
FIG. 15 is a fragmentary cross sectional view of a distal portion of the catheter system of FIG. 14, but showing the working catheters positioned in the stowed position.

FIGS. 14–15 show a catheter system 300 which also incorporates the features of the present invention therein. The catheter system 300 includes a guide catheter 302, a first single lumen working catheter 303, and a second single lumen working catheter 304. The catheter system 300 is placed within the body 14 in substantially the same manner as was described hereinabove with respect to the placement of the catheter system 12 within the body 14 (i.e. by the tunneled catheter technique). Furthermore, the catheter system 300 is used to perform a dialysis procedure in substantially the same manner as was described hereinabove with respect to the performance of a dialysis procedure with the catheter system 12 (see e.g. Section 1 (b) entitled: "Performance of a Dialysis Session with the Catheter System 12").

The guide catheter 302 has a first guide lumen 308 and a second guide lumen 310 each which extends along the length of the guide catheter 302 as shown in FIG. 14. The first guide lumen 308 defines a first distal guide orifice 314, while the second guide lumen 310 defines a second distal guide orifice 318 (see FIG. 15). The first working catheter 303 is positioned within the guide lumen 308 of the guide catheter 302, while the second working catheter 304 is positioned within the guide lumen 310 of the guide catheter 302 as shown in FIGS. 14–15.

The guide catheter 302 has a tissue ingrowth member 320 secured to an outer surface thereof. The tissue ingrowth member 320 is substantially identical to tissue ingrowth member 43 described hereinabove with regard to the catheter system 12.

The first working catheter 303 includes a lumen 334. The lumen 334 defines a distal orifice 336. Similarly, the second working catheter 304 includes a lumen 338. The lumen 338 defines a distal orifice 340. The distal orifice 336 is defined in a distal segment 342 of the first working catheter 303. Similarly, the distal orifice 340 is defined in a distal segment 344 of the second working catheter 304.

The catheter system 300 additionally includes a first locking mechanism 321 and a second locking mechanism 323 each which is schematically shown in FIG. 14. Each of the locking mechanisms 321, 323 is substantially identical to the locking mechanism 56 described hereinabove with regard to the catheter system 12. In particular, the first locking mechanism 321 operates to lock the first working catheter 303 in relation to the guide catheter 302 at any one of two positions, while the second locking mechanism 323 also operates to lock the second working catheter 304 in relation to the guide catheter 302 at any one of two positions. In particular, the first locking mechanism 321 may lock the first working catheter 303 relative to the guide catheter 302 in an operative position (see FIG. 14) or in a stowed position (see FIG. 15). Similarly, the second locking mechanism 323 may lock the second working catheter 304 relative to the guide catheter 302 in an operative position (see FIG. 14) or in a stowed position (see FIG. 15).

It should be noted that when the first working catheter 303 is locked in the operative position, (i) the first working catheter 303 extends through the first guide lumen 308 of the guide catheter 302 and out of the first distal guide orifice 314 of the guide catheter 302, and (ii) the distal orifice 336 is positioned outside of the guide catheter 302. On the other hand, when the first working catheter 303 is locked in the stowed position, (i) the first working catheter 303 extends into the first guide lumen 308 of the guide catheter 302, and (ii) the distal orifice 336 is positioned within the first guide lumen 308 of the guide catheter 302.

Similarly, when the second working catheter 304 is locked in the operative position, (i) the second working catheter 304 extends through the second guide lumen 310 of the guide catheter 302 and out of the second distal guide orifice 318 of the guide catheter 302, and (ii) the distal orifice 340 is positioned outside of the guide catheter 302. On the other hand, when the second working catheter 304 is locked in the stowed position, (i) the second working catheter 304 extends into the second guide lumen 310 of the guide catheter 302, and (ii) the distal orifice 340 is positioned within the second guide lumen 310 of the guide catheter 302.

The guide catheter 302 further includes a pair of distal blood flow valves 330 and a pair of proximal blood flow valves 332 positioned within the guide lumens 308, 310 as shown in FIGS. 14–15. The blood flow valves 330 and 332 are substantially identical to the blood flow valves 37 and 39 which were described hereinabove with regard to the catheter system 12.

A clamp 346 is positioned on the first working catheter 303, while another clamp 348 is positioned on the second working catheter 304. The clamps 346, 348 are substantially identical in construction and function to the clamps 62, 64 discussed hereinabove with regard to the catheter system 12.

The catheter system 300 is placed within the body 14 in substantially the same manner as was described hereinabove with respect to the placement of the catheter system 12 within the body 14 (i.e. by the tunneled catheter technique). While in the body 14, the locking mechanism 321 functions to lock the first working catheter 303 to the guide catheter 302 in either its stowed position (FIG. 15) or its operative position (FIG. 14). Similarly, while in the body 14, the locking mechanism 323 functions to lock the second working catheter 304 to the guide catheter 302 in either its stowed position (FIG. 15) or its operative position (FIG. 14).

It should be appreciated that FIG. 15 shows the first working catheter 303 locked to the guide catheter 302 in the stowed position. While the first working catheter 303 is locked in the stowed position in the patient's body 14 between dialysis sessions, the distal orifice 336 of the first working catheter 303 would be isolated from contact with the blood flow in the superior vena cava 32. FIG. 14 shows the first working catheter 303 locked to the guide catheter 302 in the operative position. While the first working catheter 303 is locked in the operative position in the patient's body 14 during performance of a dialysis procedure, the distal orifice 336 of the first working catheter 303 would be positioned within the blood flow in the superior vena cava 32.

Similarly, FIG. 15 shows the second working catheter 304 locked to the guide catheter 302 in the stowed position. While the second working catheter 304 is locked in the stowed position in the patient's body 14 between dialysis sessions, the distal orifice 340 of the second working catheter 304 would be isolated from contact with the blood flow in the superior vena cava 32. FIG. 14 shows the second working catheter 304 locked to the guide catheter 302 in the operative position. While the second working catheter 304 is locked in the operative position in the patient's body 14 during performance of a dialysis procedure, the distal orifice 340 of the second working catheter 304 would be positioned within the blood flow in the superior vena cava 32.

Also, please note that the working catheters 303, 304 of the catheter system 300 contact the blood located in the vascular system 24 for a substantially reduced amount of time in comparison to the amount of time a conventional dialysis catheter is being contacted by blood located in the vascular system. Accordingly, the physical structure of the working catheters 303, 304 of the catheter system 300 may be substantially the same or similar to the physical structure of a conventional short-term catheter for the same reasons hereinabove discussed in regard to the dialysis catheter 42 of the catheter system 12 in section 1(b) entitled "Performance of a Dialysis Session with the Catheter System 12".

Figure 16:
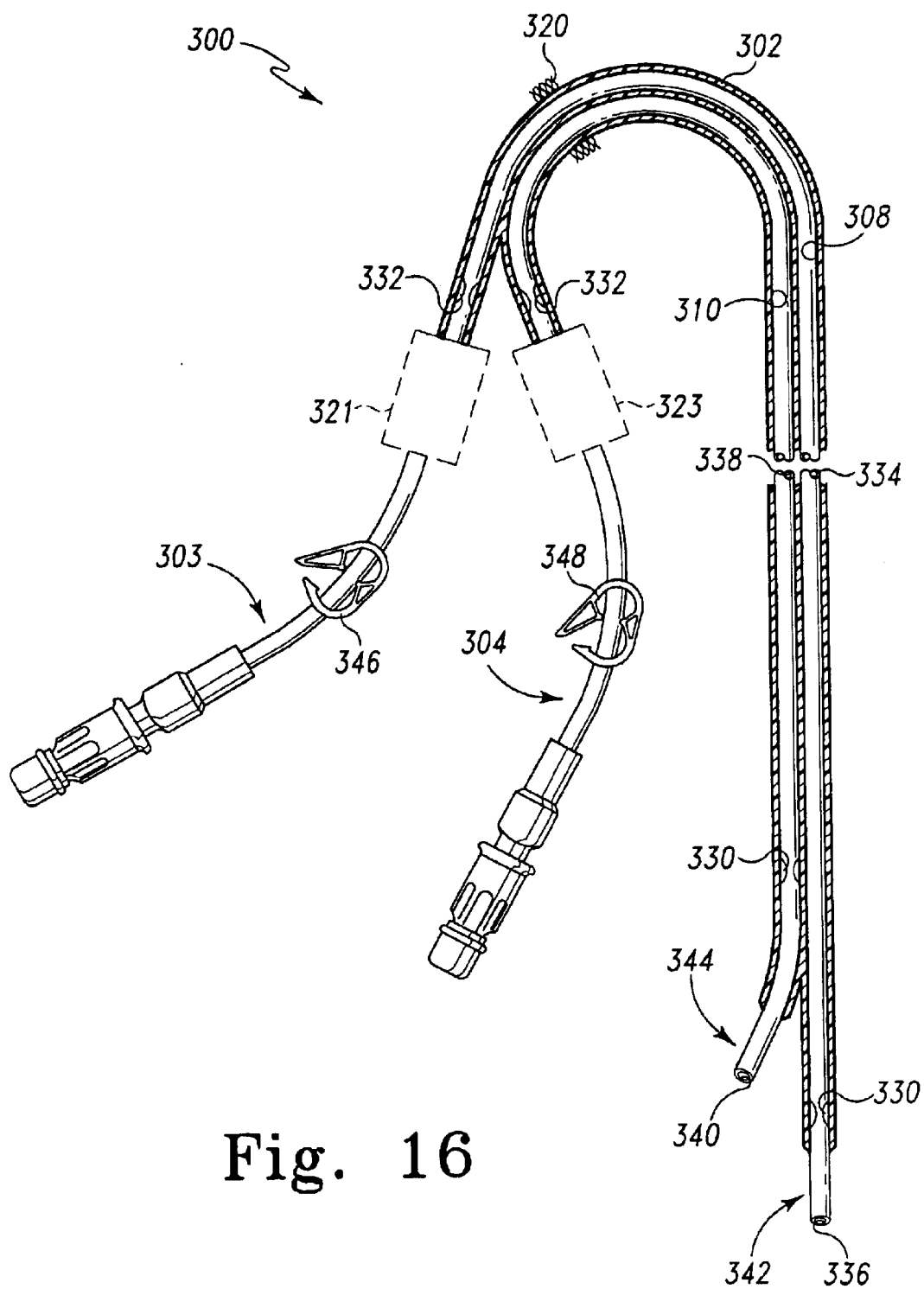
FIG. 16 is a view similar to FIG. 14, but showing another catheter system which incorporates the features of the present invention therein, with the working catheters shown positioned in the operative position.

The catheter system 300 is shown in FIGS. 14 and 15 as having the distal segment of the guide lumen 310 located adjacent to the guide lumen 308. In the embodiment shown in FIGS. 14 and 15, the guide catheter 302 can be said to possess a side-by-side configuration. An alternative to providing the guide catheter 302 with a side-by-side configuration is shown in FIG. 16. In particular, a distal portion of the guide lumens 308, 310 of the catheter system 300 may be alternatively configured so that the distal portion of the guide catheter 302 is arranged in a bifurcated configuration as shown in FIG. 16. In such a configuration, the distal portion of the guide lumen 310 is arranged so as to gradually extend away from the distal portion of the guide lumen 308 as shown in FIG. 16. In the embodiment shown in FIG. 16, the guide catheter 302 can be said to possess a "split-tip" configuration.

IV. Catheter System 400

FIGS. 17–18 show a catheter system 400 which also incorporates the features of the present invention therein. The catheter system 400 includes a guide catheter 402 and a single lumen working catheter 404. The guide catheter 402 has an active lumen 408 and a guide lumen 410 each which extends along the length of the guide catheter 402 as shown in FIG. 17. The guide lumen 410 defines a distal guide orifice 414. The working catheter 404 is positioned within the guide lumen 410 of the guide catheter 402.

The catheter system 400 is placed within the body 14 in substantially the same manner as was described hereinabove with respect to the placement of the catheter system 12 within the body 14 (i.e. by the tunneled catheter technique). Furthermore, the catheter system 400 is used to perform a dialysis procedure in substantially the same manner as was described hereinabove with respect to the performance of a dialysis procedure with the catheter system,12 (see e.g. Section 1 (b) entitled: "Performance of a Dialysis Session with the Catheter System 12").

The guide catheter 402 has a tissue ingrowth member 416 secured to an outer surface thereof. The tissue ingrowth member 416 is substantially identical to tissue ingrowth member 43 described hereinabove with regard to the catheter system 12.

The working catheter 404 defines a lumen 405 through which fluid, such as blood, may be advanced. The lumen 405 defines a distal orifice 426. The distal orifice 426 is defined in a distal segment 428 of the working catheter 404.

The catheter system 400 additionally includes a locking mechanism 421 which is schematically shown in FIG. 17. The locking mechanism 421 is substantially identical to the locking mechanism 56 described hereinabove with regard to the catheter system 12. In particular, the locking mechanism 421 operates to lock the working catheter 404 in relation to the guide catheter 402 at any one of two positions. In particular, the locking mechanism 421 may lock the working catheter 404 relative to the guide catheter 402 in an operative position (see FIG. 17) or in a stowed position (see FIG. 18).

It should be noted that when the working catheter 404 is locked in the operative position, (i) the working catheter 404 extends through the guide lumen 410 of the guide catheter 402 and out of the distal guide orifice 414 of the guide catheter 402, and (ii) the distal orifice 426 of the working catheter 404 is positioned outside of the guide catheter 402. On the other hand, when the working catheter 404 is locked in the stowed position, (i) the working catheter 404 extends into the guide lumen 410 of the guide catheter 402, and (ii) the distal orifice 426 is positioned within the guide lumen 410 of the guide catheter 402.

The guide catheter 402 further includes a distal blood flow valve 422 and a proximal blood flow valve 424 positioned within the guide lumen 410 as shown in FIGS. 17 and 18. The blood flow valves 422 and 424 are substantially identical to the blood flow valves 37 and 39 which were described hereinabove with regard to the catheter system 12. The guide catheter 402 may further include an additional distal blood flow valve (not shown) located in the distal portion of the active lumen 408 and an additional proximal blood flow valve (not shown) located in the proximal portion of the active lumen 408. These additional blood flow valves would also be substantially identical to the blood flow valves 37 and 39 which were described hereinabove with regard to the catheter system 12.

A clamp 430 is positioned on the working catheter 404. Another clamp 431 is positioned on the guide catheter 402 as shown in FIG. 17. The clamps 430, 431 are substantially identical in construction and function to the clamps 62, 64 discussed hereinabove with regard to the catheter system 12.

The catheter system 400 is placed within the body 14 in substantially the same manner as was described hereinabove with respect to the placement of the catheter system 12 within the body 14 (i.e. by the tunneled catheter technique). While in the body 14, the locking mechanism 421 functions to lock the working catheter 404 to the guide catheter 402 in either its stowed position (FIG. 18) or its operative position (FIG. 17).

It should be appreciated that FIG. 18 shows the working catheter 404 locked to the guide catheter 402 in the stowed position. While the working catheter 404 is locked in the stowed position in the patient's body 14 between dialysis sessions, the distal orifice 426 of the working catheter 404 would be isolated from contact with the blood flow in the superior vena cava 32. FIG. 17 shows the working catheter 404 locked to the guide catheter 402 in the operative position. While the working catheter 404 is locked in the operative position during performance of a dialysis procedure, the distal orifice 426 of the working catheter 404 would be positioned within the blood flow in the superior vena cava 32.

Also, please note that the working catheter 404 of the catheter system 400 contacts the blood located in the vascular system 24 for a substantially reduced amount of time in comparison to the amount of time a conventional dialysis catheter is being contacted by blood located in the vascular system. Accordingly, the physical structure of the working catheter 404 of the catheter system 400 may be substantially the same or similar to the physical structure of a conventional short-term catheter for the same reasons hereinabove discussed in regard to the dialysis catheter 42 of the catheter system 12 in section 1 (b) entitled "Performance of a Dialysis Session with the Catheter System 12".

Figure 19:
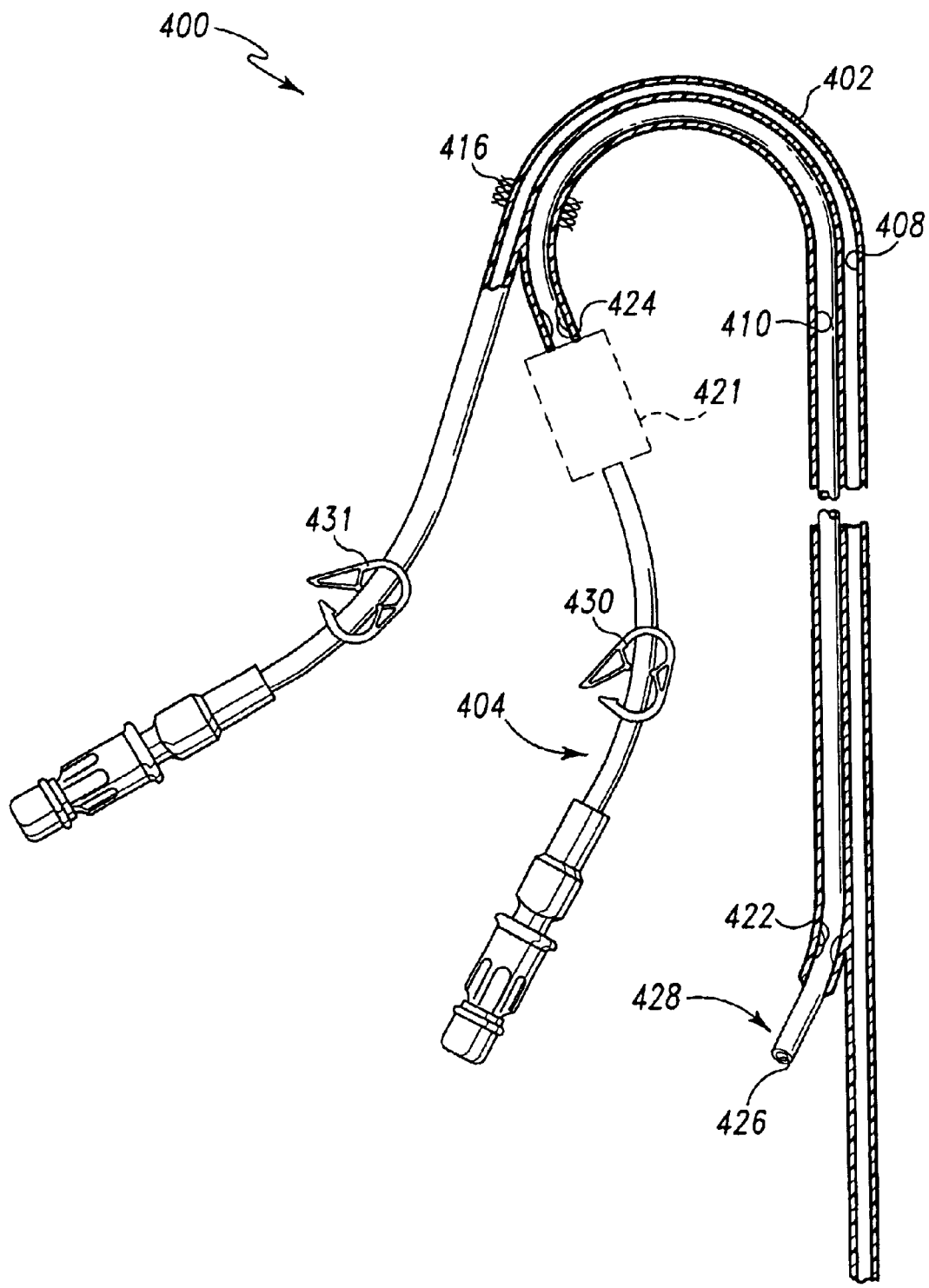
FIG. 19 is a view similar to FIG. 17, but showing another catheter system which incorporates the features of the present invention therein, with the working catheter shown positioned in the operative position.

The catheter system 400 is shown in FIGS. 17 and 18 as having the distal segment of the guide lumen 410 located adjacent to the active lumen 408. In the embodiment shown in FIGS. 17 and 18, the guide catheter 402 can be said to possess a side-by-side configuration. An alternative to providing the guide catheter 402 with a side-by-side configuration is shown in FIGS. 19. In particular, a distal portion of both the guide lumen 410 and the active lumen 408 of the catheter system 400 may be alternatively configured so that the distal portion of the guide catheter 402 is arranged in a bifurcated configuration as shown in FIG. 19. In such a configuration, the distal portion of the guide lumen 410 is arranged so as to gradually extend away from the distal portion of the active lumen 408 as shown in FIG. 19. In the embodiment shown in FIG. 19, the guide catheter 402 can be said to possess a "split-tip" configuration.

Figure 20:
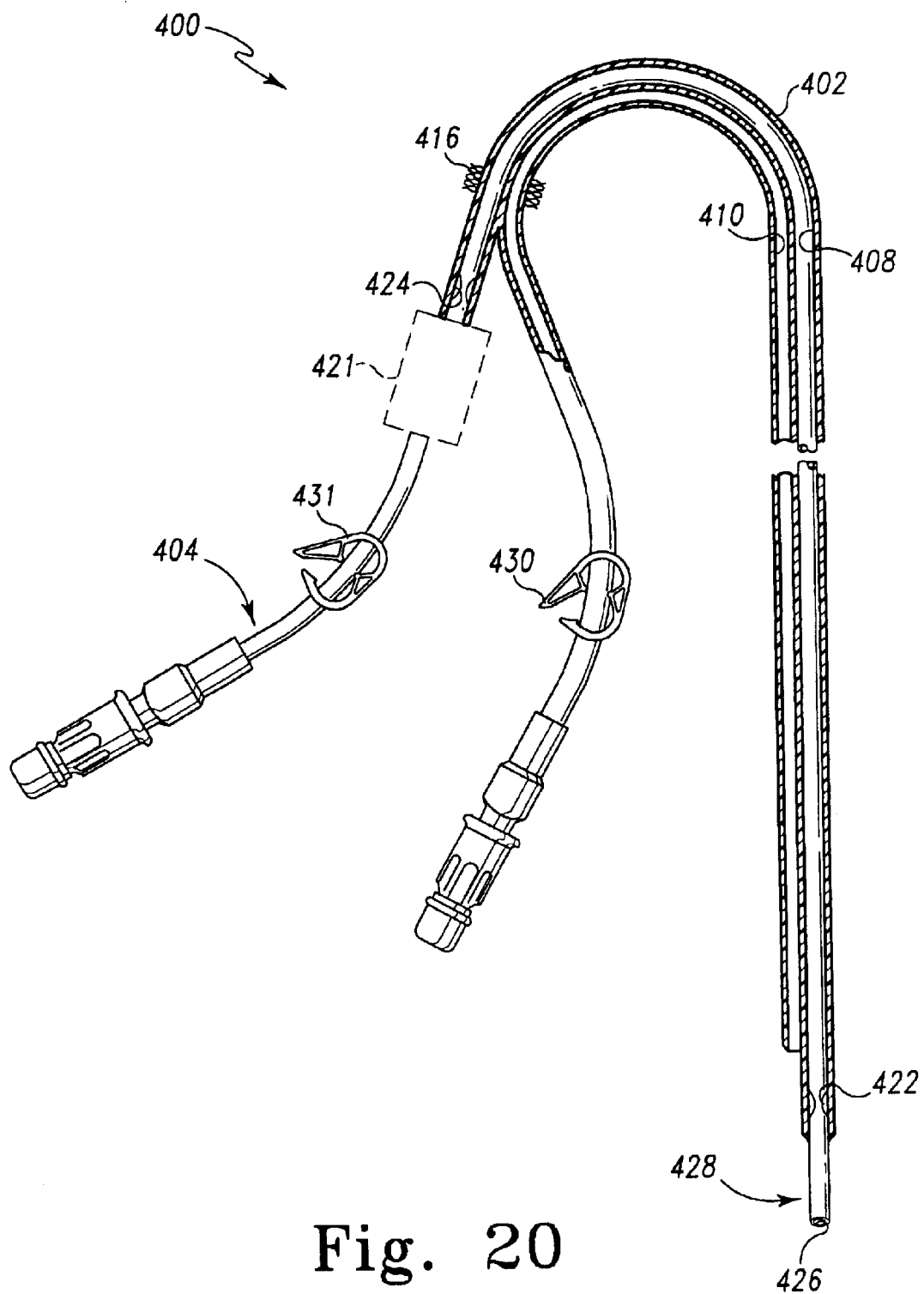
FIG. 20 is a view similar to FIG. 17, but showing still another catheter system which incorporates the features of the present invention therein.

In addition, the catheter system 400 is shown in FIGS. 17 and 18 as having the working catheter 404 positioned within the guide lumen 410 of the guide catheter 402 while the active lumen 408 does not receive any such catheter therein. In an alternative embodiment of the present invention which is shown in FIG. 20, the catheter system 400 may be modified such that the working catheter 404 would be positioned within the lumen 408 of the guide catheter 402, while the lumen 410 would not receive any such catheter therein. In such an embodiment, the lumen 410 would function as an active lumen through which a fluid, such as blood, may be advanced therethrough. Further, in such an embodiment, the lumen 408 would function as a guide lumen.

V. Catheter System 500

Figures 21, 22:
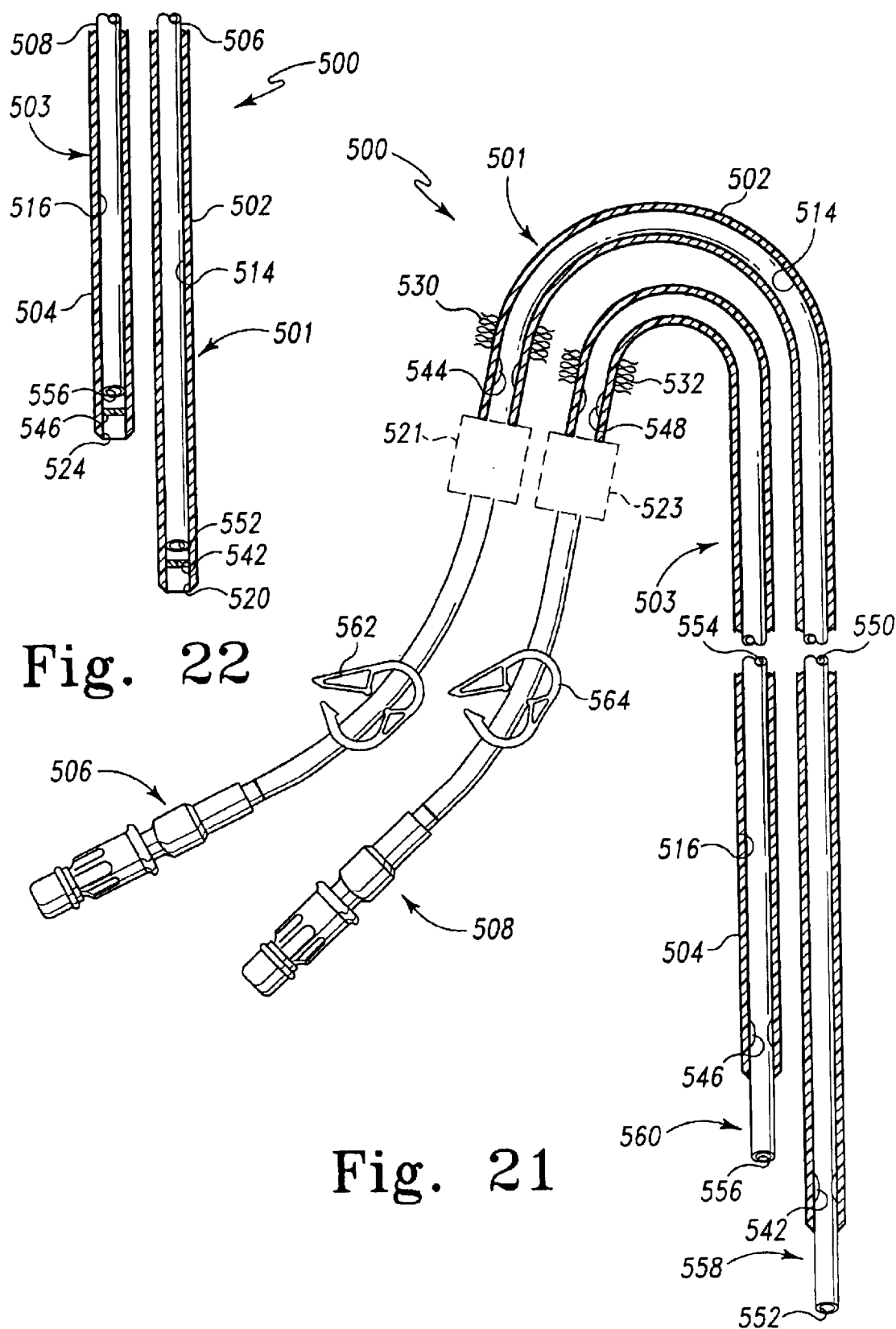
FIG. 21 is a view similar to FIG. 3, but showing yet another catheter system which incorporates the features of the present invention therein, with the working catheters shown positioned in the operative position.
FIG. 22 is a fragmentary cross sectional view of a distal portion of the catheter system of FIG. 21, but showing the working catheters positioned in the stowed position.
Figure 23:
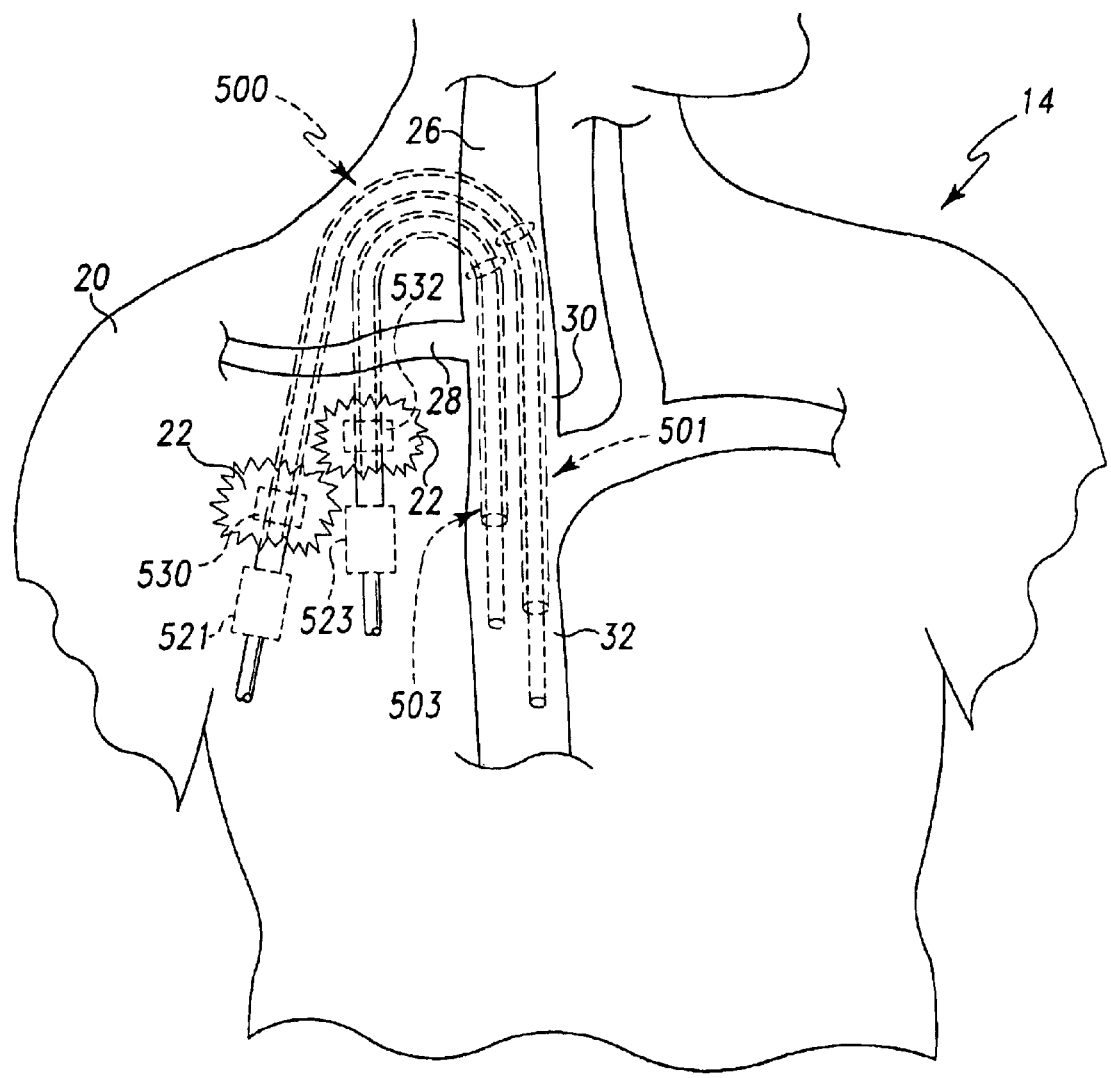
FIG. 23 is an enlarged view which is similar to FIG. 2, but showing the catheter system of FIG. 21 (i) extending from the right upper chest, (ii) tunneled under the skin within the subcutaneous tissue of the patient for a distance, (iii) entering a pair of venotomies in the right internal jugular vein, and (iv) passing caudally in the right internal jugular vein, the right innominate vein and the superior vena cava.

FIGS. 21–23 show a catheter system 500 which further incorporates the features of the present invention therein. The catheter system 500 includes a first catheter apparatus 501 and a second catheter apparatus 503. The first catheter apparatus 501 includes a first guide catheter 502 and a first single lumen working catheter 506, while the second catheter apparatus 503 includes a second guide catheter 504 and a second single lumen working catheter 508.

The catheter system 500 is placed within the body 14 in substantially the same manner as was described hereinabove with respect to the placement of the catheter system 12 within the body 14 (i.e. each catheter apparatus 501, 503 is placed within the body by the tunneled catheter technique). Furthermore, the catheter system 500 is used to perform a dialysis procedure in substantially the same manner as was described hereinabove with respect to the performance of a dialysis procedure with the catheter system 12 (see e.g. Section 1(b) entitled: "Performance of a Dialysis Session with the Catheter System 12").

The first guide catheter 502 has a first guide lumen 514 defined therein which extends along the length of the guide catheter 502 as shown in FIG. 21. The second guide catheter 504 has a second guide lumen 516 defined therein which extends along the length of the guide catheter 504 as also shown in FIG. 21. The first guide lumen 514 defines a first distal guide orifice 520, while the second guide lumen 516 defines a second distal guide orifice 524.

The first working catheter 506 is positioned within the guide lumen 514 of the guide catheter 502, while the second working catheter 508 is positioned within the guide lumen 516 of the guide catheter 504 as shown in FIGS. 21–22.

Referring to FIGS. 21 and 23, the first guide catheter 502 has a tissue ingrowth member 530 secured to an outer surface thereof, while the second guide catheter 504 has a tissue ingrowth member 532 secured to an outer surface thereof. The tissue ingrowth members 530, 532 are substantially identical to tissue ingrowth member 43 described hereinabove with regard to the catheter system 12.

The first working catheter 506 includes a lumen 550. The lumen 550 defines a distal orifice 552. Similarly, the second working catheter 508 includes a lumen 554. The lumen 554 defines a distal orifice 556. The distal orifice 552 is defined in a distal segment 558 of the first working catheter 506. Similarly, the distal orifice 556 is defined in a distal segment 560 of the second working catheter 508.

The catheter system 500 additionally includes a first locking mechanism 521 and a second locking mechanism 523 each which is schematically shown in FIGS. 21 and 23. Each of the locking mechanisms 521, 523 is substantially identical to the locking mechanism 56 described hereinabove with regard to the catheter system 12. In particular, the first locking mechanism 521 operates to lock the first working catheter 506 in relation to the first guide catheter 502 at any one of two positions, while the second locking mechanism 523 also operates to lock the second working catheter 508 in relation to the second guide catheter 504 at any one of two positions. In particular, the first locking mechanism 521 may lock the first working catheter 506 relative to the first guide catheter 502 in an operative position (see FIG. 21) or in a stowed position (see FIG. 22). Similarly, the second locking mechanism 523 may lock the second working catheter 508 relative to the second guide catheter 504 in an operative position (see FIG. 21) or in a stowed position (see FIG. 22).

It should be noted that when the first working catheter 506 is locked in the operative position, (i) the first working catheter 506 extends through the first guide lumen 514 of the first guide catheter 502 and out of the first distal guide orifice 520 of the first guide catheter 502, and (ii) the distal orifice 552 of the first working catheter 506 is positioned outside of the first guide catheter 502. On the other hand, when the first working catheter 506 is locked in the stowed position, (i) the first working catheter 506 extends into the first guide lumen 514 of the first guide catheter 502, and (ii) the distal orifice 552 of the first working catheter 506 is positioned within the first guide lumen 514 of the first guide catheter 502.

Similarly, when the second working catheter 508 is locked in the operative position, (i) the second working catheter 508 extends through the second guide lumen 516 of the second guide catheter 504 and out of the second distal guide orifice 524 of the second guide catheter 504, and (ii) the distal orifice 556 of the second working catheter 508 is positioned outside of the second guide catheter 504. On the other hand, when the second working catheter 508 is locked in the stowed position, (i) the second working catheter 508 extends into the second guide lumen 516 of the second guide catheter 504, and (ii) the distal orifice 556 of the second working catheter 508 is positioned within the second guide lumen 516 of the second guide catheter 504.

The first guide catheter 502 further includes a distal blood flow valve 542 and a proximal blood flow valve 544 positioned within the first guide lumen 514 as shown in FIGS. 21 and 22. The second guide catheter 504 further includes a distal blood flow valve 546 and a proximal blood flow valve 548 positioned within the second guide lumen 516 as also shown in FIGS. 21 and 22. The blood flow valves 542, 544, 546, and 548 are substantially identical to the blood flow valves 37 and 39 which were described hereinabove with regard to the catheter system 12.

A clamp 562 is positioned on the first working catheter 506, while another clamp 564 is positioned on the second working catheter 508. The clamps 562, 564 are substantially identical in construction and function to the clamps 62, 64 discussed hereinabove with regard to the catheter system 12.

The catheter system 500 is placed within the body 14 in substantially the same manner as was described hereinabove with respect to the placement of the catheter system 12 within the body 14 (i.e. both catheter apparatus 501 and 503 are placed in the body 14 using the tunneled catheter technique). While in the body 14, the locking mechanism 521 functions to lock the first working catheter 506 to the first guide catheter 502 in either its stowed position (FIG. 22) or its operative position (FIG. 21). Similarly, while in the body 14, the locking mechanism 523 functions to lock the second working catheter 508 to the second guide catheter 504 in either its stowed position (FIG. 22) or its operative position (FIG. 21).

It should be appreciated that FIG. 22 shows the first working catheter 506 locked to the first guide catheter 502 in the stowed position. While the first working catheter 506 is locked in the stowed position in the patient's body 14 between dialysis sessions, the distal orifice 552 of the first working catheter 506 would be isolated from contact with the blood flow in the superior vena cava 32. FIG. 21 shows the first working catheter 506 locked to the first guide catheter 502 in the operative position. While the first working catheter 506 is locked in the operative position during performance of a dialysis procedure, the distal orifice 552 of the first working catheter 506 would be positioned within the blood flow in the superior vena cava 32.

Also, please note that the working catheters 506, 508 of the catheter system 500 contact the blood located in the vascular system 24 for a substantially reduced amount of time in comparison to the amount of time a conventional dialysis catheter is being contacted by blood located in the vascular system. Accordingly, the physical structure of the working catheters 506, 508 of the catheter system 500 may be substantially the same or similar to the physical structure of a conventional short-term catheter for the same reasons hereinabove discussed in regard to the dialysis catheter 42 of the catheter system 12 in section 1(b) entitled "Performance of a Dialysis Session with the Catheter System 12".

Similarly, FIG. 22 shows the second working catheter 508 locked to the second guide catheter 504 in the stowed position. While the second working catheter 508 is locked in the stowed position in the patient's body 14 between dialysis sessions, the distal orifice 556 of the second working catheter 508 would be isolated from contact with the blood flow in the superior vena cava 32. FIG. 21 shows the second working catheter 508 locked to the second guide catheter 504 in the operative position. While the second working catheter 508 is locked in the operative position during performance of a dialysis procedure, the distal orifice 556 of the second working catheter 508 would be positioned within the blood flow in the superior vena cava 32.

The catheter system 500 is shown in FIGS. 21–23 as having the ability to retract and lock (i) the first working catheter 506 of the first catheter apparatus 501 in relation to the first guide catheter 502, as well as (ii) the second working catheter 508 of the second catheter apparatus 503 in relation to the second guide catheter 504. However, it should be appreciated that a first alternative arrangement (not shown) to the arrangement described in FIGS. 21–23 is to configure the second catheter apparatus 503 to be exactly the same as shown in FIGS. 21–23, but to configure the first catheter apparatus 501 to be similar to a conventional single lumen catheter (i.e. a catheter apparatus which does not possess a retractable inner working catheter). It should be further appreciated that a second alternative arrangement (not shown) to the arrangement described in FIGS. 21–23 is to configure the first catheter apparatus 501 to be exactly the same as shown in FIGS. 21–23, but to configure the second catheter apparatus 503 to be similar to a conventional single lumen catheter (i.e. a catheter apparatus which does not possess a retractable inner working catheter).

VI. Catheter System 600

Figure 26:
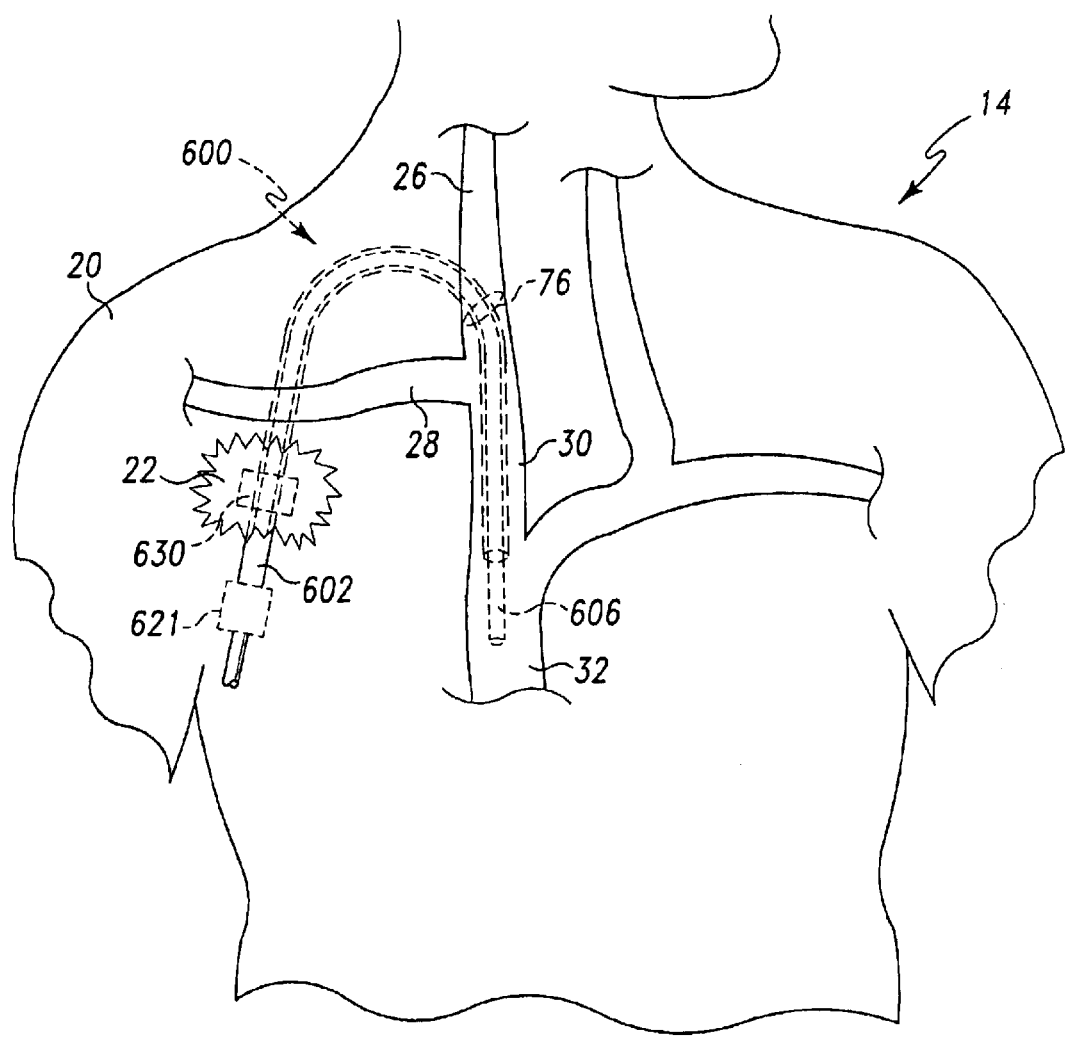
FIG. 26 is an enlarged view which is similar to FIG. 2, but showing the catheter system of FIG. 24 (i) extending from the right upper chest, (ii) tunneled under the skin within the subcutaneous tissue of the patient for a distance, (iii) entering a venotomy in the right internal jugular vein, and (iv) passing caudally in the right internal jugular vein, the right innominate vein and the superior vena cava.

FIGS. 24–26 show a catheter system 600 which additionally incorporates the features of the present invention therein. The catheter system 600 may be used for the administration of total parenteral nutrition (hereinafter referred to as "TPN") to a patient. TPN generally refers to intravenous feeding via an indwelling central venous catheter of nutritive material in conditions where patients cannot eat by mouth or receive nutrition enterally (e.g. by gastric tube or small bowel tube). Some examples where prolonged administration of TPN to a patient are indicated include instances where a patient suffers from an insufficient small bowel absorptive area such as short gut syndrome or an instance where a patient suffers from prolonged intestinal ileus which may have resulted due to a severe burn injury or an abdominal surgery. Other examples where prolonged administration of TPN to a patient are indicated include instances where a patient has a condition requiring prolonged bowel rest such as where the patient suffers from pancreatitis or inflammatory bowel disease. Yet another example where prolonged administration of TPN to a patient is indicated is the situation where a patient refuses to eat such as would occur in the case of severe anorexia nervosa.

Referring now in detail to FIGS. 24–26, the catheter system 600 includes a guide catheter 602 and a single lumen working catheter 606. The guide catheter 602 has a guide lumen 614 which extends along the length of the guide catheter 602 as shown in FIG. 24. The guide lumen 614 defines a distal guide orifice 620. The working catheter 606 is positioned within the guide lumen 614 of the guide catheter 602 as shown in FIGS. 24–26.

The catheter system 600 is placed within the body 14 in substantially the same manner as was described hereinabove with respect to the placement of the catheter system 12 within the body 14 (i.e. by the tunneled catheter technique). Furthermore, the catheter system 600 is used to perform a TPN administration procedure in substantially the same manner as was described hereinabove with respect to the performance of a dialysis procedure with the catheter system 12 (see e.g. Section 1(b) entitled: "Performance of a Dialysis Session with the Catheter System 12"). In particular, when a patient desires to engage in a TPN administration session, the working catheter 606 is connected to a source of TPN. Thereafter, the working catheter 606 is unlocked from the guide catheter 602. Then, the working catheter 606 is advanced to its operative position. Once in its operative position, the working catheter 606 is locked to the guide catheter 602 so that a distal segment 658 of the working catheter 606 extends out of the distal guide orifice 620 as shown in FIG. 24. Thereafter, the TPN administration session is performed in a conventional manner as is well known in the art. Once the TPN administration session is completed, the working catheter 606 is unlocked from the guide catheter 602 and retracted to its stowed position. Once in its stowed position, the working catheter 606 is locked to the guide catheter 602. Then, the working catheter 606 is disconnected from the source of TPN. Thereafter, the patient is able to carry on about his/her business.

The working catheter 606 includes a lumen 650. The lumen 650 defines a distal orifice 652. The distal orifice 652 is defined in the distal segment 658 of the working catheter 606.

Referring to FIGS. 24 and 26, the guide catheter 602 has a tissue ingrowth member 630 secured to an outer surface thereof. The tissue ingrowth member 630 is substantially identical to tissue ingrowth member 43 described hereinabove with regard to the catheter system 12.

The catheter system 600 additionally includes a locking mechanism 621 which is schematically shown in FIGS. 24 and 26. The locking mechanism 621 is substantially identical to the locking mechanism 56 described hereinabove with regard to the catheter system 12. In particular, the locking mechanism 621 operates to lock the working catheter 606 in relation to the guide catheter 602 at any one of two positions. In particular, the locking mechanism 621 may lock the working catheter 606 relative to the guide catheter 602 in an operative position (see FIG. 24) or in a stowed position (see FIG. 25).

It should be noted that when the working catheter 606 is locked in the operative position, (i) the working catheter 606 extends through the guide lumen 614 of the guide catheter 602 and out of the distal guide orifice 620 of the guide catheter 602, and (ii) the distal orifice 652 of the working catheter 606 is positioned outside of the guide catheter 602. On the other hand, when the working catheter 606 is locked in the stowed position, (i) the working catheter 606 extends into the guide lumen 614 of the guide catheter 602, and (ii) the distal orifice 652 of the working catheter 606 is positioned within the guide lumen 614 of the guide catheter 602.

The guide catheter 602 further includes a distal blood flow valve 642 and a proximal blood flow valve 644 positioned within the guide lumen 614 as shown in FIGS. 24 and 25. The blood flow valves 642, 644 are substantially identical to the blood flow valves 37 and 39 which were described hereinabove with regard to the catheter system 12.

A clamp 662 is positioned on the working catheter 606. The clamp 662 is substantially identical in construction and function to the clamps 62, 64 discussed hereinabove with regard to the catheter system 12.

The catheter system 600 is placed within the body 14 in substantially the same manner as was described hereinabove with respect to the placement of the catheter system 12 within the body 14 (i.e. by the tunneled catheter technique). While in the body 14, the locking mechanism 621 functions to lock the working catheter 606 to the guide catheter 602 in either its stowed position (FIG. 25) or its operative position (FIG. 24).

It should be appreciated that FIG. 25 shows the working catheter 606 locked to the guide catheter 602 in the stowed position. While the working catheter 606 is locked in the stowed position in the patient's body 14 between TPN administration sessions, the distal orifice 652 of the working catheter 606 would be isolated from contact with the blood flow in the superior vena cava 32. FIG. 24 shows the working catheter 606 locked to the guide catheter 602 in the operative position. While the working catheter 606 is locked in the operative position during performance of a TPN administration procedure, the distal orifice 652 of the catheter 600 would be positioned within the blood flow in the superior vena cava 32.

Also, please note that the working catheter 606 of the catheter system 600 contacts the blood located in the vascular system 24 for a substantially reduced amount of time in comparison to the amount of time a conventional dialysis catheter is being contacted by blood located in the vascular system. Accordingly, the physical structure of the working catheter 606 of the catheter system 600 may be substantially the same or similar to the physical structure of a conventional short-term catheter for the same reasons hereinabove discussed in regard to the dialysis catheter 42 of the catheter system 12 in section 1(b) entitled "Performance of a Dialysis Session with the Catheter System 12".

Figures 27, 28, 29:
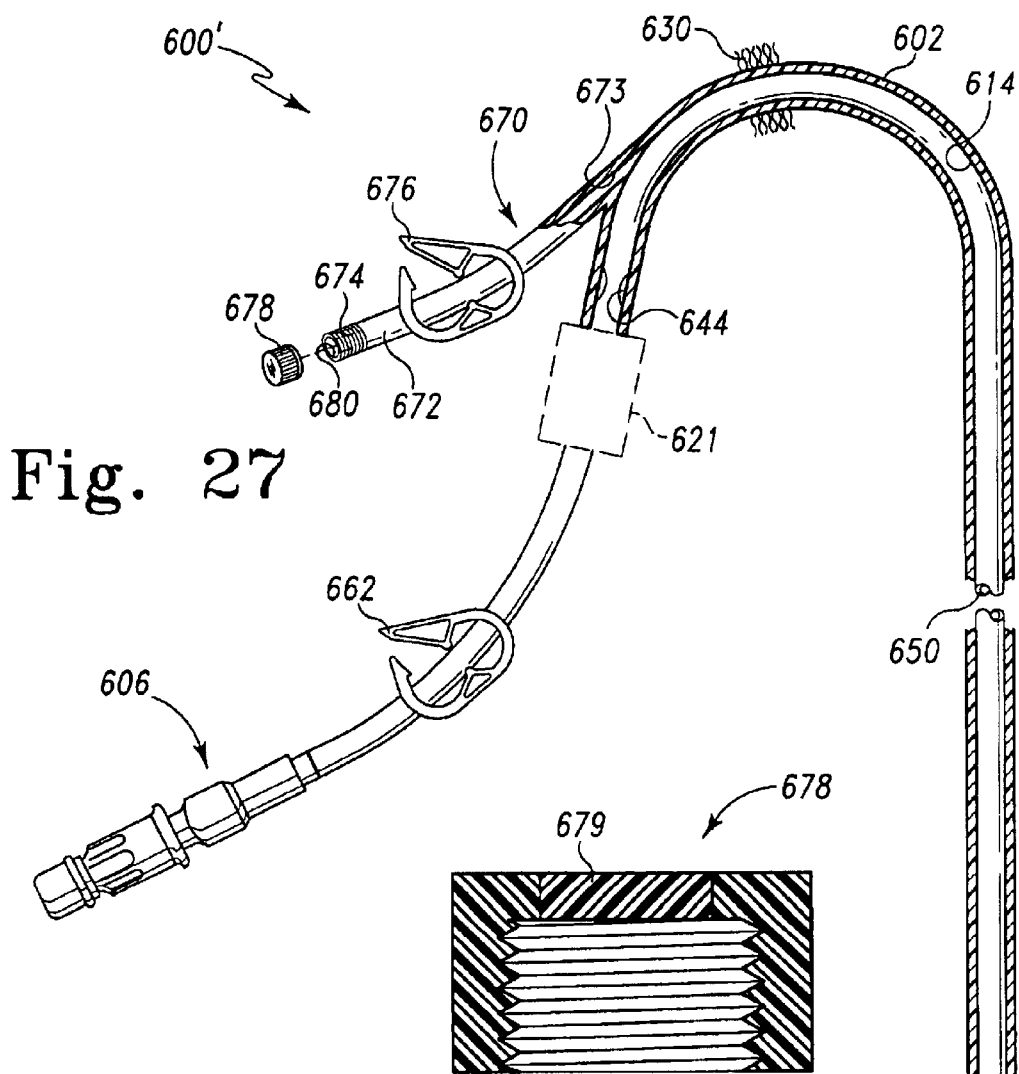
FIG. 27 is a view similar to FIG. 24, but showing another catheter system which incorporates the features of the present invention therein, with the working catheter shown positioned in the operative position.
FIG. 28 is an enlarged perspective view of the closure member of FIG. 27.
FIG. 29 is an enlarged cross sectional view of the closure member of FIG. 28 taken along the line 29—29 of FIG. 28 as viewed in the direction of the arrows.

An alternative configuration for the catheter system 600 is shown in FIG. 27. In particular, this alternative embodiment of the present invention shows a catheter system 600'. The catheter system 600' is placed within the body 14 in substantially the same manner as was described hereinabove with respect to the placement of the catheter system 12 within the body 14 (i.e. by the tunneled catheter technique). Further, the catheter system 600' is used in substantially the same manner as herein described with respect to the catheter system 600. Moreover, the catheter system 600' is exactly the same in construction and configuration as the catheter system 600 shown in FIGS. 24–26, with the exception that the catheter system 600' includes a sideport 670 through which fluid may be withdrawn or otherwise advanced. In particular, the sideport 670 includes a conduit 672 having a set of external threads 674 defined on a proximal end thereof. A clamp 676 is positioned on the conduit 672. The clamp 662 is substantially identical in construction and function to the clamps 62, 64 discussed hereinabove with regard to the catheter system 12. The conduit 672 defines a sideport lumen 673 which is in fluid communication with the guide lumen 614. Accordingly, air can be aspirated out of the guide lumen 614 through the sideport 670 via the conduit 672. Alternatively, the guide lumen 614 may be flushed with a fluid such as a saline, heparin, or urokinase solution between uses of the catheter system 600'(e.g. administration of TPN to a patient) while the working catheter 606 is locked in its stowed position (see e.g. FIG. 25). The guide lumen 614 may also be flushed with a saline, heparin, or urokinase solution while the working catheter 606 is locked in its operative position (see e.g. FIG. 27).

When not in use, the sideport 670 may be clamped shut with the clamp 676. Moreover, when not in use, a closure member or cap 678 may be secured to the conduit 672 to cover a proximal sideport orifice 680 which is defined by the conduit 672. The cap 678 is provided with a set of internal threads which cooperate with the set of external threads 674 so as to lock the cap 678 to the guide catheter 602. Optionally, the cap 678 may be provided with a silicone membrane 679, as shown in FIGS. 28–29, which may be traversed with a needle whereby a saline, heparin, or urokinase solution may be advanced into the conduit 672 in order to flush the guide catheter 602.

Additionally, while the closure member 678 is disclosed as being locked to the sideport 670 by an arrangement which includes cooperating internal and external threads and has advantages thereby, such closure member 678 may be locked to the sideport 670 by other locking arrangements such as a conventional tamper-proof (or child-proof) arrangement typically used on pill containers that contain prescription medication which is dispensed by a pharmacy.

It should be noted that any of the other embodiments of the present invention set forth herein (e.g. catheter systems 12, 200, 300, 400, and 500) may be modified to incorporate a sideport which is similar to sideport 670. In particular, any of the guide catheters of the catheter systems 12, 200, 300, 400, and 500 may be modified to include a sideport which is similar in construction, configuration, and use to the construction, configuration and use of the sideport 670 described herein.

VII. Conclusion

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

For instance, while the above-described dual-lumen catheter systems (e.g. catheter system 12, 200, 300, 400, and 500) were discussed as being effective to perform hemodialysis, such catheter systems can also be utilized to perform other medical procedures in which dual-lumen catheter access to the vascular system (e.g. the central venous system) is required. One example of such a medical procedure is plasmapheresis in which blood is withdrawn from the vascular system, components of the blood are separated outside of the body, and a portion of the blood components are then returned to the vascular system.

In addition, another medical procedure which may be performed using the above-described dual-lumen catheter systems is peritoneal dialysis. In particular, catheter system occlusion may be prevented during a peritoneal dialysis procedure in a manner similar to that described above with respect to the catheter systems 12, 200, 300, 400, and 500.

Moreover, while the above-described single-lumen catheter systems (e.g. catheter system 600, 600') were discussed as being effective to perform administration of total parenteral nutrition, such catheter systems can be utilized to perform other medical procedures in which single-lumen catheter access to the vascular system is required. Examples of other medical procedures in which single-lumen catheter access to the vascular system is required includes (i) chemotherapy or other long-term medicinal infusions, (ii) repetitive blood transfusions, and (iii) repetitive blood samplings.

Furthermore, each of the above-described catheter systems (e.g. catheter systems 12, 200, 300, 400, 500, 600, 600') were described as having a tissue ingrowth member (e.g. tissue ingrowth members 43, 320, 416, 530, 630) which is configured to facilitate attachment of such catheter system to the subcutaneous tissue 22 of the body. While the provision of such a tissue ingrowth member to effect attachment of such catheter system to the body of a patient has many advantages, the present invention may utilize other mechanisms which can function to attach such catheter system to the body on a long-term or even a short-term basis and still benefit from various advantages of the other features of the present invention. An example of such an attachment mechanism is a plastic member having a hole or recess for receiving a catheter therein and further having one or more wing-like or flap-like extensions which may be sutured or taped to the skin of the patient 14. Additionally, it is possible that the above-described catheters systems of the present invention (e.g. catheter systems 12, 200, 300, 400, 500, 600, 600') may not include any mechanism which specifically functions to attach the catheter systems to the body yet still benefit from some of the advantages of the other features of the present invention.

While the above-described catheter systems 12, 200, 300, 400, 500, 600, and 600' were described as being placed in the body 14 utilizing the permanent catheterization technique and has many advantages thereby, such catheter systems 12, 200, 300, 400, 500, 600, and 600' could be placed in the body 14 utilizing other techniques (e.g. the temporary catheterization technique) and still achieve some of the advantages of the present invention.

While the separating diaphragm 39A is described as being substituted for the proximal valve 39 of the catheter system 12 (see FIG. 8A), another separating diaphragm, similar to the separating diaphragm 39A, may also be substituted for the distal valve 37 of the catheter system 12. Alternatively, the separating diaphragm 39A may be used in addition to the proximal valve 39 and the distal valve 37 to further prevent blood flow (or air flow) leakage between the guide catheter 34 and the working catheter 42. Moreover, while the separating diaphragm 39A is described as alternatively being incorporated into the catheter system 12, the separating diaphragm 39A may alternatively be incorporated into any of the following catheter systems described herein: catheter systems 200, 300, 400, 500, 600, 600'.

Also, while the above described working catheters 42, 303, 304, 404, 506, 508, 606 were shown as only having a single hole or orifice defined in its distal segment through which fluid may be advanced, it should be appreciated that the distal segment of any of such working catheters may have two or more holes defined in its distal segment each through which fluid may be advanced. For example, the distal segment of any one of such working catheters may have a single distal end hole (such as the distal orifice 336 of FIG. 14) and four additional holes defined in the sidewall of the distal segment, wherein each of the four additional holes is spaced apart from the distal end hole in the proximal direction by a distance.

Figure 30:
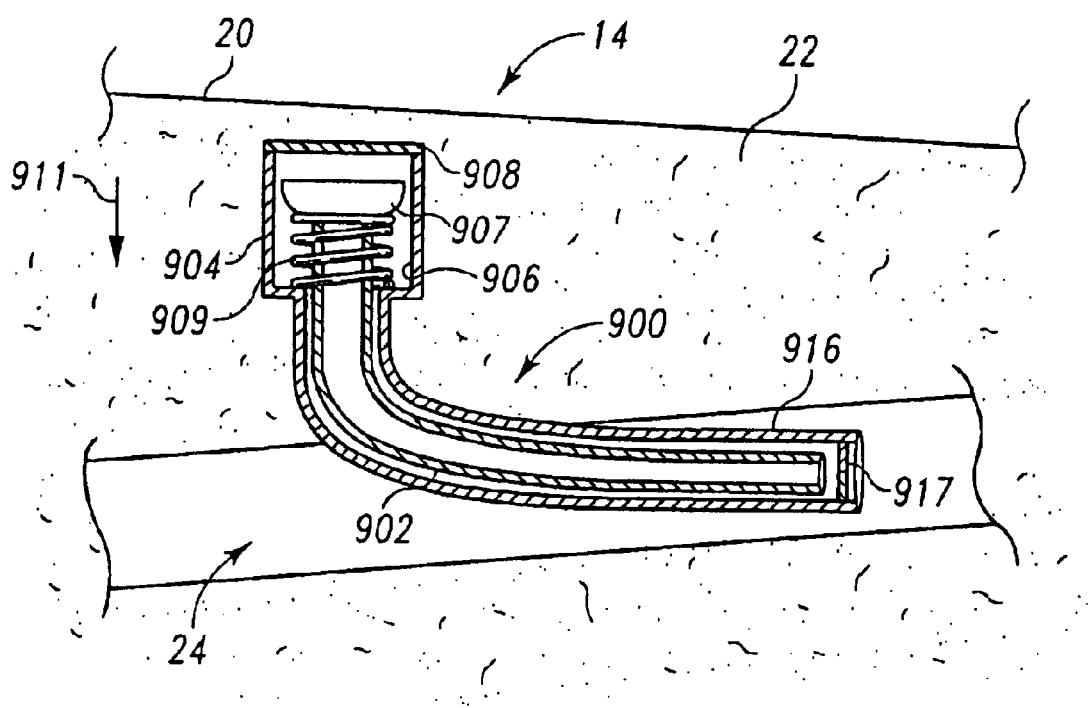
FIG. 30 is a side elevational view showing another catheter system which incorporates the features of the present invention therein, with the catheter system shown in the retracted or stowed position.
Figure 31:
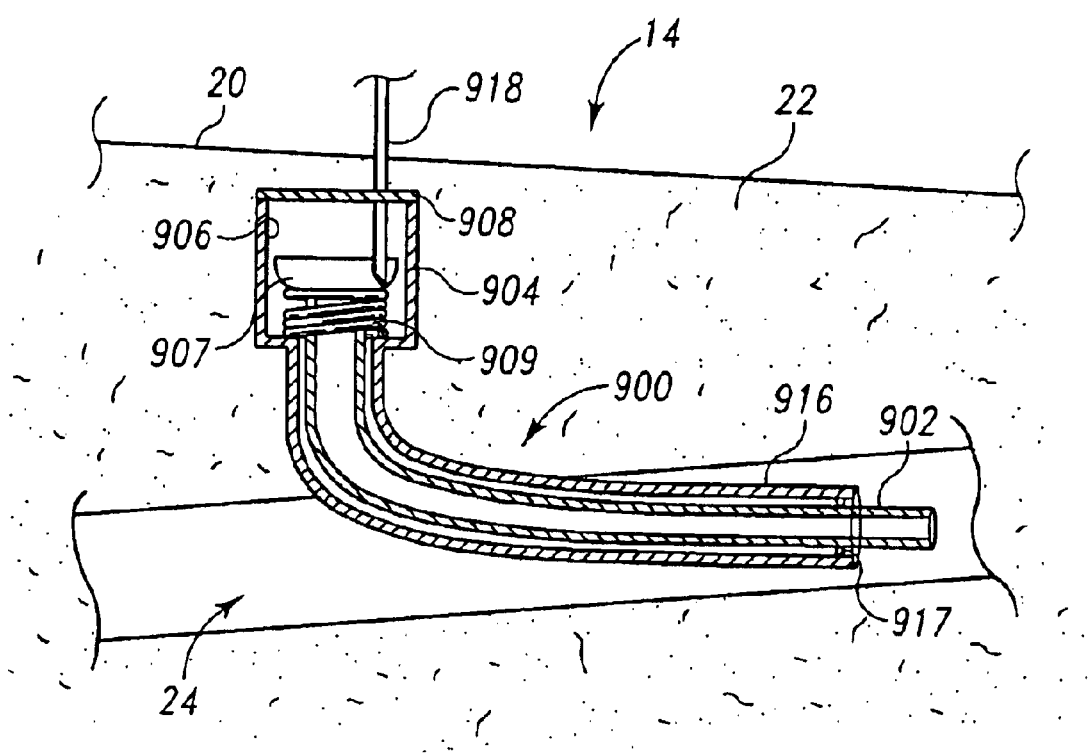
FIG. 31 is a view similar to FIG. 51, but showing the catheter system of FIG. 30 being positioned in the extended or operative position.

Additionally, while the above-described catheter system 600 was described as being implanted in the body 14 so that a proximal portion of such respective catheter system is located external to the body 14 and the remainder of such respective catheter system is located within the body 14 (as shown in FIG. 26), such catheter system 600 could be implanted entirely within the body and still achieve some of the advantages of the present invention. More particularly, such respective catheter system 600 could be configured as a subcutaneous port catheter system 900 having a retractable inner catheter 902 as shown in FIGS. 30–31. The subcutaneous port catheter system 900 would be implanted entirely beneath the skin 20 of the body 14 within the subcutaneous tissue 22 (see FIGS. 30–31). The subcutaneous port catheter system 900 further includes a reservoir 904 defining a chamber 906, and a septum 908 positioned over the chamber 906. A funnel 907 is attached to the proximal end of the retractable inner catheter 902. The funnel 907 is located within the reservoir 904 and further is in fluid communication with the retractable inner catheter 902 so that fluid advanced within the funnel 907 subsequently advances into the retractable inner catheter 902. A spring 909 is positioned around the proximal end portion of the retractable inner catheter 902. Movement of the funnel 907 in the direction of arrow 911 causes to the spring 909 to compress. The subcutaneous port catheter system 900 also includes a guide catheter 916 which is attached to the reservoir 904. The guide catheter 916 may include a distal valve 917. During use, the subcutaneous port catheter system 900 would be implanted in the body 14 so that a distal portion of each of the retractable inner catheter 902 and the guide catheter 916 would extend into the vascular system 24 (see FIGS. 30–31) in a manner similar to the manner in which catheter system 600 extends into the vascular system in FIG. 26. Further during use, a needle 918 would be advanced through the skin 20 and the subcutaneous tissue 22 and further through the septum 908 so as to position its distal end in the chamber 906 (see FIG. 31). During such advancement, the needle 918 would contact the funnel 907 so as to compress the spring 909 thereby causing a distal orifice of the retractable catheter 902 to be advanced out of a distal orifice of the guide catheter 916. Thereafter, fluid may be infused through the needle 918 into the vascular system 22 with the subcutaneous port catheter system 900. The needle 918 may then be withdrawn from the chamber 906 and removed from the body 14. Note that movement of the needle from the chamber 906 in the direction opposite to arrow 911 allows the spring 909 to move the funnel 907 back to its position shown in FIG. 30. Such movement of the funnel in 907 causes the distal orifice of the retractable inner catheter 902 to be advanced back within the interior of the guide catheter 916 as shown in FIG. 30.

Obviously, the subcutaneous port catheter system 900 may be modified in a similar manner to the modifications discussed above with respect to the abovedescribed single-lumen catheter system 600. For example, all the possible modifications and alternatives discussed above in the section entitled "*VII. Conclusion*" which relate to catheter system 600 are applicable to the catheter system 900.

In addition, the above-described dual-lumen catheter systems (e.g. catheter systems 12, 200, 300, 400, and 500) may be modified to incorporate any of the features of the subcutaneous port catheter system 900.

VIII(a). Catheter System 700

FIGS. 32–35 show yet another catheter system 700 which incorporates the features of the present invention therein. The catheter system 700 includes a guide catheter 702 and a retractable conduit assembly 704.

The retractable conduit assembly 704 includes a tube segment 705 through which fluid such as blood may be advanced. The tube segment includes a proximal orifice 708 and a distal orifice 728. The retractable conduit assembly 704 further includes a pusher 706 attached to the tube segment 705. The retractable conduit assembly 704 further includes a rotatable cap 710 which is attached to the pusher 706. The rotatable member 710 includes a set of internal threads 732.

Figure 33:
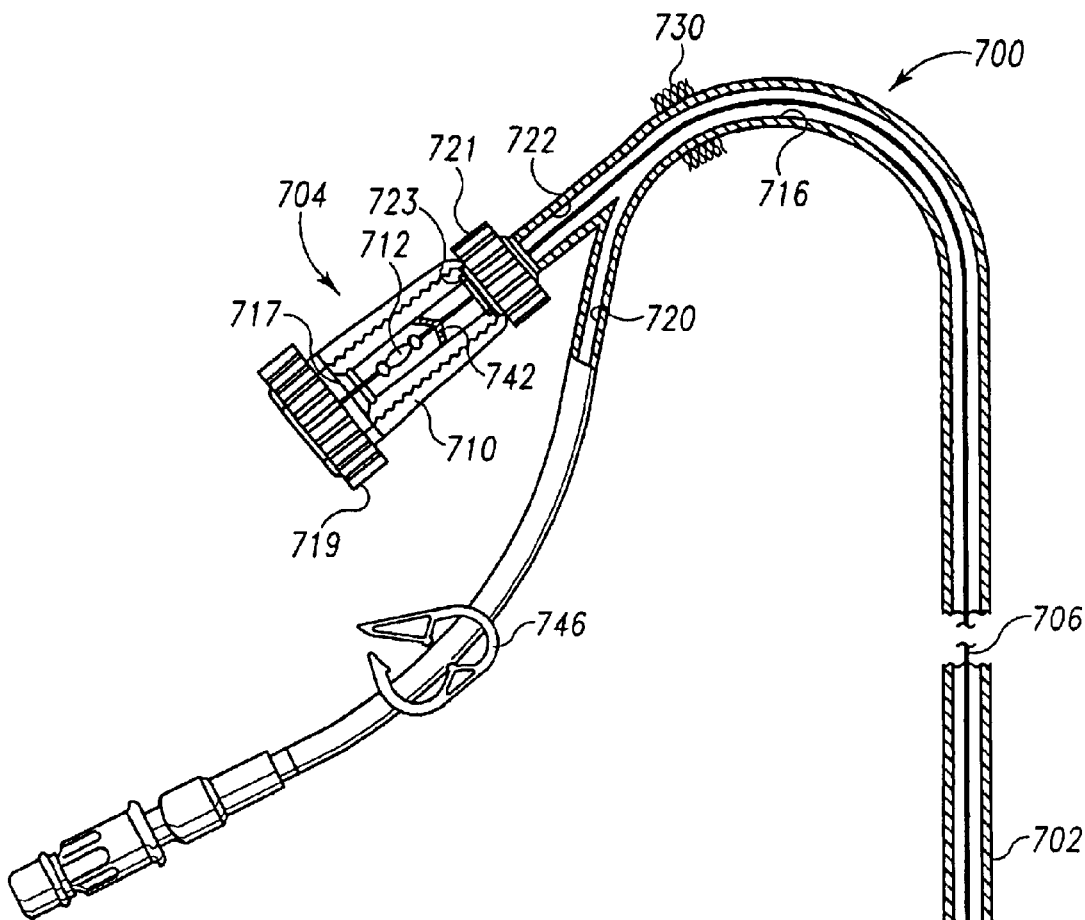
FIG. 33 is a view similar to FIG. 32, but showing the tube segment positioned in the operative position.
Figures 34, 35:
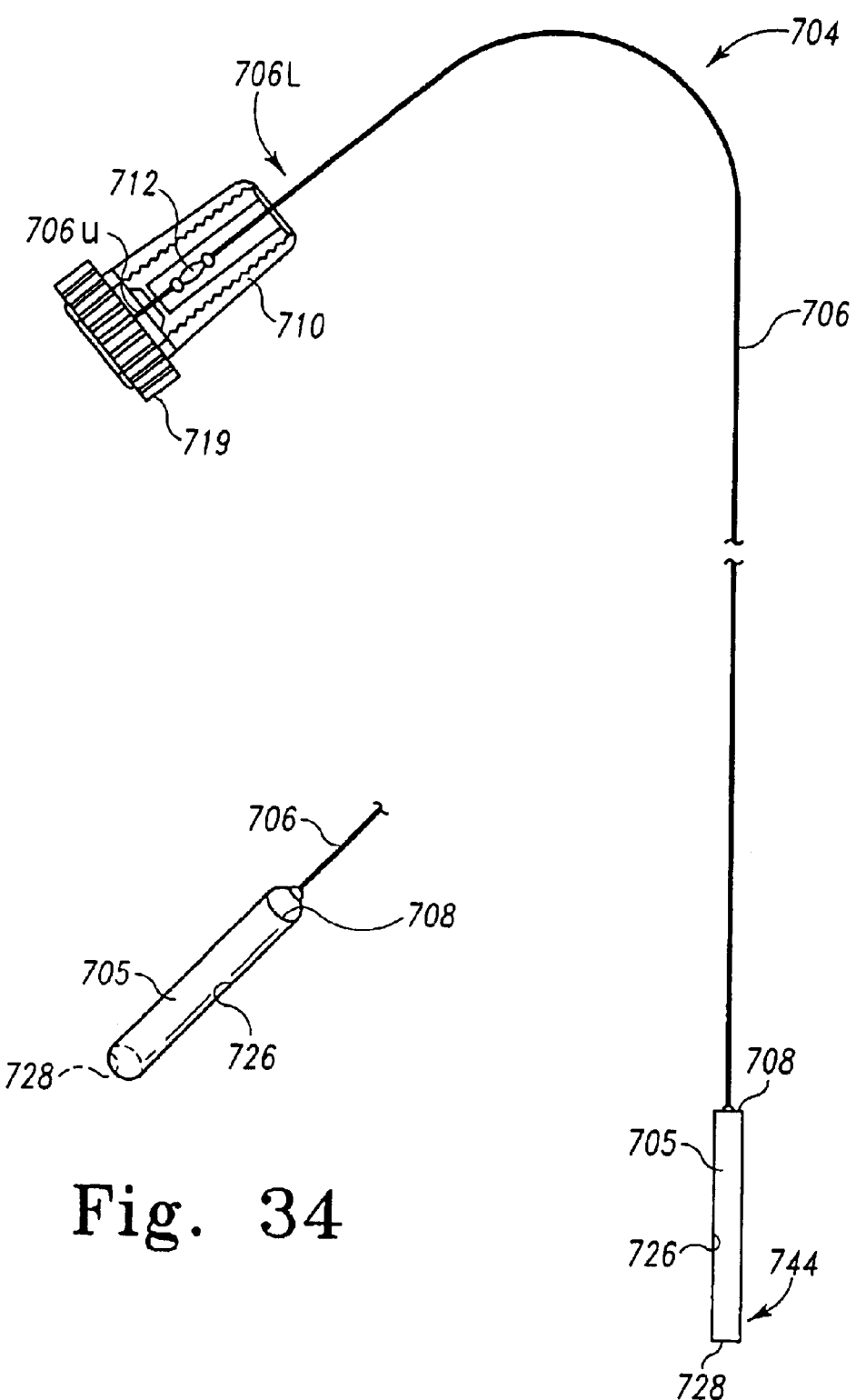
FIG. 34 is a perspective view of the tube segment of the retractable conduit assembly of FIG. 35.
FIG. 35 is a side elevational view of the retractable conduit assembly of the catheter system of FIG. 32.

The pusher 706 is attached to a sidewall of the tube segment as shown in FIG. 34 so as not to interfere with fluid flow entering or exiting a proximal orifice 708 of the tube segment 705. The pusher 706 may be made of a plastic member having sufficient beam strength to advance the tube segment 705 from its position shown in FIG. 32, through a portion of the guide catheter 702, and to its position shown in FIG. 33. Alternatively, the pusher 706 may be made from a metal wire such a guidewire which is commonly used to assist in the advancement of catheters within the vascular system of a patient. Of course, such metal wire would also need to possess sufficient beam strength to advance the tube segment 705 from its position shown in FIG. 32 to its position shown in FIG. 33.

The pusher 706 may include a swivel 712 interposed between an upper pusher portion 706U and a lower pusher portion 706L as shown in FIG. 35. The swivel 712 allows the upper pusher portion 706U to freely rotate relative to the lower pusher portion 706L. This feature allows the rotatable cap 710 to be easily rotated in relation to the guide catheter 702 so as to move the tube segment 705 between its position shown in FIG. 32 and its position shown in FIG. 33 without causing the lower pusher portion 706L to be rotated in a similar manner. The swivel 712 may be located at any position along the length of the pusher 706.

Figure 32:
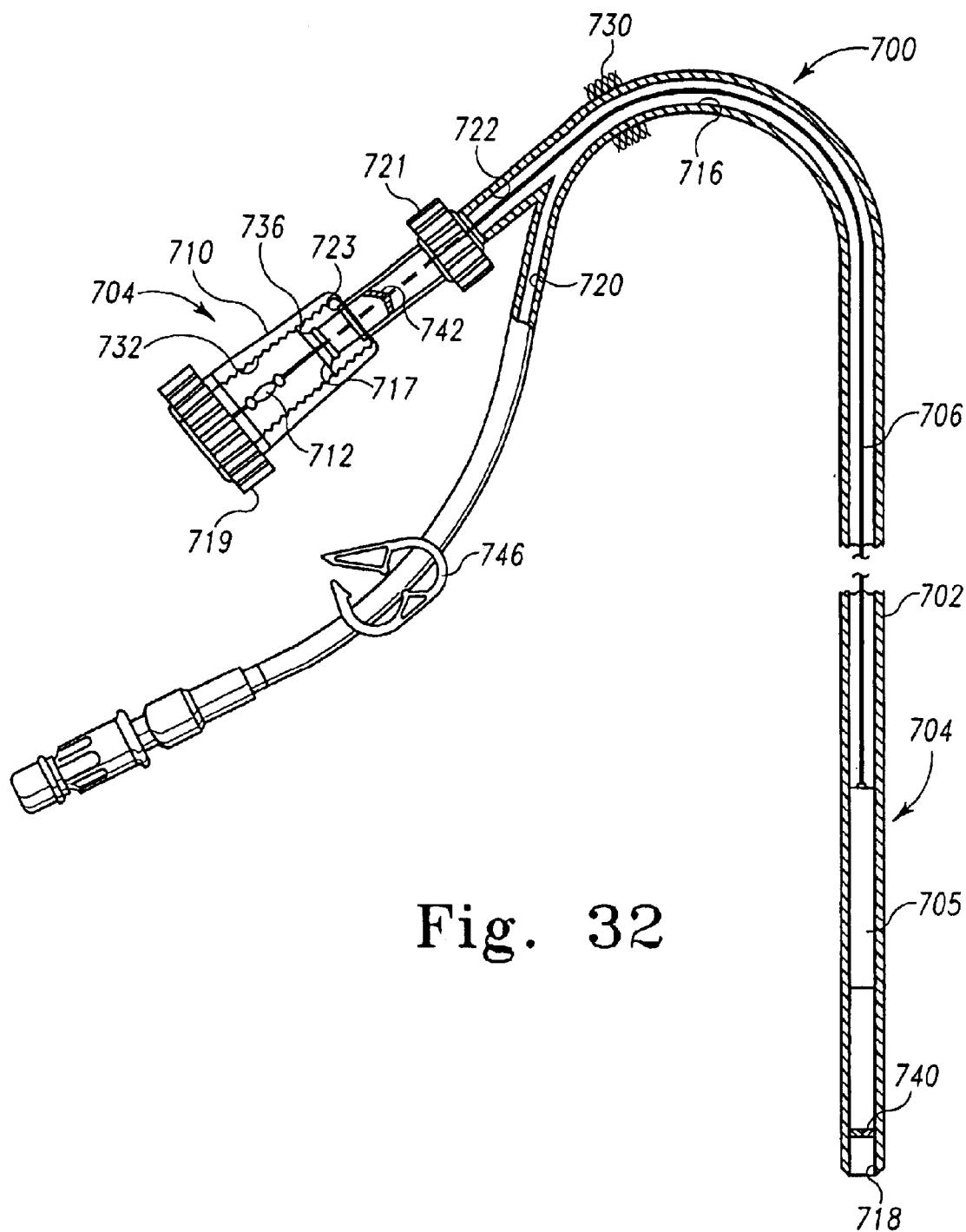
FIG. 32 is a view similar to FIG. 24, but showing another catheter system which incorporates the features of the present invention therein, and showing the tube segment positioned in the stowed position.

The guide catheter 702 has a common lumen 716 which extends through a lower portion of the guide catheter 702 as shown in FIGS. 32–33. The common lumen 716 defines a distal guide orifice 718. The guide catheter 702 further includes an upper main lumen 720 and a sideport lumen 722 as shown in FIGS. 32–33.

It should be appreciated that when the retractable conduit assembly 704 is located in its position shown in FIG. 33, fluid may be advanced through a flow path which includes (i) a proximal orifice 717 of the branch of the guide catheter 702 that defines the sideport lumen 722, (ii) the sideport lumen 722, (iii) the common lumen 716, (iv) the proximal orifice 708 of the tube segment 705, (v) a tube lumen 726 of the tube segment 705, and (vi) the distal orifice 728 of the tube segment 705.

According to one preferred manner of using the catheter system 700, the tube segment 705 of the retractable conduit assembly 704 is initially located entirely within the guide catheter 702 as shown in FIG. 32. (Note that FIG. 32 shows the catheter system 700 located in a retracted or stowed position). Thereafter, it may be desirable to perform a medical procedure, such as a TPN administration session. In order to perform such a procedure, the retractable conduit assembly 704 must be moved from its position shown in FIG. 32 to its position shown in FIG. 33. (Note that FIG. 33 shows the catheter system 700 located in an extended or operative position). In order to achieve such movement, the rotatable cap 710 is continuously rotated by a user in a first direction until it moves from its position shown in FIG. 32 to its position shown in FIG. 33. Note that such movement is achieved due to the cooperation of the set of internal threads 732 of the rotatable member 710 and a proximal flange 736 defined on the guide catheter 702 at the proximal orifice 717. The rotatable cap 710 is provided with a gripping member 719 to facilitate rotation of the rotatable member 710 by the user. Further, a stop 721 is provided on the guide catheter 702 to limit rotation of the rotatable cap 710. Also, the rotatable cap 710 is provided with a retaining ring 723 which functions to prevent the rotatable cap 710 from becoming separated from the guide catheter 702 due to over rotation of the rotatable cap 710 in relation to the guide catheter 702. After the retractable conduit assembly 704 is moved to its position shown in FIG. 33, the medical procedure (such as a TPN administration session) is performed. After the TPN administration session is completed, the retractable conduit assembly 704 is moved back to its position shown in FIG. 32. Of course, in order to achieve such movement, the rotatable cap 710 is continuously rotated (in a direction opposite to the first direction) until it moves from its position shown in FIG. 33 to its position shown in FIG. 32.

Referring again to FIGS. 32 and 33, the guide catheter 702 has a tissue ingrowth member 730 secured to an outer surface thereof. Tissue ingrowth member 730 is substantially identical to tissue ingrowth member 38 described hereinabove with regard to the catheter system 12.

While FIGS. 32–35 show one particular type of mechanism to lock the retractable conduit assembly 704 to the guide catheter 702 in either its stowed position as shown in FIG. 32 or its operative position as shown in FIG. 33, many other types of locking mechanisms may be used to carry out the present invention. For example, any of the plurality of locking mechanisms 56 described hereinabove with regard to the catheter system 12 may be used to lock the retractable conduit assembly 704 to the guide catheter 702 in either its stowed position as shown in FIG. 32 or its operative position as shown in FIG. 33.

The guide catheter 702 further includes a distal blood flow valve 740 positioned within the common lumen 716, and a proximal blood flow valve 742 positioned within the sideport lumen 722 as shown in FIGS. 32–33. The blood flow valves 740 and 742 are substantially identical to the blood flow valves 37 and 39 which were described hereinabove with regard to the catheter system 12.

Referring again to FIGS. 32–35, the tube segment 705 of the retractable conduit assembly 704 defines the tube lumen 726 through which fluid is advanced. The tube lumen 726 defines the proximal orifice 708 and the distal orifice 728. The distal orifice 728 is defined in a distal portion 744 of the tube segment 705.

A clamp 746 is positioned on the guide catheter 702 which functions to prevent fluid flow through the upper main lumen 720 when desired. The clamp 746 is substantially identical in construction and function to the clamps 62, 64 discussed hereinabove with regard to the catheter system 12.

The catheter system 700 is placed within the body 14 in substantially the same manner as was described hereinabove with respect to the placement of the catheter system 12 within the body 14 (e.g. by the tunneled catheter technique). While in the body 14, the locking structure possessed by the retractable conduit assembly 704 and the guide catheter 702 functions to lock the retractable conduit assembly 704 to the guide catheter 702 in either its stowed position (FIG. 32) or its operative position (FIG. 33).

It should be appreciated that FIG. 32 shows the retractable conduit assembly 704 locked to the guide catheter 702 in the stowed position. While the retractable conduit assembly 704 is locked in the stowed position in the patient's body 14 between TPN administration sessions, the distal orifice 728 of the tube segment 705 would be isolated from contact with the blood flow in the superior vena cava 32. FIG. 33 shows the retractable conduit assembly 704 locked to the guide catheter 702 in the operative position. While the retractable conduit assembly 704 is locked in the operative position during performance of a TPN administration procedure, the distal orifice 728 of the tube segment 705 would be positioned within the blood flow in the superior vena cava 32.

Also, please note that the tube segment 705 of the catheter system 700 contacts the blood located in the vascular system 24 for a substantially reduced amount of time in comparison to the amount of time a conventional catheter (which is used for TPN administration) is contacted by blood located in the vascular system. Accordingly, the physical structure of the tube segment 705 of the catheter system 700 may be substantially the same or similar to the physical structure of a conventional short-term catheter for the same reasons hereinabove discussed in regard to the dialysis catheter 42 of the catheter system 12 in section 1(b) entitled "Performance of a Dialysis Session with the Catheter System 12".

VIII(b). Further Discussion Regarding Catheter System 700

The catheter system 700 may be modified in a similar manner to the modifications discussed above with respect to the catheter system 600. In particular, the modifications and alternatives of the catheter system 600 discussed above with respect to the catheter system 600' is applicable to the catheter system 700. Moreover, all the possible modifications and alternatives discussed above in the section entitled "*VII. Conclusion*" which relate to catheter system 600, and 600' are applicable to the catheter system 700.

In addition, certain of the above-described dual-lumen catheter systems (e.g. catheter systems 12, 200, 300, 400, and 500) may be modified to incorporate the features of the catheter system 700. For example, the catheter system 400 may be modified to utilize a retractable conduit assembly similar to the retractable conduit assembly 704 instead of utilizing working catheter 404. Of course, the guide catheter 402 would need to be modified to include a sideport lumen which would extend from the branch of the guide catheter 402 in which the proximal valve 424 is located.

It should be appreciated that catheter systems 12, 200, 300, 400, 500, 600, 600', and 700 set forth at different locations above are configured and used accordingly to a common theme. Such common theme is to provide a catheter system which includes some type of conduit having a distal orifice through which fluid can be advanced, wherein the distal orifice can be directly exposed to blood in the vascular system (or other bodily fluids outside of the vascular system) during a medical procedure, and thereafter the distal orifice can be shielded by a protective structure whereby the distal orifice of the conduit is not directly exposed to blood in the vascular system (or other bodily fluids outside of the vascular system) when a medical procedure is no longer being performed by the catheter system, but yet when the catheter system is still located within the body (e.g. the vascular system) for a period of time (e.g. for several weeks or months as is the common time period in the case of a long term catheter system). For example, in the case of the catheter system 12 of FIGS. 1–11, the conduit is the catheter 42, while in the case of the catheter system 700 of FIGS. 32–35, the conduit is the tube segment 705. In both of these cases, selective shielding of the distal orifice of the conduit 42, 705 from bodily fluid, such as blood in the vascular system, effectively and conveniently reduces the likelihood that the partial or total occlusion of the fluid path of the respective catheter system would occur due to, for example, blood clot buildup.

IX. Catheter System 800

Another catheter system 800 which incorporates the features of the present invention therein is shown in FIGS. 36, 36A–B, 37, 37A, 38A, 38B, 39, 39A–C, 40, and 40A–D. The catheter system 800 includes a guide catheter 34 (see FIG. 36) and a working catheter 42 (see FIG. 37). The catheter system 800 is somewhat similar to the catheter system 12. Thus, the same reference numerals are used in FIGS. 36, 36A–B, 37, 37A, 38A, 38B, 39, 39A–C, 40, and 40A–D to designate common components which were previously discussed with regard to FIGS. 1–11. Moreover, the description of the components of the catheter system 800 which are common to the catheter system 12 will not be undertaken since they are designated with common reference numerals and such components have been previously described hereinabove. In addition, the guide catheter 34 of the catheter system 800 is placed within the body 14 in substantially the same manner as was described hereinabove with respect to the placement of the guide catheter 34 of the catheter system 12 within the body 14 (e.g. by the tunneled catheter technique).

However, the catheter system 800 differs from the catheter system 12 in that the guide catheter 34 of the catheter system 800 does not possess a distal blood flow valve positioned within the guide lumen 36. Rather, the guide catheter 34 of the catheter system 800 includes a duckbill valve 802 positioned external to the guide lumen 34 just below the distal guide orifice 40 as shown in FIG. 36.

Figures 36, 36A:
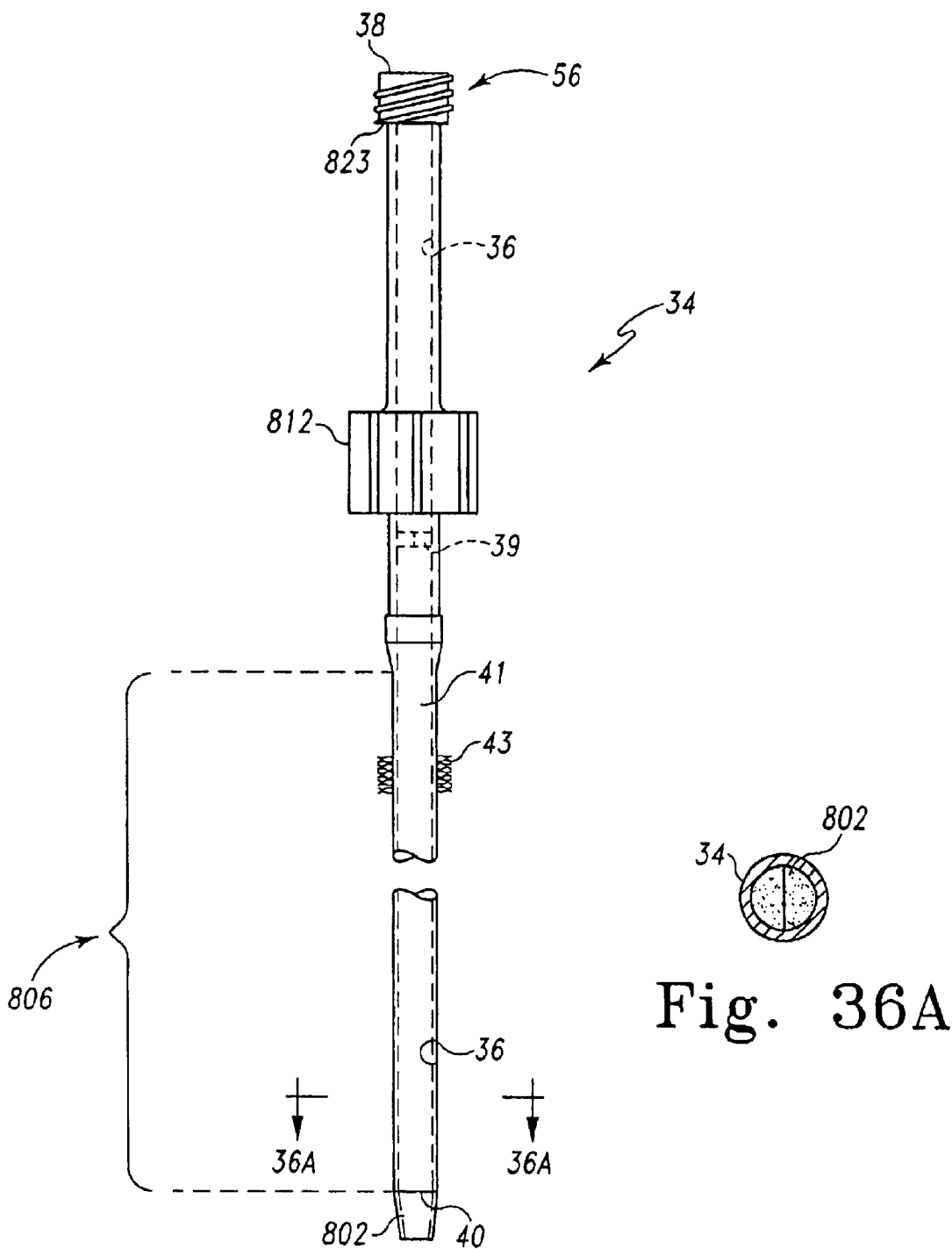
FIG. 36 is an enlarged side elevational view of the guide catheter of the long-term dialysis catheter system shown in FIG. 38A.
FIG. 36A is an enlarged cross sectional view of the guide catheter taken along the line 36A—36A of FIG. 36 as viewed in the direction of the arrows.
Figure 36B:
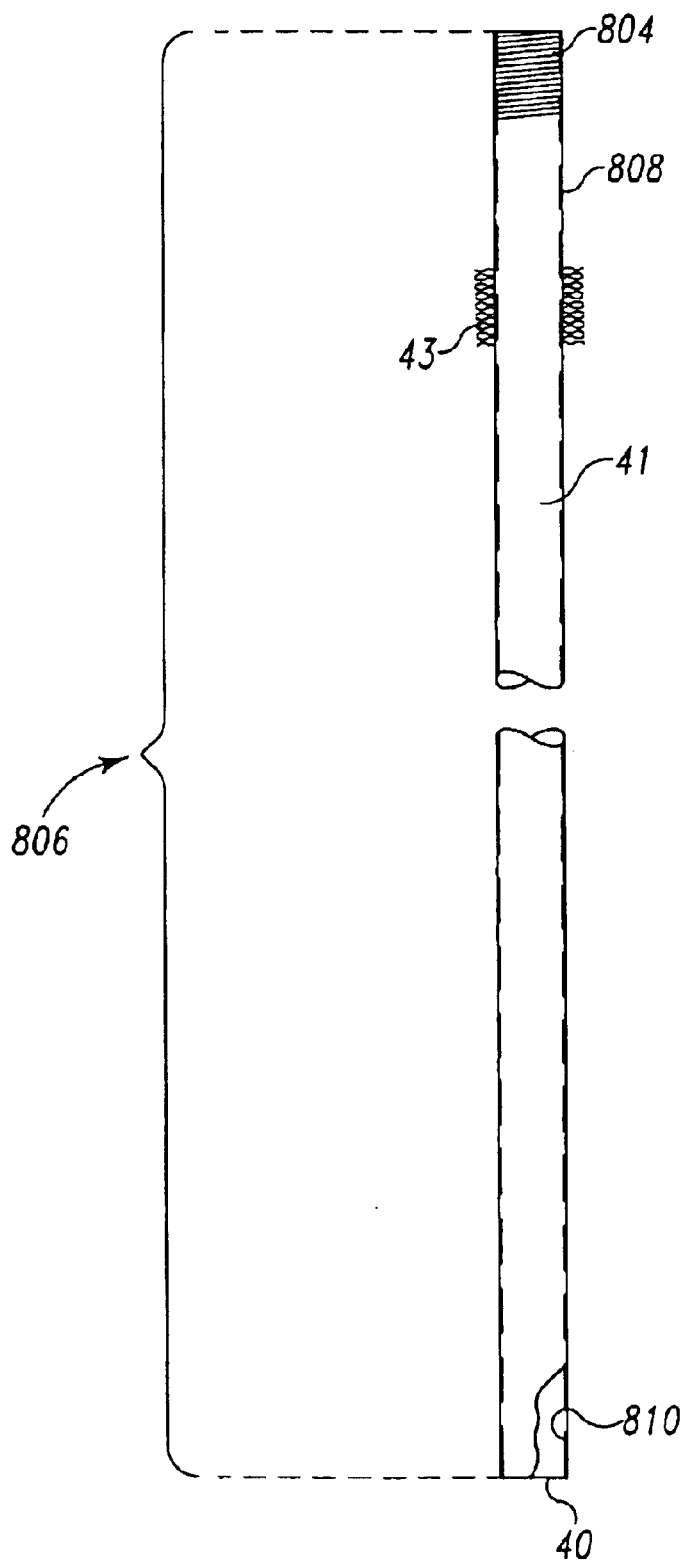
FIG. 36B is an enlarged side elevational view of a portion of the guide catheter of FIG. 36.
Figure 38A:
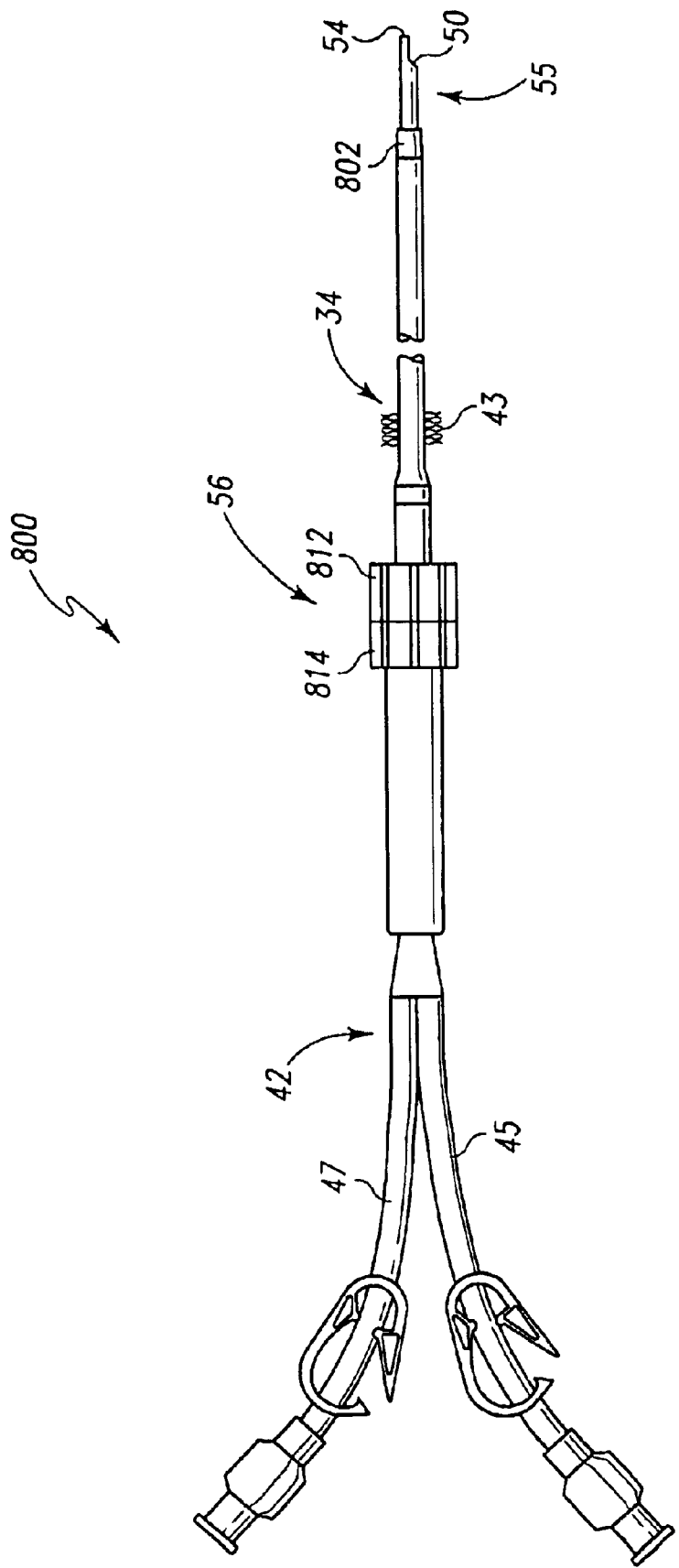
FIG. 38A is a view similar to FIG. 3, but showing another catheter system which incorporates the features of the present invention therein, with the working catheter shown positioned in the operative position.
Figure 38B:
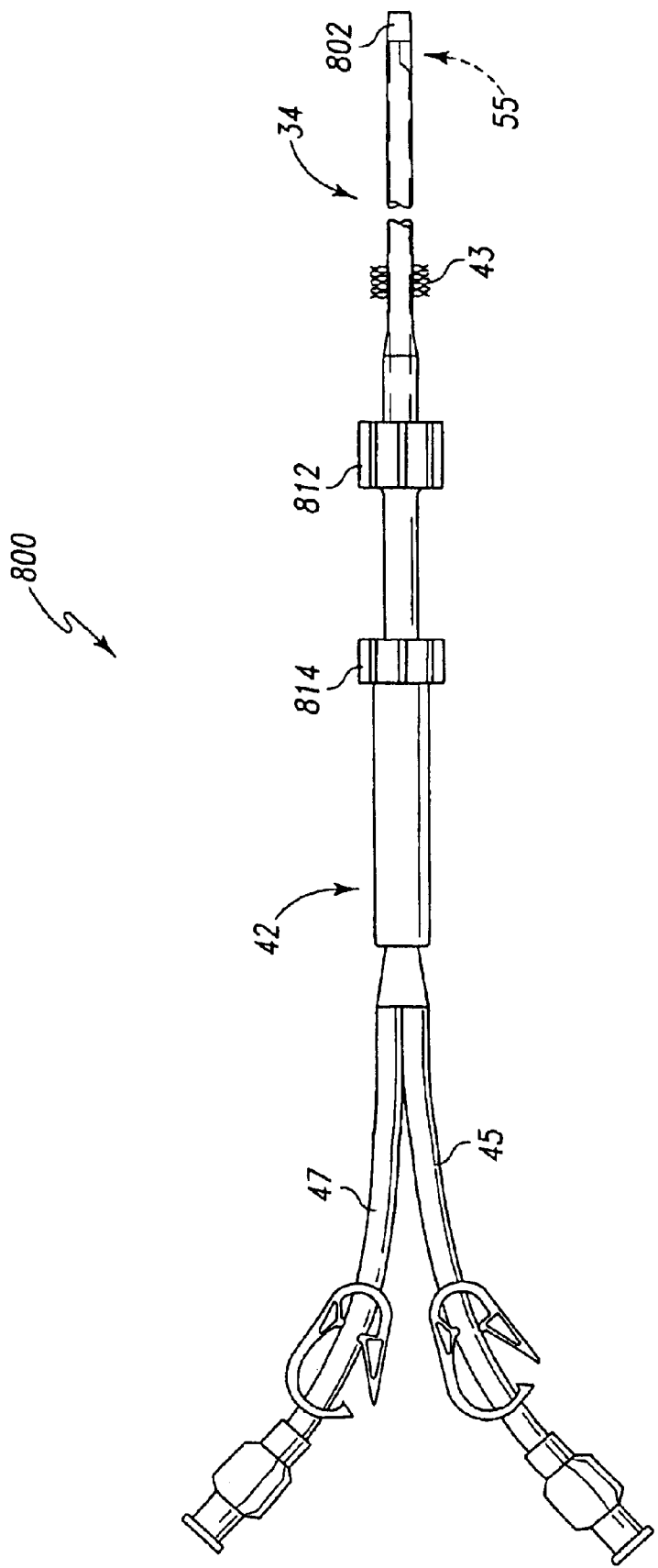
FIG. 38B is a view similar to FIG. 38A, but showing the working catheter positioned in the stowed position.

Another difference between the catheter system 800 and the catheter system 12 is that the guide catheter 34 of the catheter system 800 includes a stainless steel wire coil 804 which is cylindrically wound and extends the entire length of a segment 806 of the guide catheter 34 as shown in FIGS. 36 and 36B. Note that for clarity of description only a proximal portion of the segment 806 is shown possessing the wire coil 804. Further, the entire outer surface of the segment 806 of the guide catheter 34 has positioned thereon a nylon material 808 such as PEBAX. PEBAX is a tradename, commonly known to one skilled in the art, for a type of nylon polymer which is commonly used in the medical device industry for the manufacture of catheters. Moreover, the inner surface of the guide catheter 34 of the catheter system 800 which defines the guide lumen 36 may have positioned thereon a Teflon coating 810. The Teflon coating 810 may facilitate sliding of the working catheter 42 relative to the guide catheter 34 during movement of the working catheter between its operative position (shown in FIG. 38A) and its stowed position (shown in FIG. 38B).

Alternatively, instead of the wire coil 804 being made of stainless steel, the wire coil 804 may be made from another metallic material such as NITINOL. NITINOL is a tradename, commonly known to one skilled in the art, for a type of metallic material that is commonly used in the medical device industry in the manufacture of medical devices. The thickness (i.e. the outer diameter) of the strand of wire that makes up the wire coil 804 may be uniform as it extends from the proximal end of the segment 806 to the distal end of the segment 806. Alternatively, certain portion(s) of the strand of wire which makes up the wire coil 804 may possess a first larger thickness while other portion(s) may possesses a second smaller thickness. For example, the strand of wire that makes up the wire coil 804 which is required to be bent into a U-shaped orientation when the guide catheter 34 of the catheter system 12 is implanted in the patient's body 14 (see e.g. FIG. 9) may possess the first larger thickness, while the strand of wire that makes up the wire coil 804 which is linearly oriented on each side of the U-shaped portion may possess the second smaller thickness. This variation in the thickness of the strand of wire that makes up the wire coil 804 may reduce the likelihood of kinking or other deformation of the guide catheter 34 during implantation and use of the guide catheter 34. Also, it should be noted that the more tightly the strand of wire which makes up the wire coil 804 is wound (i.e. the more turns per linear inch), the less likely the guide catheter 34 will kink or otherwise deform during implantation and use of the guide catheter 34.

Still another difference between the catheter system 800 and the catheter system 12 is that the locking mechanism 56 of the catheter system 800 has a somewhat different physical configuration when compared to the locking mechanism 56 of the catheter system 12. In particular, FIGS. 36, 36A–B, 37, 37A, 38A and 38B show the physical configuration of the locking mechanism 56. One point of distinction is that each of the locking component of the guide catheter 34 and the locking component of the working catheter 42 possesses finger grips. More specifically, the locking component of the guide catheter 34 possesses a first finger grip 812, while the locking mechanism of the working catheter 42 possesses a second finger grip 814. These grips form the basis of a supplemental locking system 816 and facilitate user actuation of the working catheter 42 between its operative position (shown in FIG. 38A) and its stowed position (shown in FIG. 38B).

The locking component of the working catheter 42 includes a retaining ring 819 positioned within such locking component near the finger grip 814 as shown in FIG. 37. The retaining ring 819 functions to prevent the locking component of the working catheter 42 from becoming separated from the locking component of the guide catheter 34 due to over rotation between these two components. For example, if the working catheter 42 is advanced from its position shown in FIG. 38A to its position shown in FIG. 38B, further advancement in such direction is prevented due to contact between a shoulder 823 of the guide catheter 34 (see FIG. 36) and the retaining ring 821 of the working catheter 42 (see FIG. 37).

Turning to the supplemental locking system 816, each of the finger grips 812, 814 have a plurality of grooves 818 defined therein (see FIG. 39). The supplemental locking system 816 includes a locking clip 820 having a pair of nubs 822 as shown in FIGS. 39A, 39B, and 39C. In order to further lock the working catheter 42 in a fixed position relative to the guide catheter 34, the locking clip 820 is applied over the finger grips 812, 814 when the grooves 818 of the first finger grip 812 are aligned with the grooves 818 of the second finger grip 814 as shown in FIG. 39. When so aligned, the nubs 822 are received into the grooves 818 of finger grips 812, 814 as shown in FIG. 39C so as to prevent relative rotation between the working catheter 42 and the guide catheter 34.

Another supplemental locking system 824 is shown in FIGS. 40, 40A, 40B, 40C, and 40D. The supplemental locking system 824 includes a slider 826 which is securely positioned within a first recess 828 defined in the first finger grip 812 and a second recess 830 defined in the second finger grip 814. When the slider 826 is moved to its leftmost position in the direction of arrow 832, the working catheter 42 can be rotated in relation to the guide catheter 34. When the slider 826 is located in its position as shown in FIG. 40, the slider 826 prevents rotation of the working catheter 42 in relation to the guide catheter 34.

Yet another distinction between the catheter system 800 and the catheter system 12 is that the working catheter 42 includes a first segment 815 which possesses a first degree of hardness (having a first durometer rating), and a second segment 817 which possesses a second degree of hardness (having a second durometer rating) as shown in FIG. 37. Providing the first segment 815 with relatively increased hardness may facilitate the slidability of the working catheter 42 in relation to the guide catheter 34. The difference in the degree of hardness between the first segment 815 and the second segment 817 may be created by manufacturing the first segment 815 with a first material possessing a first resin-to-nylon content ratio, while manufacturing the second segment 817 with a second material possessing a second resin-to-nylon content ratio which is different from the first resin-to-nylon content ratio. Note that the degree of hardness of a catheter depends on the percentage of resin used in comparison to the percentage of nylon used in the manufacturing process of the catheter. Resin is a filler material. The more resin used, the softer the catheter. The more nylon used, the harder the catheter. A catheter can be made of two different segments having different degrees of hardness by thermally fusing the two catheter segments together at a transition area. This transition area may be located at any position along the length of the catheter. With regard to catheter system 800, the first segment 815 of the working catheter 42 could be configured to possess a higher degree of hardness in order to provide better slidability of the working catheter 42 in relation to the guide catheter 34. Moreover, since the distal end segment of the working catheter 42 possesses a lesser degree of hardness, such distal end is advantageously softer in order to minimize trauma to the vascular system in which it is used. For example, the distal end segment of the working catheter 42 which is advanced out of the distal guide orifice 40 of the guide catheter 34 according to one preferred method of the present invention would possess a relatively soft configuration in order to minimize trauma to the vascular system 24.

Alternatively, the original dialysis catheter 42 may be manufactured such that its first segment 815 and its second segment 817 possess an identical degree of hardness (or identical durometer rating).

Obviously, the catheter system 800 may be modified in a similar manner to the modifications discussed above with respect to the above-described duallumen catheter systems (e.g. catheter systems 12, 200, 300, 400, and 500). For example, all the possible modifications and alternatives discussed above in the section entitled "VII. Conclusion" which relate to catheter system 12, 200, 300, 400, and 500 are applicable to the catheter system 800.

In addition, the above-described dual-lumen catheter systems (e.g. catheter systems 12, 200, 300, 400, and 500) and the single lumen catheter systems (e.g. catheter systems 600, 600', 700 and 900) may be modified to incorporate any of the features of the catheter system 800.

X. Catheter System 1000

Another catheter system 1000 which incorporates the features of the present invention therein is shown in FIGS. 41–45. The catheter system 1000 includes a retractable sheath assembly 1034 and a working catheter 1042 which are attached together. The working catheter 1042 of the catheter system 1000 is somewhat similar to the working catheter 42 of the catheter system 12. Thus, many of the same reference numerals are used in FIGS. 41–45 to designate common components of the working catheters 42, 1042 which were previously discussed with regard to FIGS. 1–11. Moreover, the description of the components of the working catheter 1042 of the catheter system 1000 which are common to the catheter system 12 will not be undertaken since they are designated with common reference numerals and such components have been previously described hereinabove. In addition, the guide catheter 1034 of the catheter system 1000 is placed within the body 14 in substantially the same manner as was described hereinabove with respect to the placement of the guide catheter 34 of the catheter system 12 within the body 14 (e.g. by the tunneled catheter technique).

However, the catheter system 1000 differs from the catheter system 12 in that the catheter system 1000 does not possess a guide catheter exactly the same as the guide catheter 34 of the catheter system 12, but rather possesses the retractable sheath assembly 1034. The retractable sheath assembly 1034 includes an outer guide tube 1036 and an inner retractable conduit 1038. The outer guide tube 1036 includes a tissue ingrowth member 1043 secured to an outer surface thereof. Tissue ingrowth member 1043 is substantially identical to tissue ingrowth member 43 described hereinabove with regard to the catheter system 12.

Figure 41:
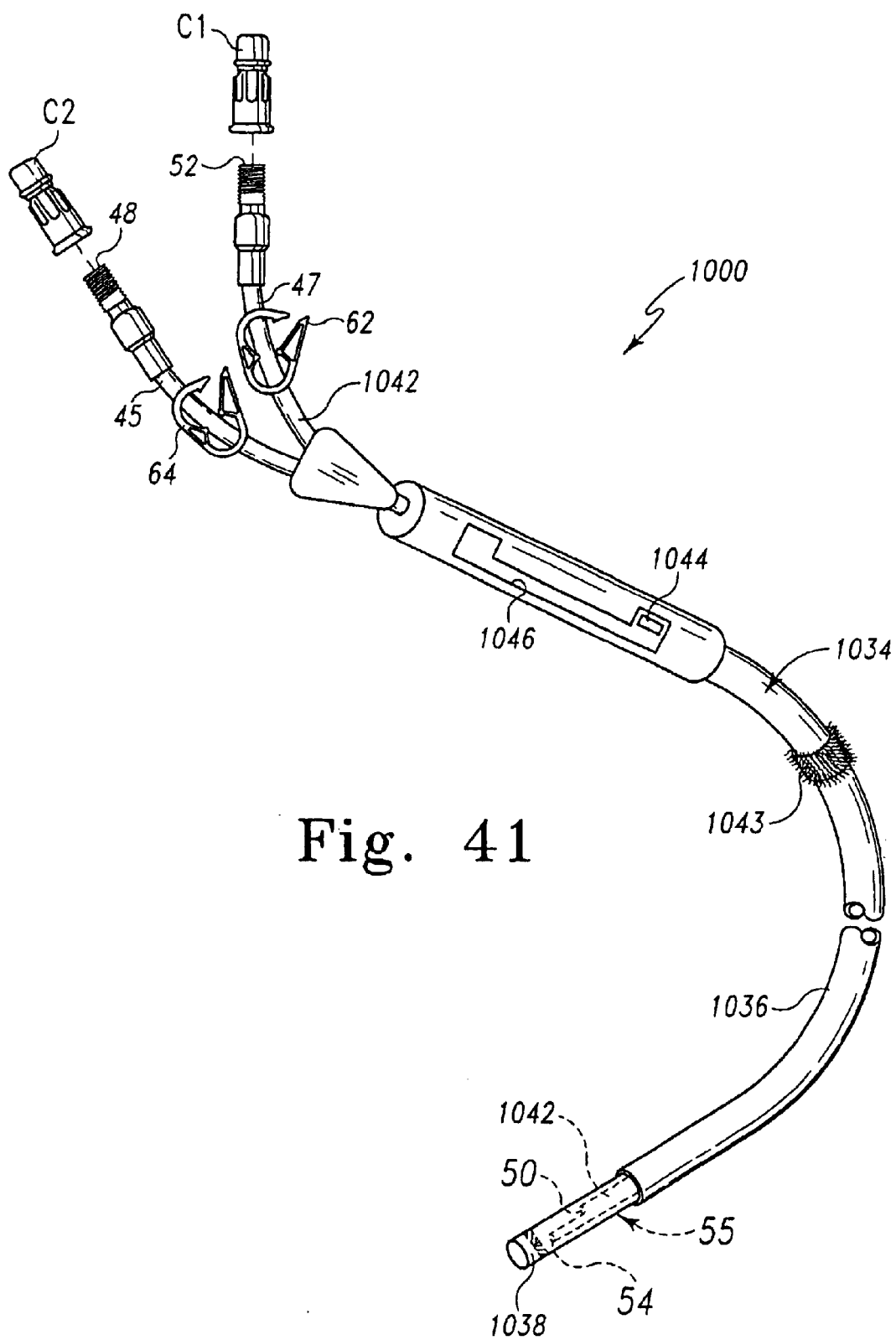
FIG. 41 is a view similar to FIG. 3, but showing another catheter system which incorporates the features of the present invention, with the catheter system being shown in a stowed position.
Figure 42:
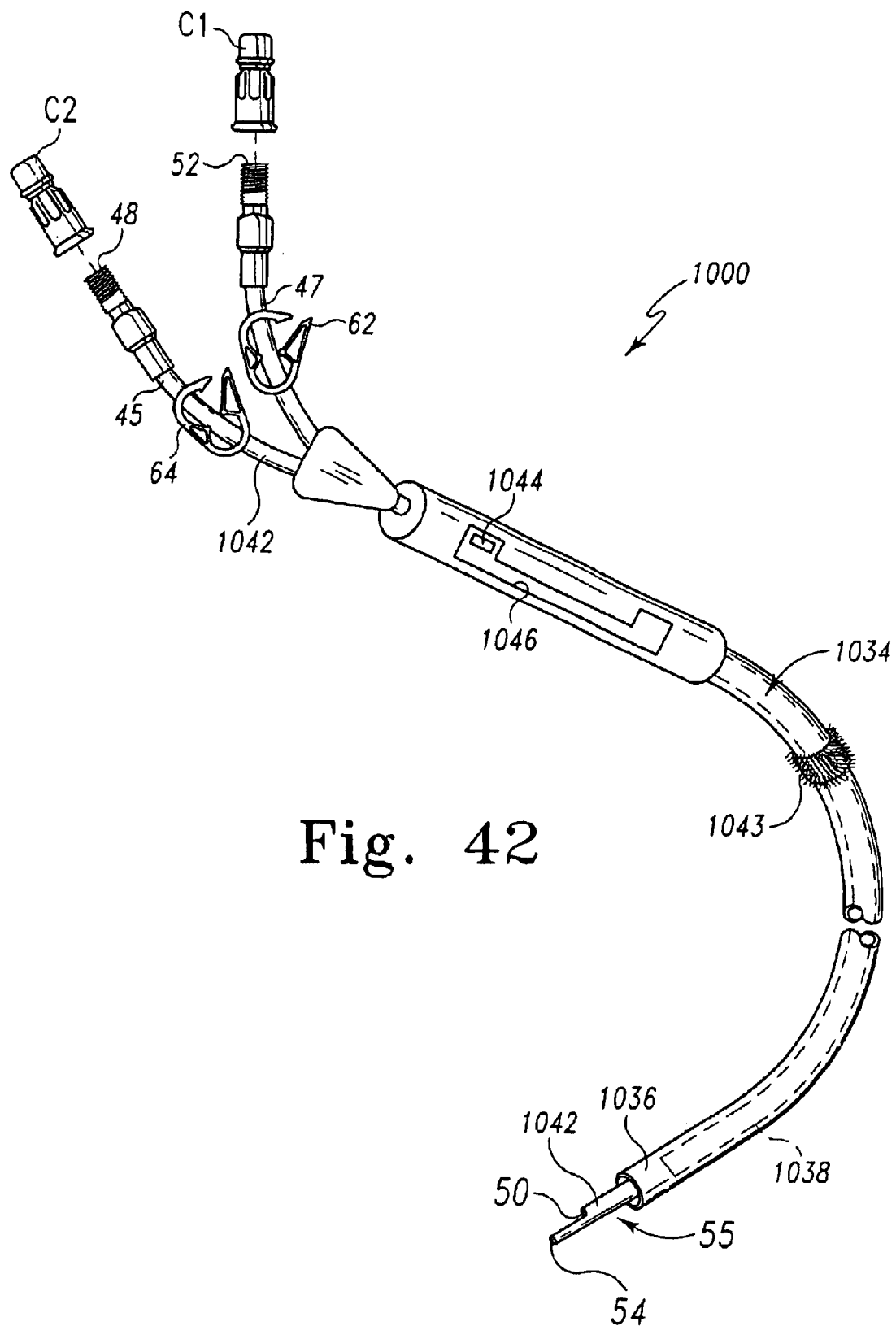
FIG. 42 is a view similar to FIG. 41, but showing the catheter system being shown in a operative position.
Figure 43:
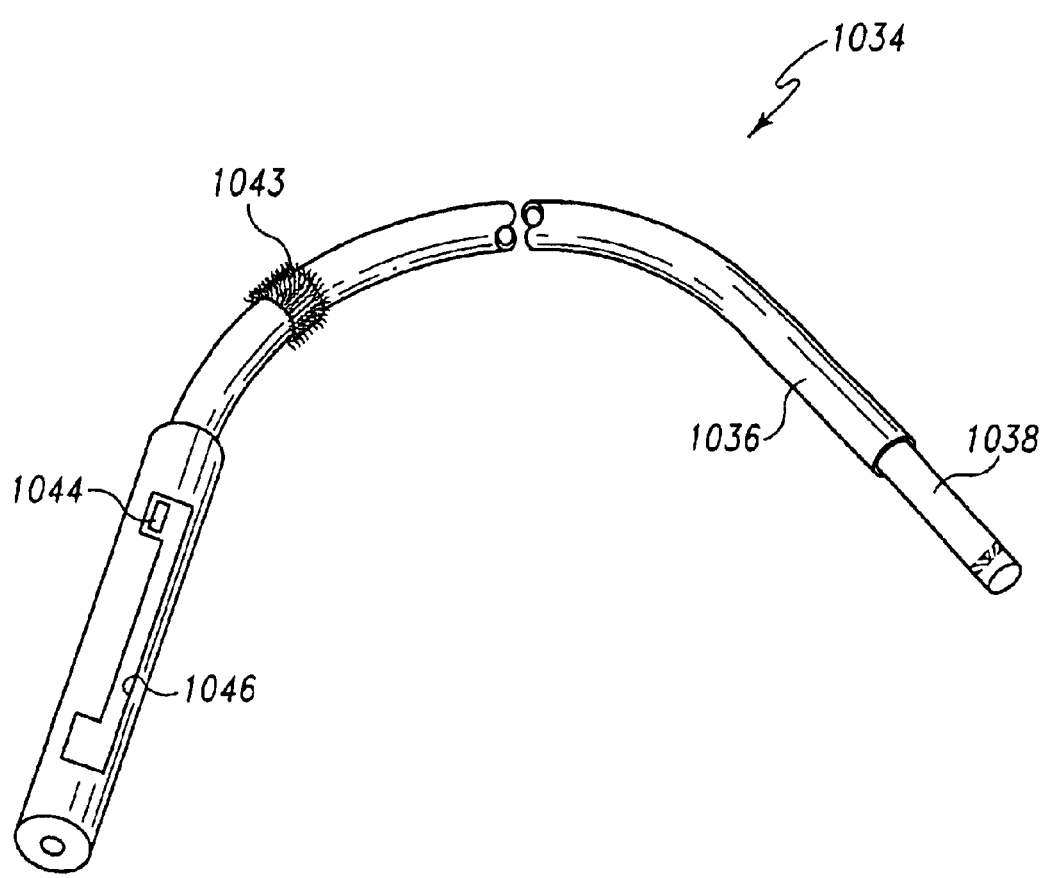
FIG. 43 is a side elevational view of the retractable sheath assembly of the catheter system of FIG. 41, and showing the inner retractable conduit extending outside of the outer guide tube.
Figure 44:
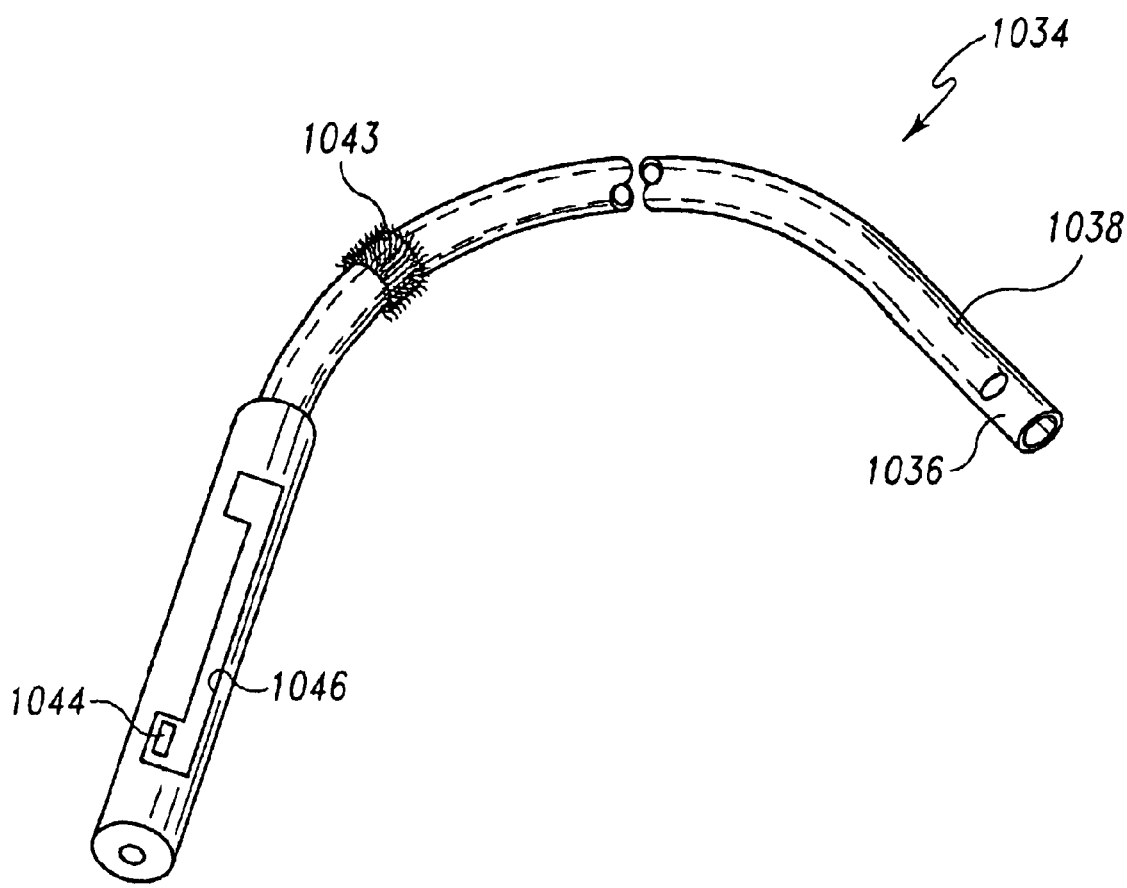
FIG. 44 is a view similar to FIG. 43, but showing the inner retractable conduit positioned within the outer guide tube.
Figure 45:
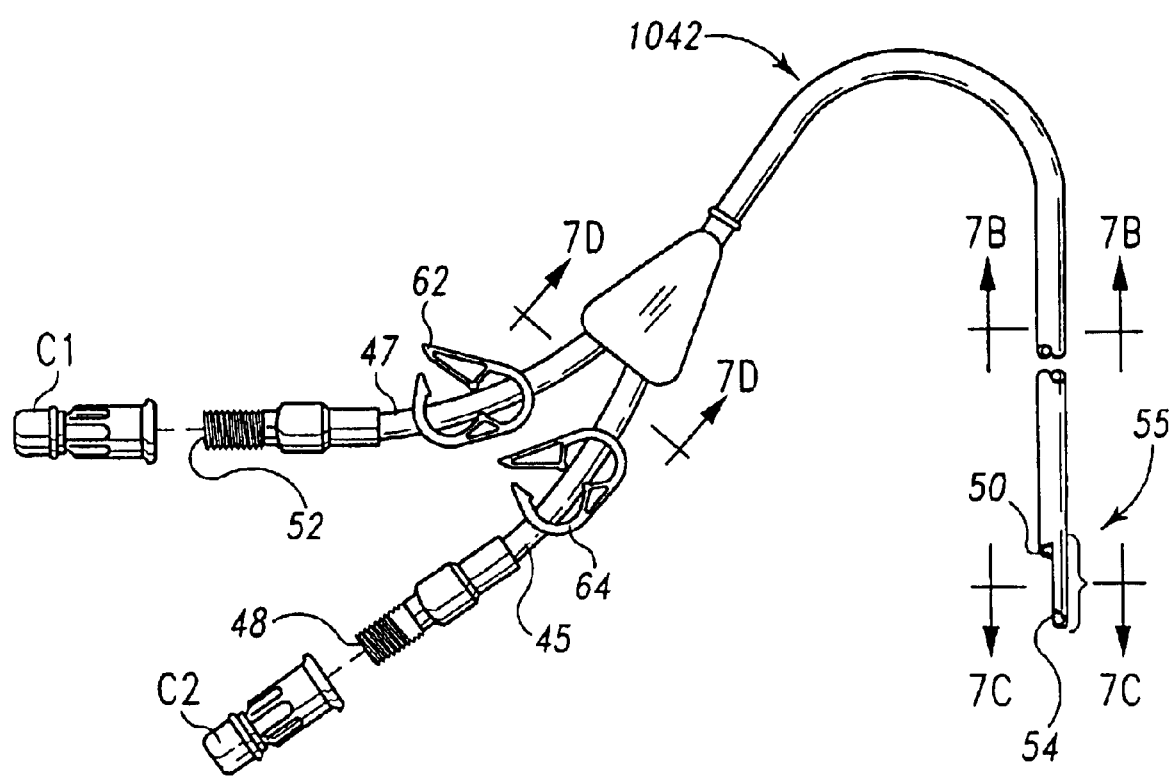
FIG. 45 is an elevational view of the working catheter of the catheter system of FIG. 41.

It should be appreciated that the inner retractable conduit 1038 is movable in relation to the guide tube 1036 from its position shown in FIG. 41 (see also FIG. 43) to its position shown in FIG. 42 (see also FIG. 44). Note that during operation of the catheter system 1000, the working catheter 1042 is fixed in relation in relation to the outer guide tube 1036 (e.g. the working catheter 1042 does not move axially in relation to the outer guide tube 1036). Rather, in order to shield the distal orifices 50, 54 so that such distal orifices are not directly exposed to blood in the vascular system 24 (or other bodily fluids outside of the vascular system) when a medical procedure is no longer being performed by the catheter system 1000, the inner retractable conduit 1038 is movable in relation to the working catheter 1042 (and also in relation to the guide tube 1036). In particular, the inner retractable conduit 1038 is movable from its position shown in FIG. 41 (in which it effectively stows the distal working segment 55 of the working catheter 1042 therein) to its position shown in FIG. 42 (in which it is withdrawn within the outer guide tube 1036 so as to expose the distal working segment 55 of the working catheter 1042 in order for a medical procedure to be performed on the patient (e.g. a dialysis procedure).

The retractable sheath assembly 1034 includes an actuator 1044 which is mechanically coupled to the retractable inner conduit 1038. Movement of the actuator 1044 from its position shown in FIG. 41 to its position shown in FIG. 42 causes the retractable inner conduit 1038 to move from its position shown in FIG. 41 to its position shown in FIG. 42. In order to guide movement of the actuator 1044, a guide slot 1046 is provided in the outer guide tube 1036.

One or more supplemental locking mechanisms (not shown) may be used to further lock the actuator 1044 at either of its positions shown in FIGS. 41–42.

The catheter system 1000 may be used to perform any of the medical procedures described hereinabove as being performed by the catheter system 12 including but not limited to dialysis procedures. Moreover, the catheter system 1000 may be modified in a similar manner to the modifications discussed above with respect to the above-described dual-lumen catheter systems (e.g. catheter systems 12, 200, 300, 400, 500, and 800) For example, all the possible modifications and alternatives discussed above in the section entitled "*VII. Conclusion*" which relate to catheter systems 12, 200, 300, 400, and 500 are applicable to the catheter system 1000.

In addition, the above-described dual-lumen catheter systems (e.g. catheter systems 12, 200, 300, 400, 500, 800) and the single lumen catheter systems (e.g. catheter systems 600, 600', 700, and 900) may be modified to incorporate any of the features of the catheter system 1000. Alternatively, the catheter system 1000 may be modified to incorporate any of the features of the catheter systems 12, 200, 300, 400, 500, 600, 600', 700, 800, and 900.

Moreover, it should be appreciated that any one of the catheter systems 12, 200, 300, 400, 500, 600, 600', 700, 800, 900 1000 described in this document may incorporate any one or more features of another catheter system (i.e. 12, 200, 300, 400, 500, 600, 600', 700, 800, 900 1000) described in this document.

XI. Hybrid Removable/Retractable Catheter System 1200

Figure 46:
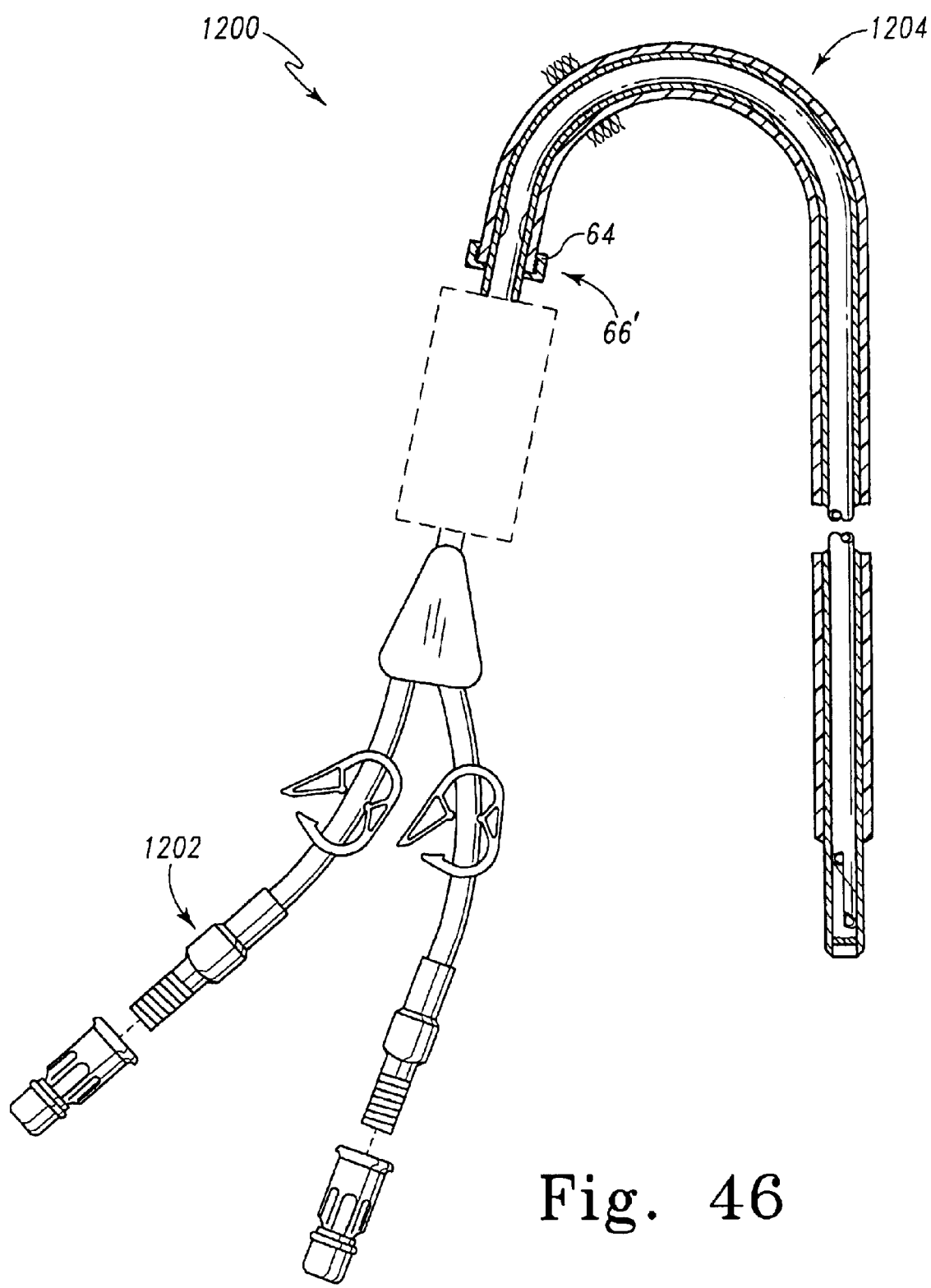
FIG. 46 is a side elevational view of another catheter system that incorporates the features of the present invention therein.
Figure 47:
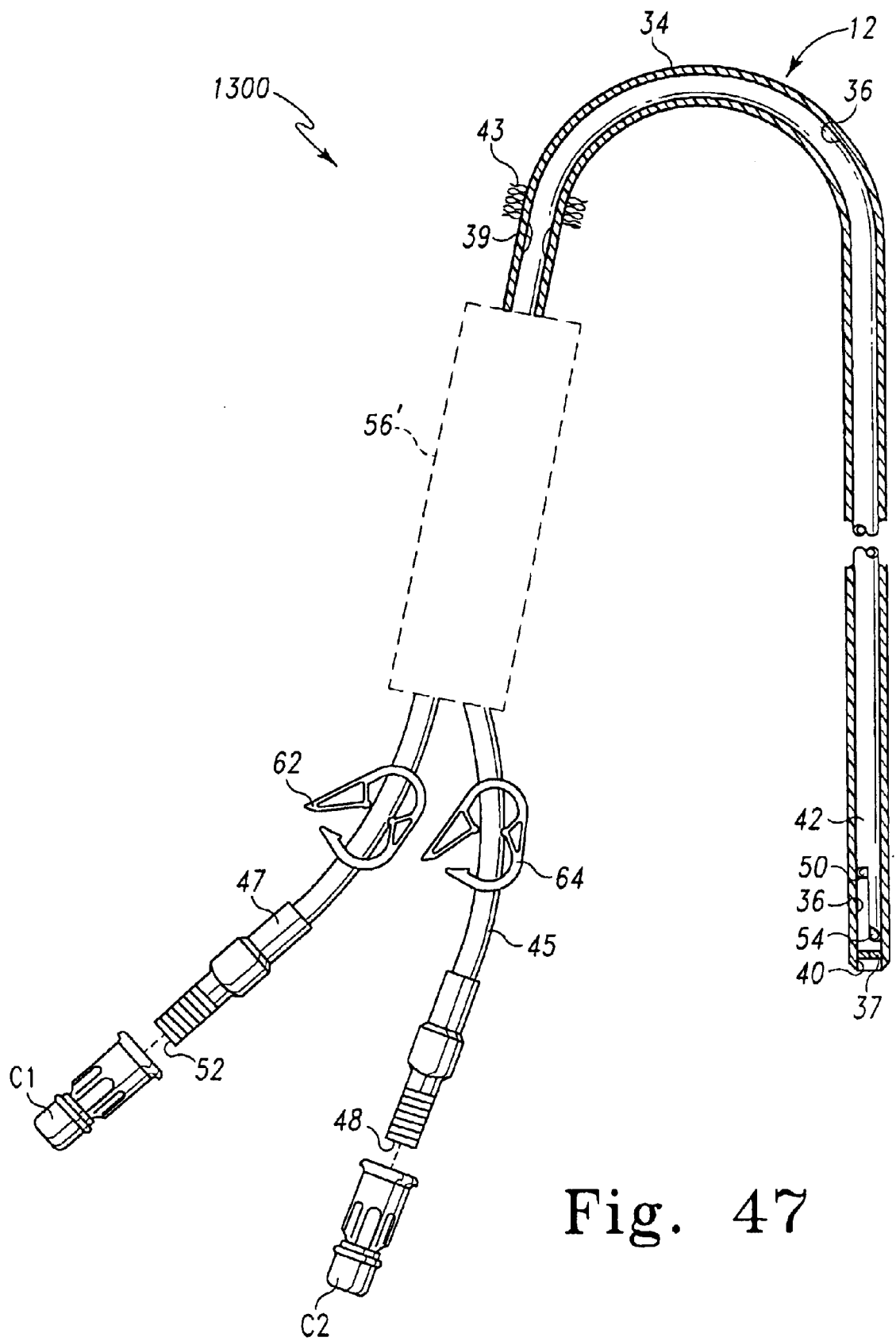
FIG. 47 is a side elevational view of still another catheter system that incorporates the features of the present invention therein.

Another catheter system 1200 that incorporates the features of the present invention therein is shown in FIG. 46. The catheter system 1200, which may be referred to a hybrid catheter system, includes an inner retractable catheter system 1202 and an outer guide catheter 1204. The inner catheter system 1202 is constructed and used in the same manner as the catheter system 12 that is disclosed in U.S. Pat. No. 6,190,371 issued to Maginot et al., except for two differences. The entire disclosure of U.S. Pat. No. 6,190,371 is hereby incorporation by reference. The first difference is that the tissue ingrowth member 43 disclosed in the '371 patent would not be included on the retractable inner catheter system 1202. The second difference is that the inner retractable catheter system 1202 has a locking mechanism 66' which is substantially identical in construction and use as the second locking mechanism 66 of the catheter system 16 disclosed in U.S. Pat. No. 6,156,016 issued to Maginot (see e.g. FIG. 6). The entire disclosure of U.S. Pat. No. 6,156,016 is hereby incorporation by reference.

The outer guide catheter 1204 is constructed and used in the same manner as the guide catheter 32 disclosed in U.S. Pat. No. 6,156,016 (e.g. see FIG. 4A) except for one difference. The one difference is that the outer guide catheter 1204 possesses a larger inner diameter to accommodate the positioning of the inner retractable catheter system 1202 therein as shown in FIG. 46.

The hybrid catheter system 1200 is implanted and used in the same manner as described with respect to the implantation and use of the catheter system 12 that is disclosed in U.S. Pat. No. 6,190,371. However, if for any reason the inner retractable catheter system 1202 becomes dysfunctional, the inner retractable catheter system 1202 could be replaced with a new inner retractable catheter system that is identical in construction and function to the inner retractable catheter system 1202. The inner retractable catheter system 1202 may be replaced in the same manner as described with respect to the replacement of the dialysis catheter 48 with the replacement dialysis catheter 58 as disclosed in U.S. Pat. No. 6,156,016.

Obviously, the catheter system 1200 may be modified in a similar manner to the modifications discussed above with respect to all of the above-described catheter systems. Moreover, all of the above-described catheter systems may be modified to incorporate any of the features of the catheter system 1200.

XII. Catheter System 1300

Another catheter system 1300 which incorporates the features of the present invention therein is shown in FIGS. 47–51. The catheter system 1300 is identical to the catheter system 12 described above and shown in FIGS. 1–11, except that the catheter system 1300 possesses yet another alternative locking mechanism 56' to the locking mechanism 56 of FIGS. 4–11. In particular, the locking mechanism 56' includes a wall 1302 having a number of detent recesses 1304 defined therein. The locking mechanism 56' may further include an arm assembly 1306. The arm assembly 1306 includes a ring 1308 which is positioned around and secured to the working catheter 42 of the catheter system 1300. The arm assembly 1306 further includes an arm 1310 connected to the ring 1308. The arm 1310 includes a tang 1312 located on a proximal end thereof.

Figure 48:
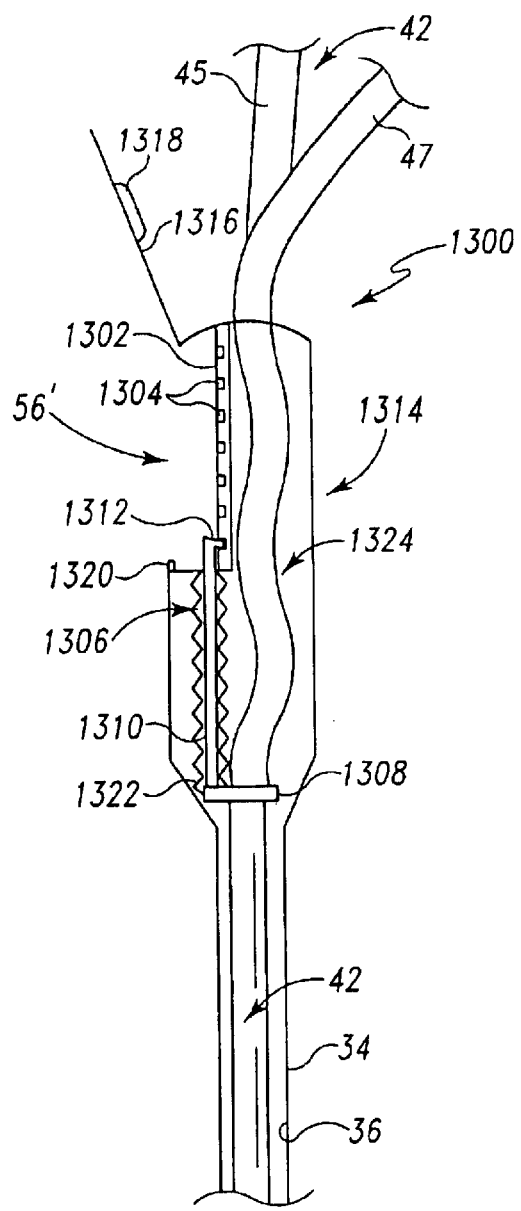
FIGS. 48, 49, 50, and 51 are views similar to FIG. 47, but showing more details of the locking mechanism of FIG. 47.
Figure 49:
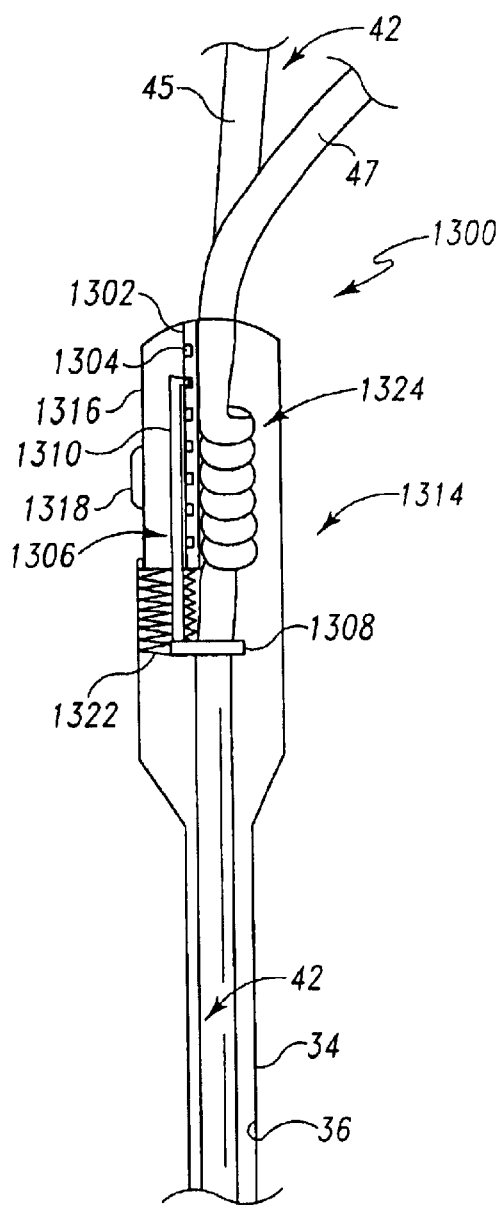

During use of the catheter system 1300, the tang 1312 cooperates with the detent recesses 1304 so as to selectively lock the working catheter 42 in relation to the guide catheter 34 at either a stowed position (see FIG. 10) or at an operative position (see FIG. 11). FIG. 48 (and FIG. 50) show the locking mechanism 56'when the working catheter 42 is locked to the guide catheter 34 in the operative position. FIG. 49 (and FIG. 51) show the locking mechanism 56' when the working catheter 42 is locked to the guide catheter 34 in the stowed position.

The guide catheter 34 of the catheter system 1300 includes a lock housing 1314. The lock housing 1314 includes a number of walls, including wall 1302, which enclose the components of the locking mechanism 56'. The housing 1314 further includes a door 1316 having a handle 1318. The door 1316 is pivotable from its open position shown in FIG. 48 (and FIG. 50) to its closed position shown in FIG. 49 (and FIG. 51). The housing 1314 further includes a stop 1320 configured to retain the door 1316 in its closed position.

Figure 50:
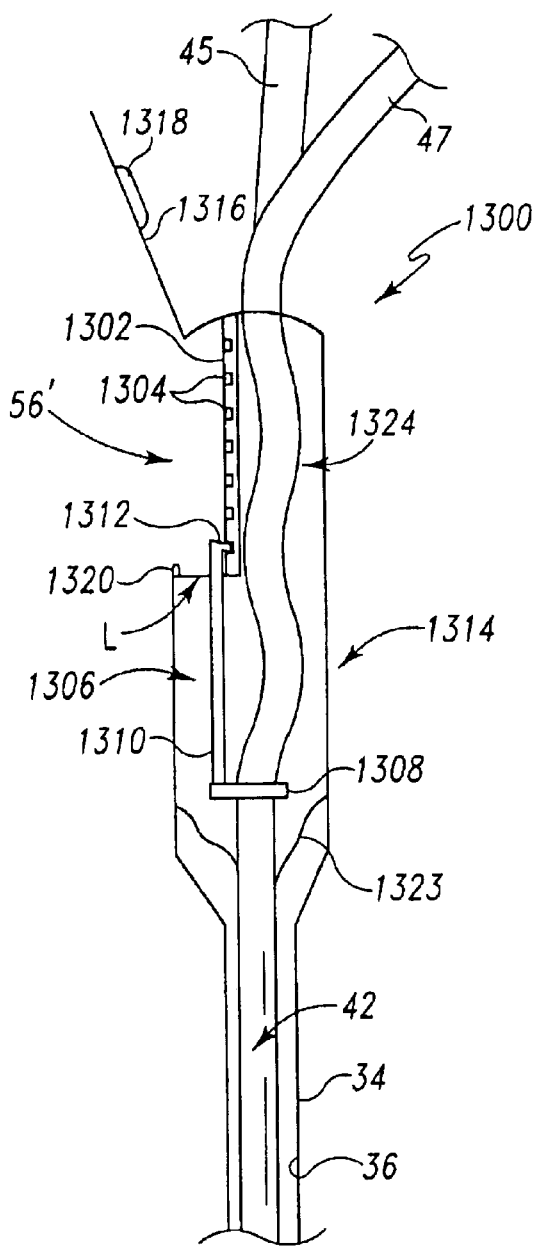
Figure 51:
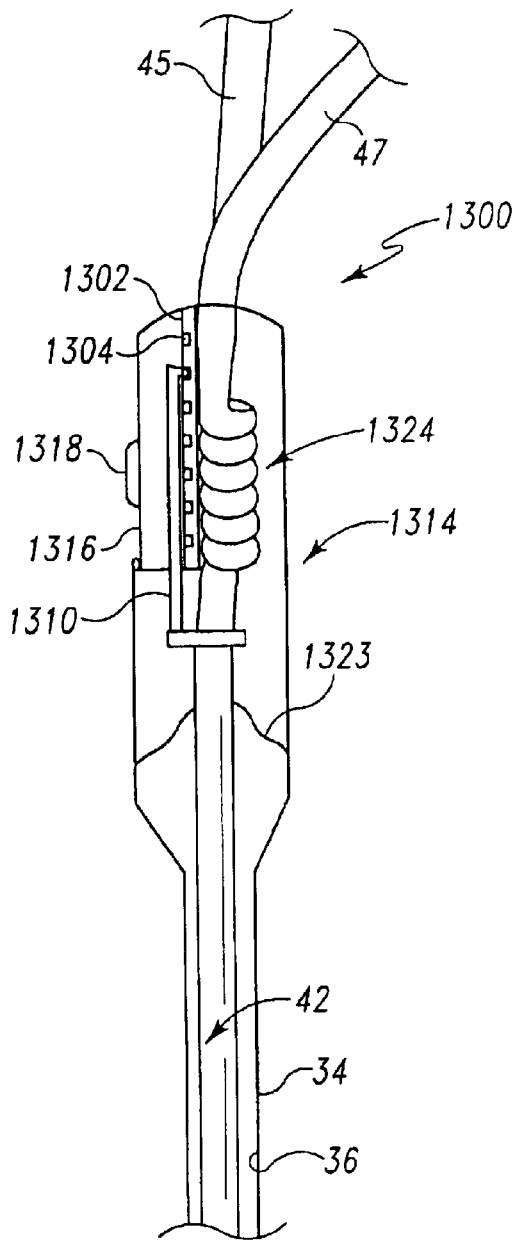

In order to further seal a lower portion of the working catheter 42 (i.e. the portion of the working catheter 42 located within the lock housing 1314 and all portions of the working catheter 42 distal thereto) within the guide catheter 34, an accordion shaped seal 1322 is positioned completely around a segment of the arm 1310 and attached to the ring 1308 at its distal end. The accordion shaped seal 1322 is attached to the housing at its proximal end as shown in FIGS. 48–49. Alternatively, as shown in FIGS. 50–51, the accordion seal 1322 may be replaced with a flexible diaphragm seal 1323 that completely surrounds the working catheter 42. In particular, the diaphragm seal 1323 is annular shaped and is attached at its outer periphery to the inner surface of the lock housing 1314 of the guide catheter 34, and further is attached at its inner periphery to the outer surface of the working catheter 42. The flexible diaphragm seal 1323 would have a substantially similar configuration and function to the flexible separating diaphragm 39A of FIG. 8A discussed hereinabove.

It should be noted that the working catheter 42 includes a coiled or helical segment 1324 that can be extended from its coiled configuration shown in FIG. 49 to its substantially straight configuration shown in FIG. 48. The segment 1324 is configured to retain its coiled shape as shown in FIG. 49 absent application of any external force thereto. The segment 1324 is formed to possess such a coiled shape in a similar manner to that commonly used in the medical device manufacturing arts to provide a pre-formed shape to a catheter (e.g. a pig-tailed catheter).

In operation, if a user applies downward force to the arm 1310 in order to move the working catheter 42 from its stowed position (see FIG. 10) to its operative position (see FIG. 11), the coiled segment moves from its coiled configuration (see FIG. 49) to its substantially straight configuration (see FIG. 48). Thereafter, the tang 1312 cooperates with the respective detent recess 1304 in order to retain the coiled segment 1324 in its substantially straight configuration as shown in FIG. 48 (and FIG. 50). If a user desires to return the working catheter from its operative position (see FIG. 11) to its stowed position (see FIG. 10), the user simply lifts the tang 1312 out of the respective detent recess 1304 and pulls upwardly until the arm is located at its position shown in FIG. 49. As the arm 1310 moves upwardly, the coiled segment springs back to its coiled configuration (see FIG. 49) due to the inherent spring-like characteristics of the preformed coiled segment 1324.

Moreover, it should be appreciated that the locking mechanism 56' may be modified to incorporate a supplemental force transmitting mechanism (not shown) in order to move the working catheter 42 in relation to the guide catheter 34 from its stowed position (see FIG. 10) to its operative position (see FIG. 11). In particular, such supplemental force transmitting mechanism may include a hydraulic or pneumatic device (not shown) that may be substituted for arm 1310. The hydraulic or pneumatic device would be coupled between an inner surface of the lock housing 1314 at a location L (see FIG. 50) and the ring 1308. The hydraulic or pneumatic device would include a rod and a cylinder (not shown). The hydraulic or pneumatic device would be operable to extend and retract the rod out of the cylinder to move the working catheter 42 in relation to the guide catheter 34. The hydraulic or pneumatic device would be actuated by a syringe that would be coupled to the cylinder of the hydraulic or pneumatic device via tubing.

XIII. Catheter System 1400

Figure 52:
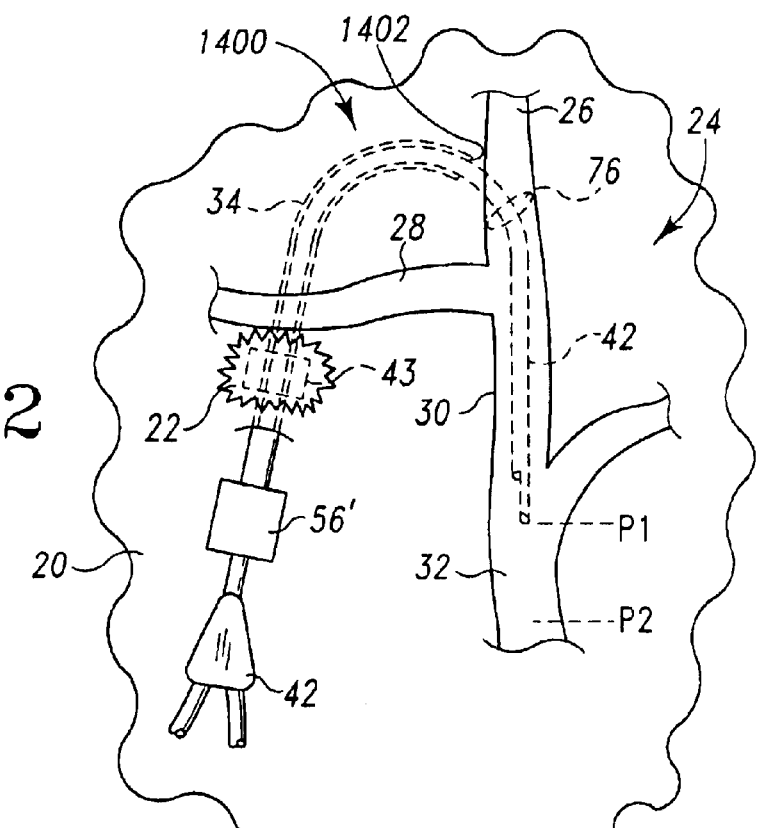
Figure 53:
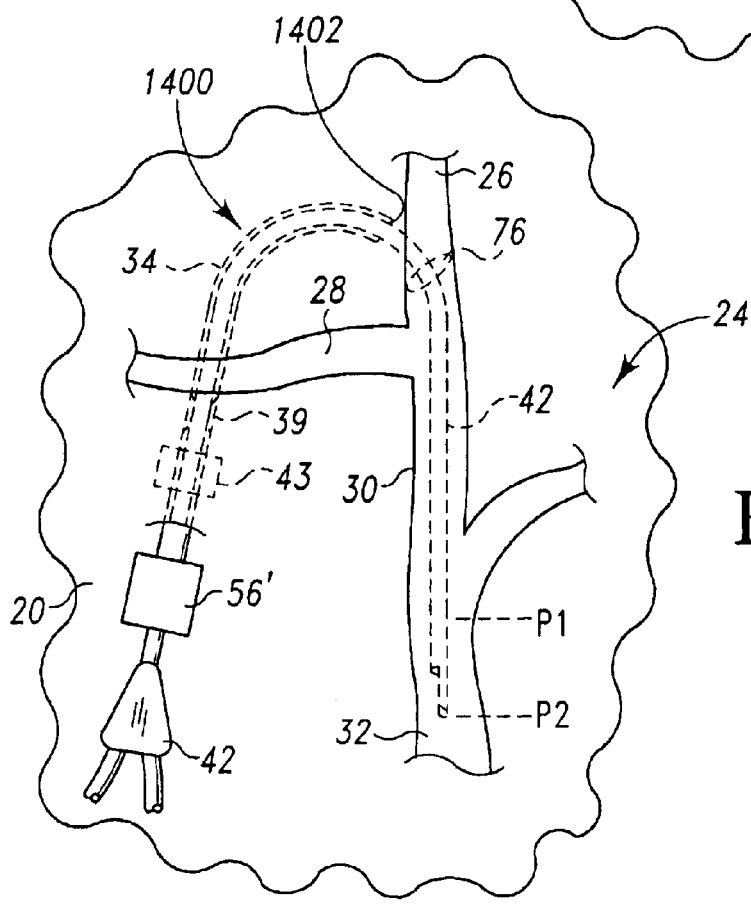

Another catheter system 1400 that incorporates the features of the present invention therein is shown in FIGS. 52–53. The catheter system 1400 is somewhat similar to the catheter system 12 discussed above. Thus, the same reference numerals are used in FIGS. 52 and 53 to designate common components that were previously discussed with regard to FIGS. 1–11. Moreover, the description of the components of the catheter system 1400 which are common to the catheter system 12 will not be undertaken since they are designated with common reference numerals and such components have been previously described hereinabove.

The catheter system 1400 of FIGS. 52 and 53 is used in substantially the same manner as herein described with respect to the catheter system 12. Moreover, the catheter system 1400 of FIGS. 52 and 53 is exactly the same in construction and configuration as the catheter system 12 shown in FIGS. 1–11, with the exception that the locking mechanism 56' is substituted for locking mechanism 56. Another exception is that the guide catheter 34 of the catheter system 1400 is much shorter in length than the guide catheter 34 of the catheter system 12, while the working catheter 42 of the catheter system 1400 of FIGS. 52 and 53 is the same length as the working catheter 42 of the catheter system 12. (For example, compare FIGS. 52 and 53 with FIG. 9). In particular, the length of the guide catheter 34 of the catheter system 1400 of FIGS. 52 and 53 is such that after it is placed in the body 14 as shown in FIGS. 52 and 53, its distal guide orifice 1402 is located entirely outside of the vascular system 24 in the subcutaneous tissue 22 preferably two centimeters proximal to the venotomy 76. Moreover, in this embodiment of the present invention shown in FIGS. 52 and 53, the distance between the most distal working orifice of the working catheter 42 and the distal guide orifice 1402 of the guide catheter 34 (in its extended configuration as shown in FIG. 53) is preferably approximately twenty-two centimeters. In contrast, in the embodiment shown in FIGS. 1–11, the distance between the most distal working orifice 54 of the working catheter 42 and the distal guide orifice 40 of the guide catheter 34 is preferably approximately three centimeters.

During operation, the working catheter 42 is able to be moved relative to the guide catheter 34 between its retracted position as shown in FIG. 52 and its extended position as shown in FIG. 53. More specifically, the most distal working orifice of the working catheter 42 of the catheter system 1400 is located at point P1 within the superior vena cava 32 (see FIG. 52) when the working catheter is positioned in its retracted position. However, the most distal working orifice of the working catheter 42 is located at point P2 within the superior vena cava 32 (see FIG. 52) when the working catheter is positioned in its extended position.

It is believed that, during use, a fibrin sheath will form around and envelope the portion of the working catheter 42 of the catheter system 1400 which is located in the vascular system 24 while the working catheter is positioned in its retracted position as shown in FIG. 52. It is believed that the fibrin sheath will be attached to the wall of the right internal jugular vein 26 near the venotomy where the working catheter enters the vascular system 24. The working catheter would be located in this retracted position between dialysis sessions. However, it is believed that when the working catheter is moved to its extended position as shown in FIG. 53 in order to carry out a dialysis session, a distal segment of the working catheter 42 will be advanced through a distal end of the fibrin sheath thereby exposing the two working distal orifices of the working catheter 42 to a flow of blood within the superior vena cava 32. The working catheter 42 will remain in this extended position for a duration of time sufficient to carry out a dialysis session. After the dialysis session is carried out, the working catheter 42 will be moved back to its retracted position as shown in FIG. 52 until another dialysis session is to be carried out.

There is a plurality of advantages of the present invention arising from the various features of each of the catheter systems described herein. It will be noted that alternative embodiments of each of the catheter systems of the present invention may not include all of the features described yet still benefit from at least some of the advantages of such features. Those of ordinary skill in the art may readily devise their own implementations of each of the catheter systems that incorporate one or more of the features of the present invention and fall within the spirit and scope of the present invention as defined by the appended claims.

It should be appreciated that any of the features of any one catheter system described herein may be used with any of the other catheter systems described herein.

What is claimed is:

1. A method of performing dialysis with a catheter system which includes (i) a working catheter having a distal working orifice, and (ii) a guide catheter having a guide lumen and a distal guide orifice, comprising the steps of:

locking said working catheter in an operative position in which (i) said working catheter extends through said guide lumen of said guide catheter and out of said distal guide orifice of said guide catheter, and (ii) said distal working orifice of said working catheter is positioned outside of said guide catheter;

performing a dialysis procedure including advancing and withdrawing blood through said working catheter while said working catheter is locked in said operative position; and after said dialysis procedure performing step, locking said working catheter in a stowed position in which (i) said working catheter extends into said guide lumen of said guide catheter, and (ii) said distal working orifice of said working catheter is positioned within said guide lumen of said guide catheter.

2. The method of claim 1, further comprising the step of advancing a quantity of blood clot dissolving liquid within said guide lumen of said guide catheter when said working catheter is locked in said stowed position.

3. The method of claim 2, wherein said blood clot dissolving liquid contacts said working catheter at said distal working orifice when said working catheter is locked in said stowed position.

4. The method of claim 3, wherein said blood clot dissolving liquid includes urokinase.

5. The method of claim 1, further comprising the step of:

inhibiting advancement of blood into contact with said working catheter at said distal working orifice with a distal valve while said working catheter is locked in said stowed position.

6. The method of claim 5, wherein said inhibiting step includes the step of inhibiting advancement of blood from a first location outside of said guide lumen to a second location inside of said guide lumen with said distal valve while said working catheter is locked in said stowed position.

7. The method of claim 6, wherein:

said distal working orifice is positioned on a proximal side of said distal valve when said working catheter is locked in said stowed position, and said distal working orifice is positioned on a distal side of said distal valve when said working catheter is locked in said operative position.

8. The method of claim 1, wherein:

said working catheter is a multiple lumen catheter which includes an advancement lumen and a withdrawal lumen, and said dialysis procedure performing step includes the steps of (i) advancing blood from a proximal end of said working catheter toward a distal end of said working catheter through said advancement lumen, and (ii) withdrawing blood from said distal end of said working catheter toward said proximal end of said working catheter through said withdrawal lumen.

9. The method of claim 1, wherein:

said working catheter includes a distal working segment in which said distal working orifice is defined, said distal working segment extends out of said distal guide orifice of said guide catheter so that said distal working orifice is positioned outside of said guide lumen when said working catheter is locked in said operative position, and said distal working segment is positioned completely within said guide catheter such that said distal working orifice is positioned within said guide lumen when said working catheter is locked in said stowed position.

10. The method of claim 1, further comprising the steps of:

advancing said guide catheter into a body of a patient so that (i) said distal guide orifice of said guide catheter is positioned within a blood vessel of said body, and (ii) a tissue ingrowth member is positioned in subcutaneous tissue of said body; and leaving said guide catheter within said body for a period of time sufficient to cause said subcutaneous tissue to become affixed to said tissue ingrowth member, wherein said tissue ingrowth member is secured to an outer surface of said guide catheter and configured to facilitate fibrous tissue growth therein, and wherein said guide catheter advancing step is performed prior to said dialysis procedure performing step.

11. A method of performing a series of dialysis procedures on a body of a patient with a catheter system which includes (i) a working catheter having a distal working orifice, and (ii) a guide catheter having a guide lumen and a distal guide orifice, comprising the steps of:

(a) locking said working catheter in an operative position in which (i) said working catheter extends through said guide lumen of said guide catheter and out of said distal guide orifice of said guide catheter, and (ii) said distal working orifice of said working catheter is positioned outside of said guide catheter;

(b) after step (a), performing an initial dialysis procedure on said body of said patient which includes advancing and withdrawing fluid through said working catheter while said working catheter is locked in said operative position, said working catheter being coupled to a dialysis machine during said initial dialysis procedure;

(c) after step (b), locking said working catheter in a stowed position in which (i) said working catheter extends into said guide lumen of said guide catheter, and (ii) said distal working orifice of said working catheter is positioned within said guide lumen of said guide catheter;

(d) after step (c), maintaining said working catheter in said stowed position during an idle period during which said catheter system is decoupled from said dialysis machine, said catheter system being located at least partially within said body of said patient throughout the entirety of said idle period;

(e) after step (d), locking said working catheter in said operative position; and (f) after step (e), performing a subsequent dialysis procedure on said body of said patient which includes advancing and withdrawing fluid through said working catheter while said working catheter is locked in said operative position, said working catheter being coupled to said dialysis machine during said subsequent dialysis procedure.

12. The method of claim 11, further comprising the step of:
    inhibiting advancement of blood into contact with said working catheter at said distal working orifice with a distal valve while said working catheter is locked in said stowed position.

13. The method of claim 12, wherein said inhibiting step includes the step of inhibiting advancement of blood from a first location outside of said guide lumen to a second location inside of said guide lumen with said distal valve while said working catheter is locked in said stowed position.

14. A method of performing dialysis on a body of a patient with a catheter system which includes (i) a conduit having a distal working orifice, and (ii) a guide catheter having a guide lumen and a distal guide orifice, comprising the steps of:
    locking said conduit to said guide catheter in an operative position in which said distal working orifice of said conduit is positioned outside of said guide catheter;
    performing an initial dialysis procedure including advancing and withdrawing blood through said conduit while said conduit is locked in said operative position; and
    after said initial dialysis procedure, locking said conduit to said guide catheter in a stowed position in which said distal working orifice of said conduit is positioned within said guide lumen of said guide catheter.

15. The method of claim 14, further comprising the step of performing a subsequent dialysis procedure including advancing and withdrawing blood through said conduit while said conduit is locked in said operative position, wherein:
    said catheter system is at least partially located at least partially within said body continuously between completion of said initial dialysis procedure and commencement of said subsequent dialysis procedure.

16. The method of claim 15, further comprising the step of:
    prior to said initial dialysis procedure performing step, attaching said catheter system to said body, wherein said catheter system remains attached to said body continuously between completion of said initial dialysis procedure performing step and commencement of said subsequent dialysis procedure performing step.

17. The method of claim 15, wherein:
    said initial dialysis procedure is an initial hemodialysis procedure, and
    said subsequent dialysis procedure is a subsequent hemodialysis procedure.

18. The method of claim 15, wherein:
    said initial dialysis procedure is an initial peritoneal dialysis procedure, and
    said subsequent dialysis procedure is a subsequent peritoneal procedure.

19. The method of claim 18, wherein said conduit is a working catheter.

20. The method of claim 14, further comprising the step of advancing a quantity of blood clot dissolving liquid within said guide lumen of said guide catheter when said conduit is locked in said stowed position.

21. The method of claim 20, wherein said blood clot dissolving liquid contacts said conduit at said distal working orifice when said conduit is locked in said stowed position.

22. The method of claim 21, wherein said blood clot dissolving liquid includes urokinase.

23. The method of claim 14, further comprising the step of:
    inhibiting advancement of blood into contact with said conduit at said distal working orifice with a distal valve while said conduit is locked in said stowed position.

24. The method of claim 23, wherein said inhibiting step includes the step of inhibiting advancement of blood from a first location outside of said guide lumen to a second location inside of said guide lumen with said distal valve while said conduit is locked in said stowed position.

25. The method of claim 24, wherein:
    said distal working orifice is positioned on a proximal side of said distal valve when said conduit is locked in said stowed position, and
    said distal working orifice is positioned on a distal side of said distal valve when said conduit is locked in said operative position.

26. The method of claim 14, wherein:
    said conduit is a multiple lumen catheter which includes an advancement lumen and a withdrawal lumen, and
    said initial dialysis procedure performing step includes the steps of (i) advancing blood from a proximal end of said conduit toward a distal end of said conduit through said advancement lumen, and (ii) withdrawing blood from said distal end of said conduit toward said proximal end of said conduit through said withdrawal lumen.

27. The method of claim 14, wherein:
    said conduit includes a distal working segment in which said distal working orifice is defined,
    said distal working segment extends out of said distal guide orifice of said guide catheter so that said distal working orifice is positioned outside of said guide lumen when said conduit is locked in said operative position, and
    said distal working segment is positioned completely within said guide catheter such that said distal working orifice is positioned within said guide lumen when said conduit is locked in said stowed position.

28. A method of performing a series of medical procedures on a body of a patient, comprising the steps of:
    securing a catheter system to said body using a tunneled catheter technique;
    performing an initial medical procedure on said body after said securing step, said initial medical procedure including advancing fluid through a distal orifice of a conduit of said catheter system, and said distal orifice being located outside of a guide lumen of a guide catheter of said catheter system during said initial medical procedure performing step;
    after said initial medical procedure performing step, locking said distal orifice of said conduit within said guide lumen of said guide catheter of said catheter system; and
    performing a subsequent medical procedure on said body after said locking step, said subsequent medical procedure including advancing fluid though said distal orifice of said conduit of said catheter system, and said distal orifice being located outside of said guide lumen of said guide catheter of said catheter system during said subsequent medical procedure performing step.

29. The method of claim 28, wherein:
    said initial medical procedure is an initial dialysis procedure, and
    said subsequent medical procedure is a subsequent dialysis procedure.

30. The method of claim 29, wherein:
said initial dialysis procedure is an initial hemodialysis procedure, and
said subsequent dialysis procedure is a subsequent hemodialysis procedure.

31. The method of claim 29, wherein:
said initial dialysis procedure is an initial peritoneal dialysis procedure, and
said subsequent dialysis procedure is a subsequent peritoneal procedure.

32. The method of claim 28, wherein:
said initial medical procedure is an initial plasmapheresis procedure, and
said subsequent medical procedure is a subsequent plasmapheresis procedure.

33. The method of claim 28, wherein:
said initial medical procedure is an initial total parenteral nutrition administration procedure, and
said subsequent medical procedure is a subsequent total parenteral nutrition administration procedure.

34. The method of claim 28, wherein:
said initial medical procedure is an initial chemotherapy administration procedure, and
said subsequent medical procedure is a subsequent chemotherapy administration procedure.

35. The method of claim 28, wherein:
said initial medical procedure is an initial blood transfusion procedure, and
said subsequent medical procedure is a subsequent blood transfusion procedure.

36. The method of claim 28, wherein:
said initial medical procedure is an initial blood sampling procedure, and
said subsequent medical procedure is a subsequent blood sampling procedure.

37. The method of claim 28, wherein said securing step includes the steps of:
advancing said guide catheter into said body so that (i) said distal guide orifice of said guide catheter is positioned within a blood vessel of said body, and (ii) a tissue ingrowth member which is secured to an outer surface of said guide catheter is positioned in subcutaneous tissue of said body; and
leaving said guide catheter within said body for a period of time sufficient to cause said subcutaneous tissue to become affixed to said tissue ingrowth member.

38. The method of claim 28, wherein said catheter system is located within said body continuously between completion of said initial medical procedure performing step and commencement of said subsequent medical procedure performing step.

39. The method of claim 28, wherein said catheter system remains attached to said body continuously between completion of said initial medical procedure performing step and commencement of said subsequent medical procedure performing step.

40. The method of claim 28, further comprising the step of advancing a quantity of blood clot dissolving liquid within said guide lumen of said guide catheter while said distal orifice of said conduit is locked within said guide lumen of said guide catheter.

41. The method of claim 40, wherein said blood clot dissolving liquid contacts said conduit at said distal working orifice while said distal orifice of said conduit is locked within said guide lumen of said guide catheter.

42. The method of claim 41, wherein said blood clot dissolving liquid includes urokinase.

43. The method of claim 28, further comprising the step of:
inhibiting advancement of blood into contact with said conduit at said distal working orifice with a distal valve while said distal orifice of said conduit is locked within said guide lumen of said guide catheter.

44. The method of claim 43, wherein said inhibiting step includes the step of inhibiting advancement of blood from a first location outside of said guide lumen to a second location inside of said guide lumen with said distal valve while said distal orifice of said conduit is locked within said guide lumen of said guide catheter.

45. The method of claim 44, wherein:
said distal working orifice is positioned on a proximal side of said distal valve while said distal orifice of said conduit is locked within said guide lumen of said guide catheter, and
said distal working orifice is positioned on a distal side of said distal valve during (i) said initial medical procedure performing step, and (ii) said subsequent medical procedure performing step.

46. The method of claim 28, wherein:
said conduit is a multiple lumen catheter which includes an advancement lumen and a withdrawal lumen, and
said medical procedure performing step includes the steps of (i) advancing blood from a proximal end of said conduit toward a distal end of said conduit through said advancement lumen, and (ii) withdrawing blood from said distal end of said conduit toward said proximal end of said conduit through said withdrawal lumen.

47. The method of claim 28, wherein:
said conduit includes a distal working segment in which said distal working orifice is defined,
said distal working segment extends out of said distal guide orifice of said guide catheter so that said distal working orifice is positioned outside of said guide lumen during said initial medical procedure performing step, and
said distal working segment is positioned completely within said guide catheter such that said distal working orifice is positioned within said guide lumen while said distal orifice of said conduit is locked within said guide lumen of said guide catheter.

48. The method of claim 28, wherein:
said guide catheter further has a proximal guide orifice, and
said conduit extends through said proximal guide orifice, said guide lumen, and said distal guide orifice during said initial medical procedure performing step.

49. The method of claim 28, wherein said conduit is a working catheter.

50. A method of performing a series of dialysis procedures on a body of a patient, comprising the steps of:
performing an initial dialysis procedure on said body including advancing blood through a distal orifice of a conduit of a catheter system, and said distal orifice being located outside of a guide lumen of a guide catheter of said catheter system during said initial dialysis procedure performing step;
after said initial dialysis procedure performing step, locking said distal orifice of said conduit within said guide lumen of said guide catheter of said catheter system; and performing a subsequent dialysis procedure on said body after said locking step, said dialysis procedure including advancing blood though said distal orifice of said conduit of said catheter system, and said distal orifice being located outside of said guide lumen of said guide catheter of said catheter system during said subsequent dialysis procedure performing step.

51. The method of claim 50, wherein said conduit is located within said body continuously between completion of said initial dialysis procedure performing step and commencement of said subsequent dialysis procedure performing step.

52. The method of claim 50, further comprising the step of:

prior to said initial dialysis procedure performing step, attaching said catheter system to said body, wherein said working catheter remains attached to said body continuously between completion of said initial dialysis procedure performing step and commencement of said subsequent dialysis procedure performing step.

53. The catheter system of claim 50, wherein said conduit is a working catheter.

54. The method of claim 50, wherein:

said initial dialysis procedure is an initial hemodialysis procedure, and said subsequent dialysis procedure is a subsequent hemodialysis procedure.

55. The method of claim 50, wherein:

said initial dialysis procedure is an initial peritoneal dialysis procedure, and said subsequent dialysis procedure is a subsequent peritoneal procedure.

56. The method of claim 50, wherein said initial dialysis procedure performing step, said locking step, and said subsequent dialysis procedure performing step are each performed while said catheter system is secured to said body using said tunneled catheter technique.

57. The method of claim 52, wherein said attaching step includes the steps of:

attaching said catheter system to an attachment mechanism which includes at least one extension, and suturing said at least one extension to said body.

58. The method of claim 52, wherein said attaching step includes the step of securing said catheter system to said body using a tunneled catheter technique.

59. The method of claim 50, further comprising the step of advancing a quantity of blood clot dissolving liquid within said guide lumen of said guide catheter while said distal orifice of said conduit is locked within said guide lumen of said guide catheter.

60. The method of claim 59, wherein said blood clot dissolving liquid contacts said conduit at said distal working orifice while said distal orifice of said conduit is locked within said guide lumen of said guide catheter.

61. The method of claim 59, wherein said blood clot dissolving liquid includes urokinase.

62. The method of claim 50, further comprising the step of:

inhibiting advancement of blood into contact with said conduit at said distal working orifice with a distal valve while said distal orifice of said conduit is locked within said guide lumen of said guide catheter.

63. The method of claim 62, wherein said inhibiting step includes the step of inhibiting advancement of blood from a first location outside of said guide lumen to a second location inside of said guide lumen with said distal valve while said distal orifice of said conduit is locked within said guide lumen of said guide catheter.

64. The method of claim 63, wherein:

said distal working orifice is positioned on a proximal side of said distal valve while said distal orifice of said conduit is locked within said guide lumen of said guide catheter, and said distal working orifice is positioned on a distal side of said distal valve during (i) said initial dialysis procedure performing step, and (ii) said subsequent dialysis procedure performing step.

65. The method of claim 50, wherein:

said conduit is a multiple lumen catheter which includes an advancement lumen and a withdrawal lumen, and said initial dialysis procedure performing step includes the steps of (i) advancing blood from a proximal end of said conduit toward a distal end of said conduit through said advancement lumen, and (ii) withdrawing blood from said distal end of said conduit toward said proximal end of said conduit through said withdrawal lumen.

66. The method of claim 50, wherein:

said conduit includes a distal working segment in which said distal working orifice is defined, said distal working segment extends out of a distal guide orifice of said guide catheter so that said distal working orifice is positioned outside of said guide lumen during said initial dialysis procedure performing step, and said distal working segment is positioned completely within said guide catheter such that said distal working orifice is positioned within said guide lumen while said distal orifice of said conduit is locked within said guide lumen of said guide catheter.

67. The method of claim 50, wherein:

said guide catheter further has a proximal guide orifice, and said conduit extends through said proximal guide orifice, said guide lumen, and said distal guide orifice during said initial dialysis procedure performing step.

* * * * *